(12) United States Patent
Audat et al.

(10) Patent No.: US 11,939,390 B2
(45) Date of Patent: Mar. 26, 2024

(54) METHODS OF TREATING MULTIPLE MYELOMA

(71) Applicant: Sanofi-Aventis U.S. LLC, Bridgewater, NJ (US)

(72) Inventors: Heloise Audat, Paris (FR); Audrey Bonestebe, Paris (FR); Frank Campana Zambrano, Sudbury, MA (US); Sylvain Huille, Paris (FR); Solenn Le-Guennec, Paris (FR); Lucie Manache-Alberici, Paris (FR)

(73) Assignee: Sanofi-Aventis U.S. LLC, Bridgewater, NJ (US)

( * ) Notice: Subject to any disclaimer, the term of this patent is extended or adjusted under 35 U.S.C. 154(b) by 301 days.

(21) Appl. No.: 16/775,025

(22) Filed: Jan. 28, 2020

(65) Prior Publication Data
US 2020/0239589 A1 Jul. 30, 2020

Related U.S. Application Data

(60) Provisional application No. 62/943,716, filed on Dec. 4, 2019, provisional application No. 62/931,014, filed on Nov. 5, 2019, provisional application No. 62/899,094, filed on Sep. 11, 2019, provisional application No. 62/861,954, filed on Jun. 14, 2019, provisional application No. 62/847,826, filed on May 14, 2019, provisional application No. 62/797,876, filed on Jan. 28, 2019.

(30) Foreign Application Priority Data

Dec. 3, 2019 (EP) .................................... 19306554

(51) Int. Cl.
| | | |
|---|---|---|
| *C07K 16/28* | (2006.01) | |
| *A61K 31/454* | (2006.01) | |
| *A61K 31/573* | (2006.01) | |
| *A61K 39/00* | (2006.01) | |
| *A61K 39/395* | (2006.01) | |
| *A61P 35/00* | (2006.01) | |
| *C12Q 1/6869* | (2018.01) | |

(52) U.S. Cl.
CPC ........ *C07K 16/2896* (2013.01); *A61K 31/454* (2013.01); *A61K 31/573* (2013.01); *A61P 35/00* (2018.01); *C12Q 1/6869* (2013.01); *A61K 39/395* (2013.01); *A61K 2039/505* (2013.01); *A61K 2039/545* (2013.01)

(58) Field of Classification Search
CPC ............ C07K 16/2896; C07K 2317/24; A61K 31/454; A61K 31/573; A61K 2039/505; A61K 9/20; A61K 9/48; A61K 9/0019; A61K 31/69; A61K 47/183; A61K 47/26; A61K 2039/54; A61K 2039/545; A61K 2300/00; A61K 39/395; A61K 39/3955; A61K 9/08; A61K 39/39591; A61K 47/02; A61K 47/12; A61K 47/22; A61P 35/00; C12Q 1/6869
See application file for complete search history.

(56) References Cited

U.S. PATENT DOCUMENTS 8,153,765 B2   4/2012  Park

FOREIGN PATENT DOCUMENTS

| RU | 2515108 C2 | 5/2014 |
|---|---|---|
| WO | WO2008047242 A2 | 4/2008 |
| WO | WO2008047242 A3 | 6/2008 |
| WO | WO2008047242 A9 | 2/2009 |
| WO | WO2008047242 A8 | 8/2009 |
| WO | WO2016022589 A2 | 2/2016 |
| WO | 2016187546 A1 | 11/2016 |
| WO | 2020160020 A1 | 8/2020 |

OTHER PUBLICATIONS

Van de Donk NW, Moreau P, Plesner T, Palumbo A, Gay F, Laubach JP, Malavasi F, Avet-Loiseau H, Mateos MV, Sonneveld P, Lokhorst HM, Richardson PG. Clinical efficacy and management of monoclonal antibodies targeting CD38 and SLAMF7 in multiple myeloma. Blood. Feb. 11, 2016;127(6):681-95. (Year: 2016).*
Palumbo et al., Revised International Staging System for Multiple Myeloma: A Report From International Myeloma Working Group. J Clin Oncol. Sep. 1, 20150;33(26):2863-9. doi: 10.1200/JCO.2015.61.2267. Epub Aug. 3, 2015. (Year: 2015).*
Hulin, C., Beksac, M., Goodman, H.J et al. Antibody interference and response kinetics of isatuximab plus pomalidomide and dexamethasone in multiple myeloma. Blood Cancer J. 11, 169 (2021). (Year: 2021).*
Attal et al., ICARIA-MM study group. Isatuximab plus pomalidomide and low-dose dexamethasone versus pomalidomide and low-dose dexamethasone in patients with relapsed and refractory multiple myeloma(ICARIA-MM): a randomised, multicentre, open-label, phase 3 study. Lancet. Dec. 7, 2019;394(10214):2096-2107 (Year: 2019).*
Richardson et al., Isatuximab plus pomalidomide/dexamethasone versus pomalidomide/dexamethasone in relapsed/refractory multiple myeloma: ICARIA Phase III study design. Future Oncol. May 2018;14(11):1035-1047. (Year: 2017).*

(Continued)

*Primary Examiner* — Hong Sang
(74) *Attorney, Agent, or Firm* — MORRISON & FOERSTER LLP

(57) ABSTRACT

The present disclosure provides methods for treating multiple myeloma (such as refractory multiple myeloma or relapsed and refractory multiple myeloma) in an individual who received at least two prior therapies for multiple myeloma. The methods comprise administering to the individual an anti-CD38 antibody, pomalidomide, and dexamethasone. Also provided are methods of improving renal impairment in an individual having multiple myeloma.

19 Claims, 8 Drawing Sheets
(5 of 8 Drawing Sheet(s) Filed in Color)
Specification includes a Sequence Listing.

(56) References Cited

OTHER PUBLICATIONS

ClinicalTrials.gov (Jan. 11, 2019). "NCT02990338—Multinational Clinical Study Comparing Isatuximab, Pomalidomide, and Dexamethasone toPomalidomide and Dex Refractory or Relapsed and Refractory Multiple Myeloma Patients (ICARIA-MM)," 10 pages, retrieved from the Internet, URL:https://clinicaltrials.gov/ct2/history/NCT02990338?V42=View#StudyPageTop.

Dimopoulos, M.A. et al. (2013). "Primary Therapy of Waldenstrom Macroglobulinemia (WM) With Weekly Bortezomib, Low-Dose Dexamethasone, and Rituximab (BDR): Long-Term Results of a Phase 2 Study of the European Myeloma Network (EMN)," Blood 122(19):32176-3282.

Durie, B.G.M. et al. (Jul. 20, 2006) "International Uniform Response Criteria For Multiple Myeloma," Leukemia 20:1467-1473.

Flores-Montero, J. et al. (Jan. 20, 2017). "Next Generation Flow For Highly Sensitive and Standardized Detection of Minimal Residual Disease in Multiple Myeloma," Leukemia 31(10):2094-2103.

Goldmacher, V.S. et al. (Nov. 1, 1994). "Anti-CD38-Blocked Ricin: An Immunotoxin For the Treatment of Multiple Myeloma," 84(9):3017-3025.

Graham. F.L. et al. (1977). "Characteristics of a Human Cell Line Transformed by DNA from Human Adenovirus Type 5," J. Gen Virol. 36:59-74.

Kabat E.A. et al. (1991). "Sequences of Proteins of Immunological Interest, 5th Ed. Public Health Service," National Institutes of Health, Bethesda, MD. pp. iii-xix. (Table of Contents Only).

Kumar, S. et al. (Aug. 2016). "International Myeloma Working Group consensus criteria for response and minimal residual disease assessment in multiple myeloma," Lancet Oncol 17(8):e328-e346.

Lin, P. et al. (2004). "Flow Cytometric Immunophenotypic Analysis of 306 Cases of Multiple Myeloma," Am J Clin Pathol 121:482-488.

Mather, J.P. et al. (1980). "Establishment and Characterization of Two Distinct Mouse Testicular Epithelial Cell Lines," Biology of Reproduction 23:243-252.

Mather, J.P. et al. (1982). "Culture of Testicular Cells in Hormone-Supplemented Serum-Free Medium," Annals N.Y. Acad. Sci. 383:44-68.

Mikhael, J. et al. (Jun. 1, 2018). "Final Results of A Phase Ib Study of Isatuximab (ISA) Plus Pomalidomide (Pom) and Dexamethasone (Dex) in Relapsed/Refractory Multiple Myeloma (RRMM)," Journal of Clinical Oncology 36(15), 5 pages.

Oken, M.M. et al. (Dec. 1982). "Toxicity and Response Criteria of the Eastern Cooperative Oncology Group," Am J Clin Oncol. 5(6):649-655.

Paul, W.E. ed., Fundamental Immunology: Second Edition, Raven Press, New York at (1989) pp. 332-336.

Richardson, P.G. et al. (May 1, 2018). "Isatuximab Plus Pomalidomide/Dexamethasone Versus Pomalidomide/Dexamethasone in Relapsed/Refractory Multiple Myeloma: I Caria Phase III Study Design," Future Onocology 14(11):1035-1047.

Rollig, C. et al. (May 30, 2015, e-pub Dec. 23, 2014). "Multiple Myeloma," Lancet 385(9983):2197-2208.

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

Willan, J. et al. (2016). "Multiple Myeloma in the Very Elderly Patient: Challenges And Solutions," Clinical Interventions in Aging 11:423-435.

Yazaki, P.J. et al. (2003). "Expression of Recombinant Antibodies in Mammalian Cell Lines," Methods in Molecular Biology, vol. 248 B.K.C. Lo, ed., Humana Press, Totowa, N.J. pp. 255-268.

International Preliminary Report on Patentability dated Jul. 27, 2021 for PCT Application No. PCT/US2020/015455, filed Jan. 28, 2020, 7 pages.

International Search Report and Written Opinion of the International Searching Authority dated Mar. 30, 2020, for International Application No. PCT/US2020/015455, filed Jan. 28, 2020, 13 pages.

Mizuno, S. (Jul. 2016). "Multiple Myeloma: from Diagnosis to the Up-to-date Treatment. Topics: IV. Multiple Myeloma with Renal Impairment and Monoclonal Gammopathy of Renal Significance," Journal of the Japanese Society of Internal Medicine 105(7): 1224-1230, 9 pages (English Abstract).

\* cited by examiner

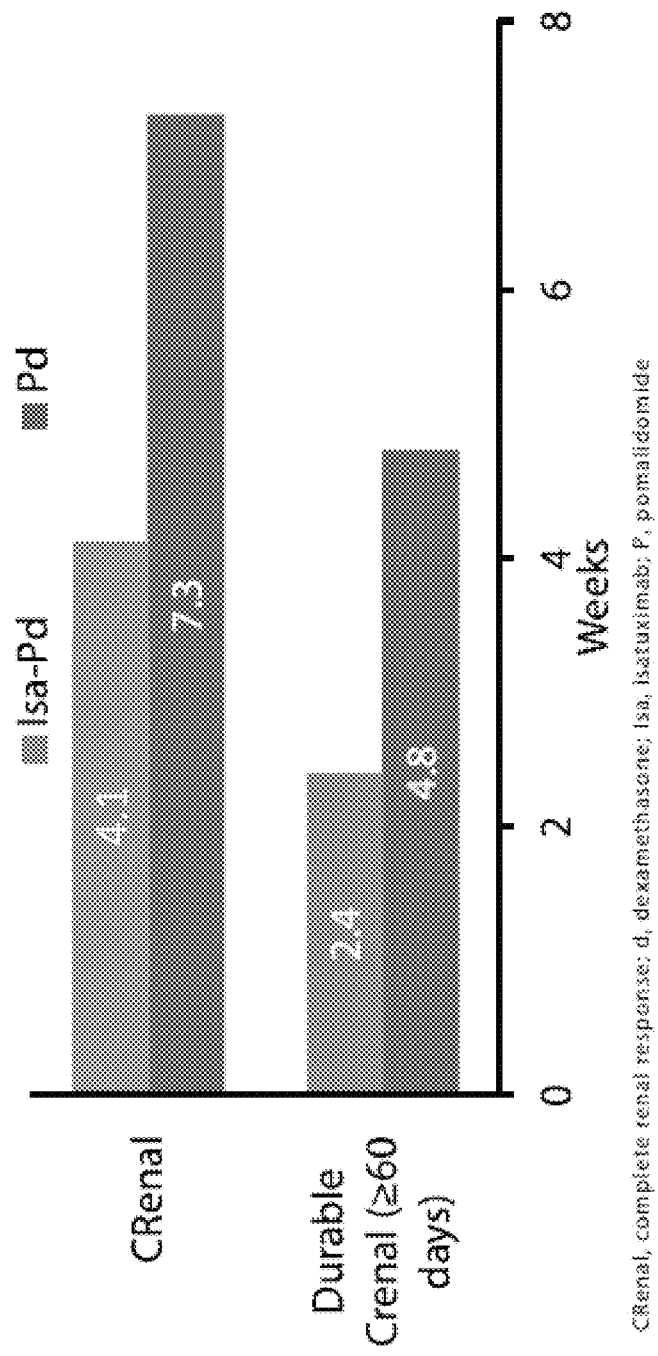

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp Tyr Trp Met Gln
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Thr Ile Tyr Pro Gly Asp Gly Asp Thr Gly Tyr Ala Gln Lys Phe Gln
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Gly Asp Tyr Tyr Gly Ser Asn Ser Leu Asp Tyr
```

-continued

```
<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Lys Ala Ser Gln Asp Val Ser Thr Val Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ser Ala Ser Tyr Arg Tyr Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln His Tyr Ser Pro Pro Tyr Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 8
<211> LENGTH: 108
<212> TYPE: PRT
```

```
<213> ORGANISM: Artificial Sequence
<220> FEATURE:
<223> OTHER INFORMATION: Synthetic Construct

<400> SEQUENCE: 8

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Ala Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105

<210> SEQ ID NO 10
<211> LENGTH: 449
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60
```

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
            85                  90                  95

Ala Arg Gly Asp Tyr Tyr Gly Ser Asn Ser Leu Asp Tyr Trp Gly Gln
        100                 105                 110

Gly Thr Ser Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 11
<211> LENGTH: 214
<212> TYPE: PRT

<213> ORGANISM: Artificial Sequence
<220> FEATURE:
<223> OTHER INFORMATION: Synthetic Construct

<400> SEQUENCE: 11

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

METHODS OF TREATING MULTIPLE MYELOMA

CROSS REFERENCE TO RELATED APPLICATIONS

This application claims the priority benefit of European Patent Application No. 19306554.7, filed Dec. 3, 2019; U.S. Provisional Application No. 62/943,716, filed Dec. 4, 2019; U.S. Provisional Application No. 62/931,014, filed Nov. 5, 2019; U.S. Provisional Application No. 62/899,094, filed Sep. 11, 2019; U.S. Provisional Application No. 62/861,954, filed Jun. 14, 2019; U.S. Provisional Application No. 62/847,826, filed May 14, 2019; U.S. Provisional Application No. 62/797,876, filed Jan. 28, 2019; the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952031200SEQLIST.txt, date recorded: Jan. 23, 2020, size: 11 KB).

FIELD

The present disclosure relates to methods of treating multiple myeloma by administering an anti-CD38 antibody in combination with pomalidomide and dexamethasone.

BACKGROUND

Multiple myeloma (MM) is a malignant plasma cell disease that is characterized by clonal proliferation of plasma cells in the bone marrow (BM) and the production of excessive amounts of a monoclonal immunoglobulin (usually of the IgG or IgA type or free urinary light chain, i.e., paraprotein, M-protein or M-component). Patients with MM can experience bone pain, bone fractures, fatigue, anemia, infections, hypercalcemia, and kidney problems (Rollig et al. (2015) Lancet. 385(9983):2197-208). The expression of CD38 is especially notable in MM as >98% of patients are positive for this protein (Goldmacher et al. (1994) Blood. 84(9):3017-25; Lin et al. (2004) Am J Clin Pathol. 121(4): 482-8). The strong and uniform expression of CD38 on malignant clonal MM cells contrasts with the restricted expression pattern on normal cells suggesting this antigen may be useful for specific targeting of tumor cells.

The current aim of MM therapy is to control the disease as effectively as possible, to maximize quality of life and to prolong survival. The disease trajectory varies for each patient, but relapses are inevitable, and the depth and duration of response to each treatment following relapse are generally diminished. In general, MM patients will receive an average of 4 to 8 different regimens during their lifespan using agents such as proteasome inhibitors (e.g., bortezomib, ixazomib, and carfilzomib) and immune modulatory agents or "IMiDs®" (e.g., lenalidomide and thalidomide), monoclonal antibodies (e.g., elotuzumab), histone deacetylase (HDAC) inhibitors (e.g., panobinostat) alone or in combination. However, once a patient becomes refractory to those agents, survival is limited and newer treatment options are needed to treat patients after they have failed stem cell transplant (SCT), chemotherapy, proteasome inhibitors, and immunomodulatory drugs (IMiDs®). Despite the dramatic improvement in patient outcomes with newer therapies, MM remains an incurable disease. Thus, the treatment of patients who have received at least 2 different lines of therapy including a proteasome inhibitor and an immunomodulatory agent or who are double refractory to a proteasome inhibitor and an IMiD® remains an unmet medical need.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY

Provided is an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6) for use in treating multiple myeloma in an individual, wherein the treatment comprises administering to the individual the anti-CD38 antibody, pomalidomide and dexamethasone, wherein the anti-CD38 antibody is administered at a dose of 10 mg/kg, the pomalidomide is administered at a dose of 4 mg, and the dexamethasone is administered at a dose of 40 mg individuals under 75 years of age, or the dexamethasone is administered at a dose of 20 mg to individuals 75 years of age or older, wherein the individual received at least two prior therapies for multiple myeloma, wherein at least one of the at least two prior therapies for multiple myeloma was lenalidomide and at least one of the two prior therapies was a proteasome inhibitor, and wherein the treatment extends progression free survival (PFS) and/or overall survival (OS) of the individual.

Provided is an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6) for use in method of reversing renal function impairment in an individual with multiple myeloma, wherein the method comprises administering to the individual the anti-CD38 antibody, pomalidomide and dexamethasone, wherein the anti-CD38 antibody is administered at a dose of 10 mg/kg, the pomalidomide is administered at a dose of 4 mg, and the dexamethasone is administered at a dose of 40 mg individuals under 75 years of age, or the dexamethasone is administered at a dose of 20 mg to individuals 75 years of age or older, wherein the individual has received at least two prior therapies for multiple myeloma, and wherein at least one of the at least two prior therapies for multiple myeloma was lenalidomide and at least one of the at least two prior therapies was a proteasome inhibitor.

Also provided is a liquid pharmaceutical formulation comprising (a) isatuximab at a concentration of 5-20 mg/ml; (b) a buffering agent selected from the group consisting of: histidine, acetate, and phosphate; (c) an excipient selected from the group consisting of: sucrose and mannitol, and (d) polysorbate 80 (PS80). In some embodiments, the isatuximab is present at a concentration of 5 mg/ml, wherein the buffering agent is histidine and the histidine is at a concentration of 10 mM, wherein the excipient is sucrose and the sucrose is at a concentration of 10% (w/v), wherein the PS80 is present at a concentration of 0.005% (w/v), and wherein the pharmaceutical formulation has a pH of about 6.0 or about 6.5. In some embodiments, the pH of the pharmaceutical formulation is about 6.5. In some embodiments, the isatuximab is present at a concentration of 20 mg/ml, wherein the buffering agent is histidine and the histidine is at a concentration of 20 mM, wherein the excipient is sucrose and the sucrose is present at a concentration of 10% (w/v), wherein the PS80 is present at a concentration of 0.02% (w/v), and wherein the pharmaceutical formulation has a pH of about 6.0. In some embodiments, the formulation is sterile.

Provided is a method of treating a human individual having multiple myeloma, comprising administering to the individual an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6), pomalidomide, and dexamethasone, wherein the treatment extends progression free survival (PFS) of the individual. In some embodiments, the method comprises administering the anti-CD38 antibody at a dose of 10 mg/kg, the pomalidomide at a dose of 4 mg, and the dexamethasone at a dose of 40 mg wherein the individual is under 75 years of age, or at a dose of 20 mg wherein the individual is 75 years of age or older. In some embodiments, the individual received at least two prior therapies for multiple myeloma. In some embodiments at least one of the at least two prior therapies for multiple myeloma was lenalidomide. In some embodiments, at least one of the two prior therapies was a proteasome inhibitor. In some embodiments, the treatment extends overall survival (OS) of the individual. In some embodiments, the treatment reverses renal function impairment in the individual.

Also provided is a method of treating a human individual having multiple myeloma, comprising administering to the individual an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6), pomalidomide, and dexamethasone, wherein the treatment extends overall survival (OS) of the individual. In some embodiments, the anti-CD38 antibody is administered at a dose of 10 mg/kg, the pomalidomide is administered at a dose of 4 mg, and the dexamethasone is administered at a dose of 40 mg wherein the individual is less than 75 years of age or at a dose of 20 mg wherein the individual is 75 years of age or older. In some embodiments, the individual received at least two prior therapies for multiple myeloma. In some embodiments at least one of the at least two prior therapies for multiple myeloma was lenalidomide. In some embodiments, at least one of the two prior therapies was a proteasome inhibitor. In some embodiments, the treatment reverses renal function impairment in the individual.

Provided is a method of improving renal impairment in a human individual with multiple myeloma, comprising administering to the individual an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6), pomalidomide, and dexamethasone. In some embodiments, the anti-CD38 antibody is administered at a dose of 10 mg/kg, the pomalidomide is administered at a dose of 4 mg, and the dexamethasone is administered at a dose of 40 mg wherein the individual is less than 75 years of age or at a dose of 20 mg wherein the individual is 75 years of age or older.

In some embodiments of the antibodies for use herein or the methods herein, the at least two prior therapies did not include treatment with an anti-CD38 antibody and/or treatment with pomalidomide. In some embodiments of the antibodies for use herein or the methods herein, the individual did not respond to at least one of the at least two prior therapies, or wherein the individual relapsed after at least one of the at least two prior therapies, or wherein the individual experienced disease progression during or after the treatment with at least one of the two prior therapies.

In some embodiments of the antibodies for use herein or the methods herein, the individual with multiple myeloma is selected for administration with the anti-CD38 antibody, the pomalidomide, and the dexamethasone based on the individual having renal impairment. In some embodiments of the antibodies for use herein or the methods herein, the individual with renal impairment has an estimated glomerular filtration rate (eGFR) less than about 60, less than about 50, or less than about 30 mL/min/1.73 m$^2$ prior to the start of treatment. In some embodiments of the antibodies for use herein or the methods herein, the individual with renal impairment has creatinine clearance of less than about 60, less than about 50, or less than about 30 mL/min/1.73 m$^2$ prior to the start of treatment. In some embodiments of the antibodies for use herein or the methods herein, the individual received at least two prior therapies for multiple myeloma. In some embodiments of the antibodies for use herein or the methods herein, at least one of the at least two prior therapies was lenalidomide. In some embodiments of the antibodies for use herein or the methods herein, at least one of the at least two prior therapies was a proteasome inhibitor. In some embodiments of the antibodies for use herein or the methods herein, the method extends progression free survival (PFS) of the individual. In some embodiments of the antibodies for use herein or the methods herein, the method extends overall survival (OS) of the individual.

Also provided herein is an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6) for use in treating multiple myeloma in an individual, the treatment comprising administering to the individual the anti-CD38 antibody, pomalidomide and dexamethasone, wherein the treatment extends progression free survival (PFS) and/or overall survival (OS). In some embodiments of the antibodies for use herein or the methods herein, the anti-CD38 antibody is administered at a dose of 10 mg/kg, the pomalidomide is administered at a dose of 4 mg, and the dexamethasone is administered at a dose of 40 mg wherein the individual is less than 75 years of age, or at a dose of 20 mg wherein the individual is 75 years of age or older. In some embodiments of the antibodies for use herein or the methods herein, the individual received at least two prior therapies for multiple myeloma. In some embodiments of the antibodies for use herein or the methods herein, at least one of the at least two prior therapies for multiple myeloma was lenalidomide. In some embodiments of the antibodies for use herein or the methods herein, at least one of the two prior therapies was a proteasome inhibitor.

Also provided is an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6) for use in reversing renal function impairment in an individual, the treatment comprising administering to the individual the anti-CD38 antibody, pomalidomide and dexamethasone. In some embodiments of the antibodies for use herein or the methods herein, the individual has multiple myeloma. In some embodiments of the antibodies for use herein or the methods herein, the individual is selected for administration with the anti-CD38 antibody, the pomalidomide, and the dexamethasone based on having renal impairment. In some embodiments of the antibodies for use herein or the methods herein, the individual has an estimated glomerular filtration rate (eGFR) of less than about 60, less than about 50, or less than about 30 mL/min/1.73 m² prior to the start of treatment. In some embodiments of the antibodies for use herein or the methods herein, the individual has a creatinine clearance of less than about 60, less than about 50, or less than about 30 mL/min/1.73 m² prior to the start of treatment. In some embodiments of the antibodies for use herein or the methods herein, the anti-CD38 antibody is administered at a dose of 10 mg/kg, the pomalidomide is administered at a dose of 4 mg, and the dexamethasone is administered at a dose of 40 mg wherein the individual is less than 75 years of age, or at a dose of 20 mg wherein the individual is 75 years of age or older. In some embodiments of the antibodies for use herein or the methods herein, the individual received at least two prior therapies for multiple myeloma. In some embodiments of the antibodies for use herein or the methods herein, at least one of the at least two prior therapies for multiple myeloma was lenalidomide. In some embodiments of the antibodies for use herein or the methods herein, at least one of the two prior therapies was a proteasome inhibitor.

In some embodiments, the antibodies for use herein or the methods herein extend the PFS of the individual by at least about 9 months. In some embodiments, the antibodies for use herein or the methods herein extend the PFS of the individual by about 11.53 months. In some embodiments, the antibodies for use herein or the methods herein extend the PFS of the individual by about 11.14 months. In some embodiments, the antibodies for use herein or the methods herein extend the PFS of the individual by at least about 4.5 months relative to an individual having multiple myeloma who received a treatment comprising pomalidomide and dexamethasone without the anti-CD38 antibody.

In some embodiments, an individual who receives treatment with an anti-CD38 antibody, pomalidomide, and dexamethasone, e.g., according to antibodies for use herein or the methods herein, achieves a response to the treatment faster than an individual having multiple myeloma who received a treatment comprising pomalidomide and dexamethasone, but without the anti-CD38 antibody. In some embodiments, the individual achieves a renal response to the treatment (e.g., treatment with an anti-CD38 antibody, pomalidomide, and dexamethasone, e.g., according to the antibodies for use herein or the methods herein) faster than an individual having multiple myeloma who received a treatment comprising pomalidomide and dexamethasone, but without the anti-CD38 antibody. In some embodiments, the renal response is a complete renal response. In some embodiments, the complete renal response is sustained for at least 60 days.

In some embodiments, the anti-CD38 antibody comprises a heavy chain variable region ($V_H$) comprising an amino acid sequence of SEQ ID NO: 7 and a light chain variable region ($V_L$) comprising an amino acid sequence of SEQ ID NO: 7 or SEQ ID NO: 9. In some embodiments, the anti-CD38 antibody is isatuximab.

In some embodiments, the anti-CD38 antibody, the pomalidomide, and the dexamethasone are administered in a first 28-day cycle, wherein, the anti-CD38 antibody is administered on Days 1, 8, 15, and 22 of the first 28-day cycle, the pomalidomide is administered on each of Days 1-21 of the first 28-day cycle, and the dexamethasone is administered on Days 1, 8, 15, and 22 of the first 28-day cycle. In some embodiments, the anti-CD38 antibody, the pomalidomide, and the dexamethasone are further administered in one or more 28-day cycles following the first 28-day cycle, wherein the anti-CD38 antibody is administered on Days 1 and 15 of the one or more 28-day cycles following the first 28-day cycle, the pomalidomide is administered on each of Days 1-21 of the one or more 28-day cycles following the first 28-day cycle, and the dexamethasone is administered on Days 1, 8, 15, and 22 of the one or more 28-day cycles following the first 28-day cycle. In some embodiments, the pomalidomide and the dexamethasone are administered prior to the anti-CD38 antibody on Day 1 of the first 28-day cycle. In some embodiments, the dexamethasone is administered prior to the anti-CD38 antibody Days 8, 15, and 22 of the first 28-day cycle, and wherein the anti-CD38 antibody is administered prior to the pomalidomide on Days 8 and 15 of the first 28-day cycle. In some embodiments, the pomalidomide and the dexamethasone are administered prior to the anti-CD38 antibody on Day 1 of the one or more 28-day cycles following the first 28-day cycle. In some embodiments, the dexamethasone is administered prior to the anti-CD38 antibody, and wherein the anti-CD38 antibody is administered prior to the pomalidomide on Day 15 of the one or more 28-day cycles following the first 28-day cycle. In some embodiments, the anti-CD38 antibody is administered intravenously. In some embodiments, the pomalidomide is administered orally. In some embodiments, the dexamethasone is administered orally. In some embodiments, the dexamethasone is administered intravenously.

In some embodiments, the anti-CD38 antibody, the pomalidomide, and the dexamethasone are administered in a first 28-day cycle. In some embodiments, the anti-CD38 antibody is administered once every week of the first 28-day cycle, the pomalidomide is administered for 21 days of the first 28-day cycle, and the dexamethasone is administered once every week of the first 28-day cycle. In some embodiments, the anti-CD38 antibody, the pomalidomide, and the dexamethasone are further administered in one or more 28-day cycles following the first 28-day cycle. In some embodiments, the anti-CD38 antibody is administered once every other week of the one or more 28-day cycles following the first 28-day cycle, the pomalidomide is administered for 21 days of the one or more 28-day cycles following the first 28-day cycle, and the dexamethasone is once every week of the one or more 28-day cycles following the first 28-day cycle. In some embodiments, the pomalidomide and the dexamethasone are administered prior to the anti-CD38 antibody in the first 28-day cycle. In some embodiments, the dexamethasone is administered prior to the anti-CD38 antibody and wherein the anti-CD38 antibody is administered prior to the pomalidomide in the first 28-day cycle. In some embodiments, the pomalidomide and the dexamethasone are administered prior to the anti-CD38 antibody in the one or more 28-day cycles following the first 28-day cycle. In some embodiments, the dexamethasone is administered prior to the anti-CD38 antibody, and wherein the anti-CD38 antibody is administered prior to the pomalidomide in the one or more 28-day cycles following the first 28-day cycle. In some embodiments, the anti-CD38 antibody is administered intravenously. In some embodiments, the pomalidomide is administered orally. In some embodiments, the dexamethasone is administered orally. In some embodiments, the dexamethasone is administered intravenously.

In some embodiments, the individual was refractory to the most recent prior therapy for multiple myeloma. In some embodiments, the most recent prior therapy was lenalidomide. In some embodiments, the most recent prior therapy was a proteasome inhibitor. In some embodiments according to any of antibodies for use herein or methods herein, the proteasome inhibitor is selected from the group consisting of: bortezomib, carfilzomib, and ixazomib. In some embodiments, the lenalidomide and the proteasome inhibitor were administered in combination.

In some embodiments, the individual has chronic obstructive pulmonary disorder (COPD). In some embodiments, the individual has asthma. In some embodiments, the individual has bronchospams. In some embodiments, the individual has not received prior therapy with pomalidomide. In some embodiments, the individual has not received prior therapy with an anti-CD38 antibody. In some embodiments, the individual has not received prior therapy with daratumumab. In some embodiments, the individual has one or more cytogenetic abnormalities selected from the group consisting of: del(17p), t(4;14), and t(14;16). In some embodiments, the individual is at least 65 but less than 75 years of age. In some embodiments, the individual is 75 years of age or older. In some embodiments, the individual has received at least three prior therapies for multiple myeloma. In some embodiments, the individual is East Asian (e.g., a Japanese individual, a Korean individual, or a Taiwanese individual). In some embodiments, the individual is Stage III according to the International Staging System (ISS). In some embodiments, the individual is Stage III according to the Revised International Staging System (R-ISS). In some embodiments, the individual is minimal residual disease (MRD) negative at a threshold of $10^{-4}$ or less after treatment (e.g., wherein "$10^{-4}$" means that in a patient bone marrow sample, there is less than 1 tumor cell per $10^4$ bone marrow cells), $10^{-5}$ or less after treatment (e.g., wherein "$10^{-5}$" means that in a patient bone marrow sample, there is less than 1 tumor cell per $10^5$ bone marrow cells), or $10^{-6}$ or less after treatment (e.g., wherein "$10^{-6}$" means that in a patient bone marrow sample, there is less than 1 tumor cell per $10^6$ bone marrow cells). In some embodiments, MRD is assessed via next generation sequencing (NGS). In some embodiments, MRD is assessed via next generation flow cytometry (NGF). Additionally or alternatively, in some embodiments, MRD is assessed via positron emission tomography-computed tomography (PET-CT) scan.

Provided is a kit comprising an anti-CD38 antibody for use in combination with pomalidomide and dexamethasone for treating an individual multiple myeloma according to a method or an antibodies for use provided herein.

Also provided are liquid pharmaceutical formulations comprising isatuximab. In some embodiments, a pharmaceutical formulation herein comprises isatuximab at a concentration of 5-20 mg/ml, a buffering agent selected from the group consisting of: histidine, acetate, and phosphate, and an excipient selected from the group consisting of: sucrose and mannitol, and a nonionic surfactant (such as polysorbate 20 (PS20), polysorbate 80 (PS80) or poloxamer 188), wherein the pH of the pharmaceutical formulation is between about 5.5 to about 7.4. In some embodiments, the pharmaceutical formulation comprises about 20 mM histidine, about 10% (w/v) sucrose, about 0.2% (w/v) polysorbate 80, and about 20 mg/ml isatuximab, wherein the pH of the pharmaceutical formulation is about 6.0.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 4:
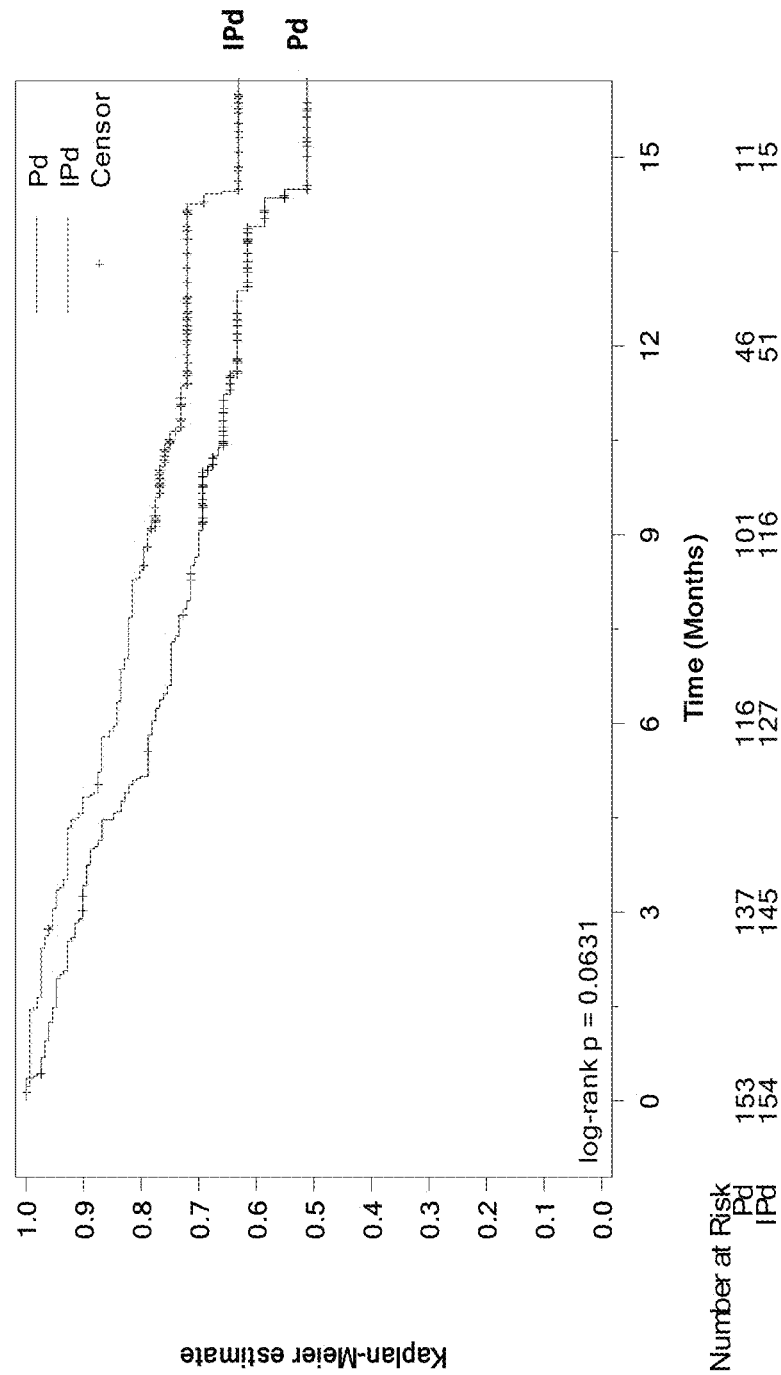

FIG. 4 provides a Kaplan-Meier Plot of overall survival (OS) of patients in the IPd arm (isatuximab+pomalidomide+dexamethasone) vs. the Pd arm (pomalidomide+dexamethasone).

Figure 5:
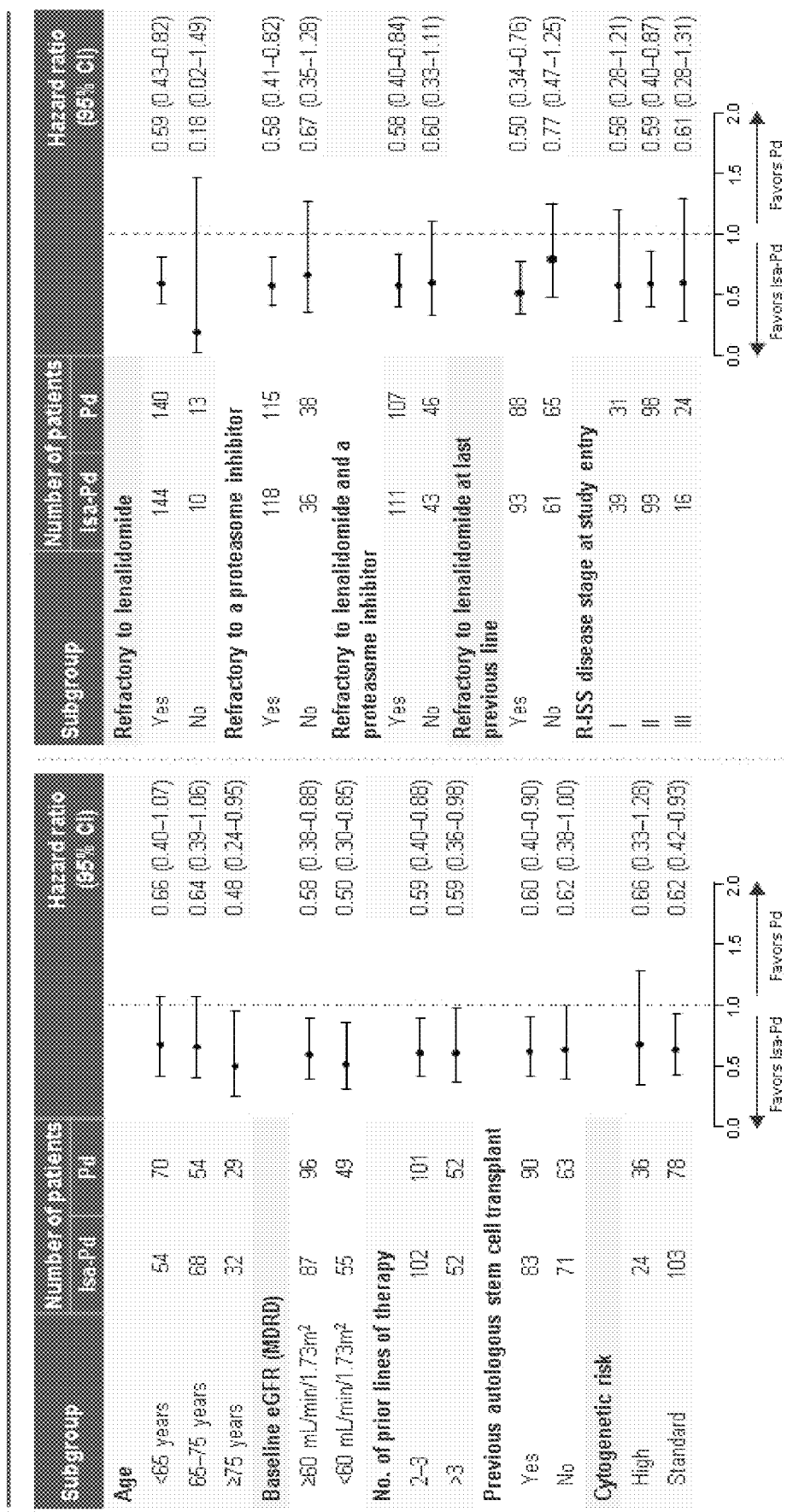

FIG. 5 provides a Forest Plot showing subgroup analyses of PFS in patients with various baseline characteristics (e.g., age, eGFR, prior lines of therapy, previous ASCT (autologous stem cell transplantation), cytogenetic risk factors, etc.) in the IPd arm vs. the PD arm.

Figure 6A:
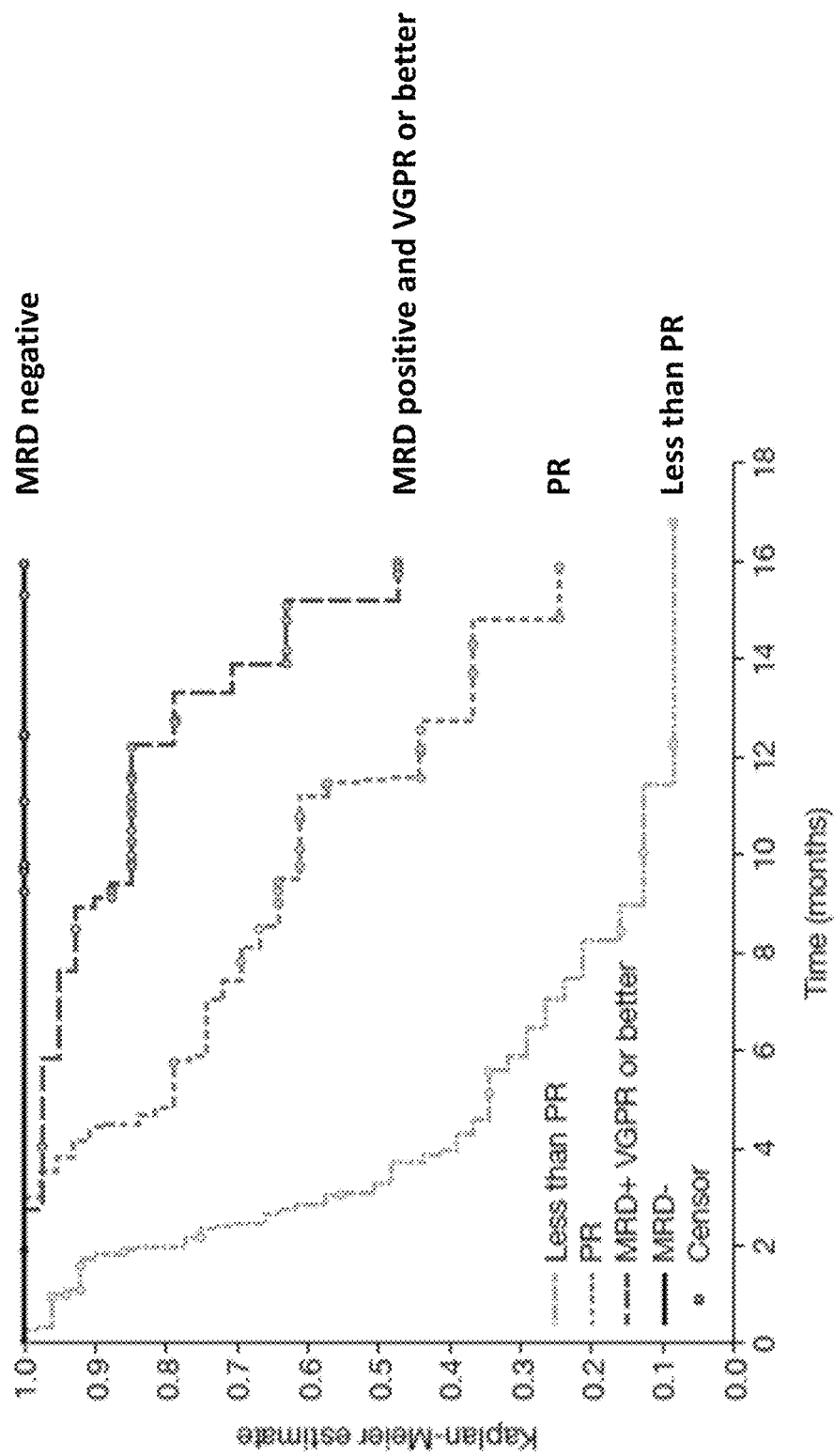

FIG. 6A provides a Kaplan-Meier Plot of progression-free survival (PFS) of patients in the IPd arm (isatuximab+pomalidomide+dexamethasone) who were minimal residual disease (MRD) negative, who were MRD positive but achieved VGPR or better, who achieved PR, or who achieved less than PR following the start of treatment.

Figure 6B:
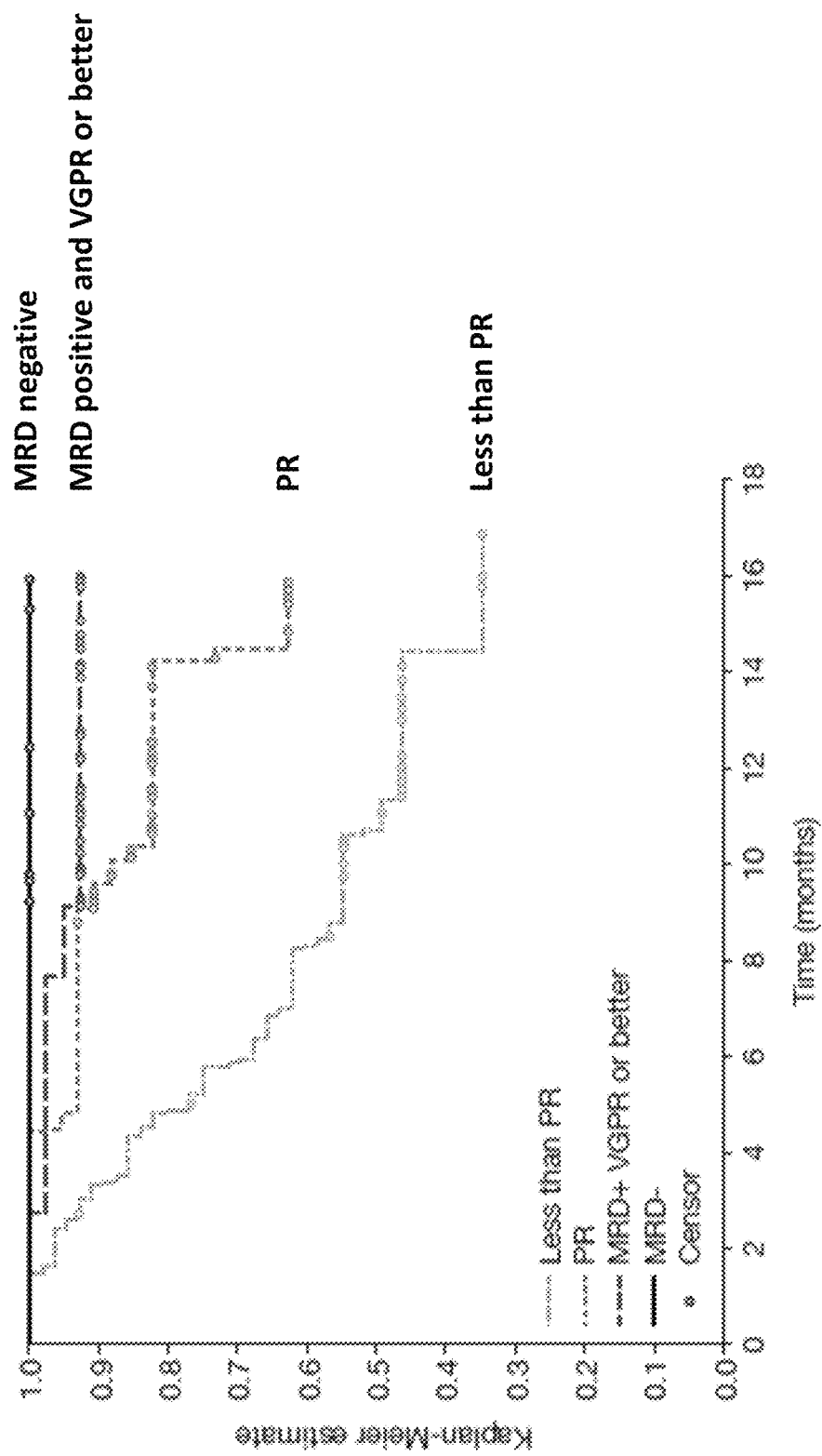

FIG. 6B provides a Kaplan-Meier Plot of overall survival (OS) of patients in the IPd arm (isatuximab+pomalidomide+dexamethasone) who were minimal residual disease (MRD) negative, who were MRD positive but achieved VGPR or better, who achieved PR, or who achieved less than PR following the start of treatment.

FIG. 7 shows the time to complete renal response (CRenal) and durable CRenal in patients with baseline eGFR<50 mL/min/1.73 m² in the Isa-Pd arm vs. the Pd arm. A durable CRenal (also known as "sustained CRenal") is a complete renal response that is sustained for at least 60 days.

DETAILED DESCRIPTION

Definitions

As used in this specification and the appended claims, the singular forms "a", "an" and "the" include plural referents unless the content clearly dictates otherwise. Thus, for example, reference to "a molecule" optionally includes a combination of two or more such molecules, and the like.

"Sustained response" refers to the sustained effect on preventing or delaying progression of a disease (e.g., multiple myeloma) and/or improving one or more response criteria after cessation of a treatment. For example, response to treatment for multiple myeloma may be measured according to the criteria in Kumar et al. (2016) "International Myeloma Working Group consensus criteria for response and minimal residual disease assessment in multiple myeloma." *Lancet Oncol.* 17(8): e328-e346) and Durie et al. (2006) "International uniform response criteria for multiple myeloma. *Leukemia.* 20: 1467-1473. (See also Table A below and Table B herein). In some embodiments, the sustained response has a duration at least the same as the treatment duration, e.g., at least 1.5×, 2.0×, 2.5×, or 3.0× length of the treatment duration.

TABLE A

| | Standard International Myeloma Working Group (IMWG) Response Criteria |
|---|---|
| Response | IMWG Criteria |
| Complete Response (CR) | negative immunofixation on the serum and urine, and disappearance of any soft tissue plasmacytomas, and <5% plasma cells in bone marrow aspirates. A normal FLC ratio of 0.26-1.65 is required. Two consecutive assessments are needed. No known evidence of progressive disease or new bone marrow lesions if radiographic studies were performed |

TABLE A-continued

| | Standard International Myeloma Working Group (IMWG) Response Criteria |
|---|---|
| Response | IMWG Criteria |
| Stringent Complete Response (sCR) | CR as defined above, plus: a normal free light chain (FLC) ratio of 0.26-1.65, and absence of clonal cells in bone marrow by immunohistochemistry (κ/λ ratio ≤4:1 or ≥1:2 for κ and λ patients, respectively, after counting ≥100 plasma cells). Two consecutive assessments of laboratory parameters are needed. No known evidence of progressive disease or new bone marrow lesions if radiographic studies were performed. |
| Very Good Partial Response (VGPR) | serum and urine M-protein detectable by immunofixation but not on electrophoresis, or ≥90% reduction in serum M-protein plus urine M-protein level <100 mg/24 h. Two consecutive assessments of laboratory parameters are needed. No known evidence of progressive disease or new bone marrow lesions if radiographic studies were performed. |
| Partial Response (PR) | ≥50% reduction of serum M-protein and reduction in 24 hours urinary M-protein by ≥90% or to <200 mg/24 h, and If present at baseline, a ≥50% reduction in the size (SPD‡) of soft tissue plasmacytomas is also required. Two consecutive assessments of laboratory parameters are needed. No known evidence of progressive disease or new bone marrow lesions if radiographic studies were performed. |
| Minimal Response (MR) | ≥25% but ≤49% reduction of serum M-protein and reduction in 24 hours urinary M-protein by 50-80%, which still exceed 200 mg/24 h, and If present at baseline, a ≥50% reduction in the size (SPD‡) of soft tissue plasmacytomas is also required. No known evidence of progressive disease or new bone marrow lesions if radiographic studies were performed. |
| Stable Disease (SD) | Not meeting criteria for CR, VGPR, PR, MR, or progressive disease. Two consecutive assessments are needed. No known evidence of progressive disease or new bone marrow lesions if radiographic studies were performed |
| Progressive Disease (PD) | Any one or more of the following criteria: Increase of ≥25% from lowest confirmed value in any one of the following criteria: Serum M-protein (the absolute increase must have been ≥0.5 g/dL). Serum M-protein increase ≥1 g/dL if the lowest M component was ≥5 g/dL. Urine M-component (the absolute increase must have been ≥200 mg/24 h). Appearance of new lesion(s), ≥50% increase from nadir in SPD‡ of >1 lesion, or ≥50% increase in the longest diameter of a previous lesion >1 cm in short axis; ≥50% increase in circulating plasma cells (minimum of 200 cells per μL) if this is the only measure of disease Two consecutive assessments are needed. No known evidence of progressive disease or new bone marrow lesions if radiographic studies were performed |

‡SPD, sum of the products of the maximal perpendicular diameters of measured lesions The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those that can reasonably be administered to a subject mammal to provide an effective dose of the active ingredient employed.

As used herein, the term "treatment" refers to clinical intervention designed to alter the natural course of the disease or cell (e.g., cancer cell) being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise, in order, the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs.

The term "Fc" as used herein refers to the sequence of a non-antigen-binding fragment that would result from digestion of an antibody or produced by other means, whether in monomeric or multimeric form, and can contain the hinge region. The original immunoglobulin source of the native Fc is preferably of human origin and can be any of the immunoglobulins. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, IgGA2, and IgG4). One example of a Fc is a disulfide-bonded dimer resulting from papain digestion of an IgG. The term "native Fc" as used herein is generic to the monomeric, dimeric, and multimeric forms.

As used herein, the term "overall response rate" or "ORR" refers to the proportion of patients with stringent complete response (sCR), complete response (CR), very good partial response (VGPR), and partial response (PR), as assessed by the IRC using the IMWG response criteria described in Kumar et al. (2016) "International Myeloma Working Group consensus criteria for response and minimal residual disease assessment in multiple myeloma." *Lancet Oncol.* 17(8): e328-e346 and Durie et al. (2006) "International uniform response criteria for multiple myeloma. *Leukemia.* 20: 1467-1473. See also Table A and Table B.

Overview

Provided herein are methods or antibodies for use for treating or delaying the progression of multiple myeloma in an individual who has received at least two prior therapies for multiple myeloma. The methods or antibodies for use provided herein comprise administering to the individual an effective amount of an anti-CD38 antibody (e.g., isatuximab), pomalidomide, and dexamethasone. In some embodiments, the treatment extends the progression free survival (PFS) and/or the overall survival (OS) of the individual. In some embodiments, the individual is negative for minimal residual disease (MRD) after treatment. In some embodiments, the treatment extends the progression free survival (PFS) and/or the overall survival (OS) of the individual, as compared to a treatment comprising administration of pomalidomide and dexamethasone without the anti-CD38 antibody (e.g., isatuximab). In some embodiments, the treatment improves renal function impairment. Also provided are methods or antibodies for use in improving renal impairment in an individual having multiple myeloma.

Anti-CD38 Antibodies

In some embodiments, the anti-CD38 antibody binds to human CD38. In some embodiments, the anti-CD38 antibody is a human antibody, a humanized antibody, or a chimeric antibody. In some embodiments, the anti-CD38 antibody comprises (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6). In some embodiments, the anti-CD38 antibody comprises a heavy chain variable domain ($V_H$) that comprises an amino acid sequence that is at least 90% identical (e.g., at least any one of 91%, 92%, 94%, 95%, 96%, 97%, 98%, or 99%, including any range between these values) to SEQ ID NO: 7. Additionally or alternatively, in some embodiments, the anti-CD38 antibody comprises a light chain variable domain ($V_L$) that comprises an amino acid sequence that is at least 90% identical (e.g., at least any one of 91%, 92%, 94%, 95%, 96%, 97%, 98%, or 99%, including any range between these values) to SEQ ID NO: 8 or SEQ ID NO: 9. In some embodiments, the anti-CD38 antibody comprises a $V_H$ that comprises SEQ ID NO: 7 and a $V_L$ that comprises SEQ ID NO: 8 or SEQ ID NO: 9.

```
                                          (SEQ ID NO: 7)
QVQLVQSGAE VAKPGTSVKL SCKASGYTFT DYWMQWVKQR
PGQGLEWIGT IYPGDGDTGY AQKFQGKATL TADKSSKTVY
MHLSSLASED SAVYYCARGD YYGSNSLDYW GQGTSVTVSS (SEQ ID NO: 8)
DIVMTQSHLS MSTSLGDPVS ITCKASQDVS TVVAWYQQKP
GQSPRRLIYS ASYRYIGVPD RFTGSGAGTD FTFTISSVQA
EDLAVYYCQQ HYSPPYTFGG GTKLEIKR (SEQ ID NO: 9)
DIVMAQSHLS MSTSLGDPVS ITCKASQDVS TVVAWYQQKP
GQSPRRLIYS ASYRYIGVPD RFTGSGAGTD FTFTISSVQA
EDLAVYYCQQ HYSPPYTFGG GTKLEIKR
```

In some embodiments, the anti-CD38 antibody is isatuximab (CAS Registry Number: 1461640-62-9). Isatuximab, also known as hu38SB19 and SAR650984, is an anti-CD38 antibody described in WO 2008/047242 and U.S. Pat. No. 8,153,765, the contents of both of which are incorporated by reference herein in their entirety.

The heavy chain of isatuximab comprises the amino acid sequence:

```
                                          (SEQ ID NO: 10)
QVQLVQSGAE VAKPGTSVKL SCKASGYTFT DYWMQWVKQR

PGQGLEWIGT IYPGDGDTGY AQKFQGKATL TADKSSKTVY

MHLSSLASED SAVYYCARGD YYGSNSLDYW GQGTSVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LIKNQVSLIC LVKGFYPSDI AVEWESNGQP ENNYKTTPPV

LDSDGSFFLY SKLTVDKSRW QQGNVFSCSV MHEALHNHYT

QKSLSLSPG
``` and the light chain of isatuximab comprises the amino acid sequence:

```
                                          (SEQ ID NO: 11)
DIVMTQSHLS MSTSLGDPVS ITCKASQDVS TVVAWYQQKP

GQSPRRLIYS ASYRYIGVPD RFTGSGAGTD FTFTISSVQA

EDLAVYYCQQ HYSPPYTFGG GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The anti-CD38 antibodies may be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. The vector is typically transformed into a host cell suitable for expression of the nucleic acid. In some embodiments, the host cell is a eukaryotic cell or a prokaryotic cell. In some embodiments, the eukaryotic host cell is a mammalian cell. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268. The anti-CD38 antibody prepared from the cells can be purified using, for example, hydroxylapatite chromatography, hydrophobic interaction chromatography, gel electrophoresis, dialysis, and affinity chromatography, with affinity chromatography being among one of the typically preferred purification steps. In general, various methodologies for preparing antibodies for use in research, testing, and clinical applications are well-established in the art, consistent with the above-described methodologies and/or as deemed appropriate by one skilled in the art.

Pomalidomide

The chemical name for pomalidomide is 4-amino-2-(2,6-dioxopiperidin-3-yl)isoindoline-1,3-dione, and pomalidomide has the following chemical structure

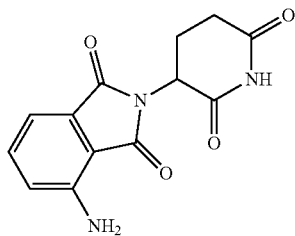 [SMILES: Nc1cccc2c1C(=O)N(C1CCC(=O)NC1=O)C2=O]

Pomalidomide has molecular formula of $C_{13}H_{11}N_3O_4$ and a molecular weight of 273.24 g/mol. Pomalidomide is commercially available as POMALYST, POMALID, IMNOVID, and others.

Dexamethasone

The chemical name for dexamethasone is 1-dehydro-16alpha-methyl-9alpha-fluorohydrocortisone, and dexamethasone has the following chemical structure:

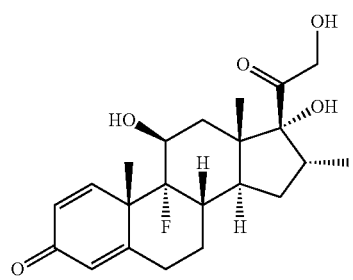

Dexamethasone has molecular formula of $C_{22}H_{29}FO_5$ and a molecular weight of 392.461 g/mol. Dexamethasone is commercially available as formulations for oral and intravenous administration. Exemplary trade names for dexamethasone include, e.g., DECADRON, MAXIDEX, HEXADROL, DEXACORT, DEXASONE, ORADEXON, SUPERPREDNOL, DEXALONA and others.

Pharmaceutical Compositions and Formulations

Also provided herein are pharmaceutical compositions and formulations, e.g., for the treatment of multiple myeloma (such as refractory multiple myeloma or relapsed and refractory multiple myeloma) comprising an anti-CD38 antibody (such as isatuximab), pomalidomide, or dexamethasone. In some embodiments, each of the anti-CD38 antibody (e.g., isatuximab), the pomalidomide, and the dexamethasone is provided as a separate pharmaceutical composition. In some embodiments, the pharmaceutical compositions and formulations further comprise a pharmaceutically acceptable carrier and/or pharmaceutically acceptable excipient. Suitable excipients, including nonionic surfactants such as PS80, are described in Pharmacopoeia from US and EP (USP and PhEu, respectively) and in the 2015 Chinese Pharmacopoeia (ChP, which describes Polysorbate 80, for Injection, for example).

In some embodiments, the pharmaceutical formulations provided herein comprise isatuximab at a concentration of 5-20 mg/ml, a buffering agent selected from the group consisting of: histidine, acetate, and phosphate, and an excipient selected from the group consisting of sucrose and mannitol, and 0.001%-0.03% of a nonionic surfactant (such as PS20, PS80 or poloxamer 188), wherein the pH of the pharmaceutical formulation is between about 5.5 to about 7.4. In some embodiments, the pharmaceutical formulation comprises 5 mg/ml isatuximab, 10 mM histidine or 10 mM acetate, 10% (w/v) sucrose or 5% mannitol, and 0.001, 0.005%, or 0.01% (w/v) nonionic surfactant, wherein the pH of the pharmaceutical formulations is about 6.0 or about 6.5. In some embodiments, the pharmaceutical formulation comprises 5 mg/ml isatuximab, 10 mM histidine, 10% (w/v) sucrose, and 0.005% (w/v) PS80, and the pH of the pharmaceutical formulation is about 6.0 or about 6.5. In some embodiments, the nonionic surfactant is PS80.

In some embodiments, an anti-CD38 antibody described herein (such as isatuximab) is in a pharmaceutical formulation comprising about 20 mg/mL antibody, about 20 mM histidine, about 10% (w/v) sucrose, and about 0.02% (w/v) nonionic surfactant (such as PS20, PS80 or poloxamer 188), wherein the pH of the pharmaceutical formulation is about 6.0. In some embodiments, an anti-CD38 antibody described herein (such as isatuximab) is in a pharmaceutical formulation comprising about 20 mg/mL antibody, about 100 mg/mL sucrose, 2.22 mg/mL histidine hydrochloride monohydrate, about 1.46 mg/ml histidine, and about 0.2 mg/ml nonionic surfactant. In some embodiments, the nonionic surfactant is PS80.

In some embodiments, the pharmaceutical formulation comprises water for injection (WFI), such as sterile water for injection (SWFI). In some embodiments, the pharmaceutical formulation is sterile. In some embodiments, a single use of the formulation comprises 5 ml of the pharmaceutical formulation (i.e., 100 mg anti-CD38 antibody). In some embodiments, the single use 5 ml pharmaceutical formulation is provided in, e.g., a type I 6 mL colorless clear glass vial fitted with elastomeric closure. In some embodiments, the fill volume of the vial has been established to ensure removal of 5 mL. In some embodiments, the fill volume is 5.4 mL. In some embodiments, a single use of the formulation comprises 25 ml of the pharmaceutical formulation (i.e., 500 mg anti-CD38 antibody). In some embodiments, the single use 25 ml pharmaceutical formulation is provided in, e.g., a 30 mL colorless clear glass vial fitted with elastomeric closure. In some embodiments, the fill volume of the vial has been established to ensure removal of 25 mL. In some embodiments, the pharmaceutical formulation is stable for at least about 6, 12, 18, 24, 30, or 36 months, including any range in between these values, at a temperature between about 2° C. and about 8° C. and protected from light. In some embodiments, the pharmaceutical formulation is diluted for infusion in 0.9% sodium chloride or 5% dextrose. In some embodiments, the diluted infusion solution is stable for up to about 6, 12, 18, 24, 30, 36, 42, or 48 hours, including any range in between these values, between about 2° C. and about 8° C. In some embodiments, the diluted solution for infusion is stable following storage between about 2° C. and about 8° C. for a further 8 hours (e.g., including the infusion time) at room temperature. In some embodiments, the diluted solution for infusion is stable in the presence of light. In some embodiments the bag in which the diluted solution for infusion is diluted is fabricated from polyolefins (PO), polyethylene (PE), polypropylene (PP), polyvinyl chloride (PVC) with di(ethylhexyl)phthalate (DEHP) or ethylene-vinyl acetate (EVA). In some embodiments, the tubing used for infusion is fabricated from PE, PVC (with or without DEHP), polybutyldiene (PBD), or polyurethane (PU) with an in-line filter (polyethersulfone (PES), polysulfone or nylon).

Pharmaceutical formulations of pomalidomide and dexamethasone are commercially available. For example, pomalidomide is known under a variety of trade names (as described elsewhere herein) including POMALYST®. Dexamethasone is known under a variety of trade names (as described elsewhere herein), including DECADRON, MAXIDEX, and HEXADROL. In some embodiments, the pomalidomide and/or the dexamethasone are provided in separate containers. In some embodiments, the pomalidomide and/or the dexamethasone are each used and/or prepared for administration to an individual as described in the prescribing information available with the commercially available product.

Methods of Treatment and Antibodies for Use in Treating

Provided herein are methods and antibodies for use in treating or delaying progression of multiple myeloma (such as relapsed multiple myeloma or relapsed and refractory multiple myeloma) in an individual (e.g., a human individual) comprising administering to the individual an effective amount of an anti-CD38 antibody (e.g., an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6)), pomalidomide, and dexamethasone, wherein individual received at least two prior therapies for multiple myeloma (e.g., lenalidomide and a proteasome inhibitor). In some embodiments, the administration of the anti-CD38 antibody, pomalidomide, and dexamethasone as described herein results in a sustained response in the individual. In some embodiments, administration of the anti-CD38 antibody, pomalidomide, and dexamethasone as described herein extends the progression free survival (PFS) of the individual. In some embodiments, administration of the anti-CD38 antibody, pomalidomide, and dexamethasone as described herein extends the overall survival (OS) of the individual. In some embodiments, administration of the anti-CD38 antibody, pomalidomide, and dexamethasone as described herein results in lower minimal residual disease (MRD). In some embodiments the individual is MRD negative following administration of the anti-CD38 antibody, pomalidomide, and dexamethasone as described herein. In some embodiments, prior to administration of the anti-CD38 antibody, pomalidomide, and dexamethasone as described herein, the individual demonstrates renal function impairment. In some embodiments, administration of the anti-CD38 antibody, pomalidomide, and dexamethasone as described herein improves renal function in the individual. In some embodiments, the individual is an adult, e.g., at least 18 years of age.

Provided herein are methods or antibodies for use in improving renal impairment in an individual (e.g., a human individual) with multiple myeloma, comprising administering to the individual an effective amount of an anti-CD38 antibody comprising (a) a heavy chain variable domain ($V_H$) that comprises: a CDR-H1 comprising the amino acid sequence DYWMQ (SEQ ID NO: 1), a CDR-H2 comprising the amino acid sequence TIYPGDGDTGYAQKFQG (SEQ ID NO: 2), and a CDR-H3 comprising the amino acid sequence GDYYGSNSLDY (SEQ ID NO: 3), and (b) a light chain variable domain ($V_L$) that comprises: a CDR-L1 comprising the amino acid sequence KASQDVSTVVA (SEQ ID NO: 4), a CDR-L2 comprising the amino acid sequence SASYRYI (SEQ ID NO: 5), and a CDR-L3 comprising the amino acid sequence QQHYSPPYT (SEQ ID NO: 6), pomalidomide, and dexamethasone. In some embodiments, the individual with multiple myeloma is selected for administration with the anti-CD38 antibody, pomalidomide, and dexamethasone based on having renal impairment. In some embodiments, the individual with multiple myeloma and renal impairment has poor prognosis. In some embodiments, the individual is an adult, e.g., at least 18 years of age. In some embodiments, the individual has renal impairment if the individual has an estimated glomerular filtration rate (eGFR) of less than about 90 mL/min/1.73 m$^2$ prior to the start of treatment. In some embodiments, the individual has renal impairment if the individual has an estimated glomerular filtration rate (eGFR) of between about 60 mL/min/1.73 m$^2$ and less than about 90 mL/min/1.73 m$^2$ prior to the start of treatment. In some embodiments, an individual with an eGFR of between about 60 mL/min/1.73 m$^2$ and less than about 90 mL/min/1.73 m$^2$ prior to the start of treatment has mild renal impairment. In some embodiments, the individual has renal impairment if the individual has an estimated glomerular filtration rate (eGFR) of between about 30 mL/min/1.73 m² and less than about 60 mL/min/1.73 m² prior to the start of treatment. In some embodiments, an individual with an eGFR of between about 30 mL/min/1.73 m² and less than about 60 mL/min/1.73 m² (e.g., such as less than about 30, less than about 50, or less than about 60 mL/min/1.73 m²) prior to the start of treatment has moderate renal impairment. In some embodiments, the individual has renal impairment if the individual has an estimated glomerular filtration rate (eGFR) of less than about 30 mL/min/1.73 m² prior to the start of treatment. In some embodiments, an individual with an eGFR of less than about 30 mL/min/1.73 m² prior to the start of treatment has severe renal impairment. In some embodiments, the individual has renal impairment if the individual has creatinine clearance of less than about 90 mL/min/1.73 m² prior to the start of treatment. In some embodiments, the individual has renal impairment if the individual has creatinine clearance of between about 60 mL/min/1.73 m² and less than about 90 mL/min/1.73 m² prior to the start of treatment. In some embodiments, an individual with creatinine clearance of between about 60 mL/min/1.73 m² and less than about 90 mL/min/1.73 m² prior to the start of treatment has mild renal impairment. In some embodiments, the individual has renal impairment if the individual has creatinine clearance of between about 30 mL/min/1.73 m² and less than about 60 mL/min/1.73 m² prior to the start of treatment. In some embodiments, an individual with creatinine clearance of between about 30 mL/min/1.73 m² and less than about 60 mL/min/1.73 m² (e.g., such as less than about 50 or less than about 60 mL/min/1.73 m²) prior to the start of treatment has moderate renal impairment. In some embodiments, the individual has renal impairment if the individual has creatinine clearance of less than about 30 mL/min/1.73 m² prior to the start of treatment. In some embodiments, an individual with creatinine clearance of less than about 30 mL/min/1.73 m² prior to the start of treatment has severe renal impairment. In some embodiments, the individual achieves a renal response following the start of treatment with the anti-CD38 antibody, pomalidomide, and dexamethasone. In some embodiments the individual achieves a complete renal response following the start of treatment with the anti-CD38 antibody, pomalidomide, and dexamethasone. In some embodiments, a complete renal response is characterized as an improvement of baseline eGFR or creatinine clearance from <50 mL/min/1.73 m² prior to the start of treatment to ≥60 mL/min/1.73 m² at least one assessment during treatment. In some embodiments the individual achieves a sustained complete renal response following the start of treatment. A sustained complete renal response is also known as a "durable complete renal response." In some embodiments, a sustained complete renal response (or "durable complete renal response) is characterized as an improvement of baseline eGFR or creatinine clearance from <50 mL/min/1.73 m² prior to the start of treatment to ≥60 mL/min/1.73 m² that is sustained for at least about 60 days. In some embodiments the time to first renal response in an individual receiving treatment with the anti-CD38 antibody, pomalidomide, and dexamethasone is shorter than the time to first renal response in individual receiving treatment with pomalidomide and dexamethasone. In some embodiments, "time to renal first response" refers to the duration of time between the date of the first dose of the treatment with the anti-CD38 antibody, pomalidomide, and dexamethasone and the date of the first sign of renal response. In some embodiments, the time to complete renal response in an individual receiving treatment with the anti-CD38 antibody, pomalidomide, and dexamethasone is about any one of 8, 8.5, 9, 9.5, 10, 10.5, 11, 11.5, 12, 12.5, 13, 13.5, 14, 14.5, 15, 15.5, or 16 weeks from the start of treatment, including any range in between these values. In some embodiments, the time to complete renal response in an individual receiving treatment with the anti-CD38 antibody, pomalidomide, and dexamethasone is about any one of 1, 1.5, 2, 2.5, 3, 3.5, 3.6, 3.7, 3.8, 3.9, or 4 weeks less than the time to complete renal response in an individual receiving treatment with pomalidomide and dexamethasone, but without the anti-CD38 antibody, including any range in between these values. In some embodiments, the time to sustained complete renal response (also known as "durable complete renal response") in an individual receiving treatment with the anti-CD38 antibody, pomalidomide, and dexamethasone is about any one of 1, 1.5, 2, 2.1, 2.2, 2.3, 2.4, 2.5, 2.6, 2.7, 2.8, 2.9, or 3 weeks from the start of treatment, including any range in between these values. In some embodiments, the time to complete renal response in an individual receiving treatment with the anti-CD38 antibody, pomalidomide, and dexamethasone is about 1, 1.5, 2, 2.1, 2.2, 2.3, 2.4, 2.5, 2.6, 2.7, 2.8, 2.9, or 3 weeks less, including any range between these values, than the time to complete renal response in an individual receiving treatment with pomalidomide and dexamethasone, but without the anti-CD38 antibody.

In some embodiments, treatment with the anti-CD38 antibody, pomalidomide, and dexamethasone according to a method or an antibody for use provided herein prevents or delays end-stage renal disease (ESRD) in the individual. In some embodiments, an individual receiving treatment with the anti-CD38 antibody, pomalidomide, and dexamethasone has a lower probability of developing ESRD than an individual receiving treatment with pomalidomide and dexamethasone, but without the anti-CD38 antibody. In some embodiments, ESRD in an individual receiving treatment with the anti-CD38 antibody, pomalidomide, and dexamethasone according to a method or an antibody for use provided herein is delayed by at least about any one of 1, 2, 3, or 4 weeks; by at least about any one of 2, 3, 4, 5, 6, 7, 8, 9, 10, 11, 12, 18, 24, 30, 36, 42, or 48 months; or longer than 48 months (e.g., such as about any one of 4.5, 5, 5.5, or 6 years), including any range between these values, as compared to an individual receiving treatment with pomalidomide and dexamethasone, but without the anti-CD38 antibody.

In some embodiments, the methods or antibodies for use provided herein extend the progression free survival (PFS) of the individual. In some embodiments, the methods or antibodies for use provided herein extend the overall survival (OS) of the individual. In some embodiments, the individual is negative for minimal residual disease (MRD) following treatment (e.g., treatment with the anti-CD38 antibody, the pomalidomide, and the dexamethasone). In some embodiments, the individual has received at least two prior therapies (or prior lines of therapy) for multiple myeloma (e.g., such as lenalidomide and a proteasome inhibitor).

In some embodiments, the individual demonstrated progressive disease during the most recent prior therapy (or line of therapy), e.g., the therapy (or line of therapy) just before the start of treatment with the anti-CD38 antibody, pomalidomide, and dexamethasone. In some embodiments, the individual demonstrated progressive disease (PD) within 60 days after the end of the most recent prior therapy (or line of therapy) for multiple myeloma, e.g., the therapy (or line of therapy) just before the start of treatment with the anti-CD38 antibody, pomalidomide, and dexamethasone. In some embodiments, a progressive disease (PD) is defined according to International Myeloma Working Group criteria (see, e.g., Kumar et al. (2016) "International Myeloma Working Group consensus criteria for response and minimal residual disease assessment in multiple myeloma." *Lancet Oncol.* 17(8):e328-e346; Durie et al. (2006) "International uniform response criteria for multiple myeloma. *Leukemia.* 20: 1467-1473; and Table A and Table B herein). In some embodiments, a line of therapy is ≥1 complete cycle of a single agent, or of a combination of two or more agents, or a planned sequential therapy that includes stem cell transplantation. In some embodiments, a given treatment is considered a new line of therapy if a new line of treatment is started after discontinuation of a previous line. In some embodiments, a treatment is considered a new line of therapy if a treatment regimen is discontinued for any reason and a different treatment regimen is started. In some embodiments, a treatment regimen is considered to have been discontinued if all the drugs in that given regimen have been stopped. In some embodiments, a regimen is not considered to have been discontinued if some of the drugs of the regimen, but not all, have been discontinued. In some embodiments, the reasons for discontinuation, addition, substitution, or SCT (stem cell transplant) do not influence how lines are counted. In some embodiments, a given treatment is considered a new line of therapy if there has been an unplanned addition or substitution of 1 or more drugs in an existing regimen. In some embodiments, in individuals undergoing >1 SCT, except in the case of a planned tandem SCT with a predefined interval (such as 3 months), each SCT (autologous or allogeneic) can be considered a new line of therapy regardless of whether the conditioning regimen used is the same or different. In some embodiments, planned tandem SCT is considered 1 line. In some embodiments, planned induction and/or consolidation, maintenance with any SCT (frontline, relapse, autologous or allogeneic) is considered 1 line of therapy.

In some embodiments, the multiple myeloma is difficult to treat. In some embodiments, the individual has refractory multiple myeloma. In some embodiments, an individual with refractory multiple myeloma is one who was refractory to all prior therapies (or prior lines of therapy), but achieved at least a minimal response (MR) to one prior therapy (or line of therapy). In some embodiments, a minimal response (MR) is defined according to International Myeloma Working Group criteria (see, e.g., Kumar et al. (2016) "International Myeloma Working Group consensus criteria for response and minimal residual disease assessment in multiple myeloma." *Lancet Oncol.* 17(8):e328-e346; Durie et al. (2006) "International uniform response criteria for multiple myeloma. *Leukemia.* 20: 1467-1473; and Table A and Table B herein). In some embodiments, an individual with refractory multiple myeloma is one who was non-responsive to a prior therapy (or prior line of therapy). In some embodiments, "non-responsive" to a therapy (or line of therapy) for multiple myeloma means that the individual failed to achieve at least a minimal response (MR) to the therapy (or line of therapy) for multiple myeloma. In some embodiments "non-responsive" to a therapy (or line of therapy) for multiple myeloma means that the individual has demonstrated progressive disease during the therapy (or line of therapy) for multiple myeloma. In some embodiments, an individual with refractory multiple myeloma is one who demonstrated progressive disease within the 60 days from the end of the last therapy for multiple myeloma.

In some embodiments, the individual has failed prior treatment (such as treatment with lenalidomide and/or a proteasome inhibitor) for multiple myeloma. In some embodiments, "failing" a prior treatment means that the individual has demonstrated disease progression (e.g., according to the criteria in Table A and Table B) while on the treatment (such as treatment with lenalidomide and/or a proteasome inhibitor) or within 60 days from end of treatment (such as treatment with lenalidomide and/or a proteasome inhibitor). In some embodiments, "failing" a prior treatment for multiple myeloma means that the individual had demonstrated a partial response (PR) or better (e.g., according to the criteria in Table A and Table B) to treatment (such as treatment with lenalidomide and/or a proteasome inhibitor), but exhibited disease progression within 6 months after discontinuing the treatment (e.g., as treatment with lenalidomide and/or a proteasome inhibitor). In some embodiments, "failing" a prior treatment for multiple myeloma means that the individual developed toxicity/intolerance after a minimum of 2 consecutive cycles of a treatment regimen (e.g., a treatment regimen containing lenalidomide and/or a proteasome inhibitor (bortezomib, carfilzomib, ixazomib, marizomib, oprozomib, etc.)). In some embodiments, intolerance to a proteasome-containing regimen means that the individual (e.g., an individual who did not have peripheral neuropathy prior to starting the regimen) developing peripheral neuropathy or neuropathic pain, e.g., during or following treatment with a proteasome-containing regimen. In some embodiments, intolerance to a lenalidomide-containing regimen means that the individual developed severe rash during or following treatment with a lenalidomide-containing regimen.

In some embodiments, the individual has relapsed and refractory multiple myeloma. In some embodiments, the individual has measurable disease according to one or more of the following criteria: serum M protein ≥0.5 g/dL measured using serum protein immunoelectrophoresis and/or urine M protein ≥200 mg/24 hours measured using urine protein immunoelectrophoresis and/or serum free light chain (FLC) (i.e., FLC assay ≥10 mg/dl (≥100 mg/L) and an abnormal serum FLC ratio (<0.26 or >1.65). In some embodiments, an individual with relapsed and refractory multiple myeloma is one who relapsed from at least one prior therapy (or line of therapy) for multiple myeloma and was refractory to the most recent therapy (or line of therapy) for multiple myeloma. In some embodiments, the individual with relapsed and refractory multiple myeloma is one who relapsed from at least one prior therapy (or line of therapy) for multiple myeloma, was refractory to the most recent therapy (or line of therapy) for multiple myeloma, and was refractory to one or more therapies (or lines of therapy) prior to the most recent therapy (or line of therapy) for multiple myeloma. In some embodiments, an individual with relapsed or refractory multiple myeloma is one who demonstrated progressive disease within 60 days after the end of the most recent therapy (or line of therapy).

In some embodiments, the individual was refractory to the most recent prior therapy (or line of therapy).

In some embodiments, the individual has relapsed/refractory multiple myeloma (RRMM) with measurable disease (e.g., serum M protein ≥0.5 g/dL measured using serum protein immunoelectrophoresis and/or urine M protein ≥200 mg/24 hours measured using urine protein immunoelectrophoresis) who has received at least 2 prior therapies, including lenalidomide and a proteasome inhibitor (e.g., bortezomib, carfilzomib, ixazomib, marizomib, oprozomib, etc.) and was refractory to the last line of therapy (i.e., most recent line of therapy). In some embodiments, the individual has adequate renal, hepatic and bone marrow function.

In some embodiments, the individual has a poor prognosis. In some embodiments of the methods or antibodies for use provided herein, the individual has received at least one, at least two, at least three, at least four prior therapies (or prior lines of therapy), or more than four prior therapies (or prior lines of therapy), e.g., at least any one of 5, 6, 7, 8, 9, 10, or 11 prior therapies (or prior lines of therapy) for multiple myeloma.

In some embodiments, the individual has undergone at least one prior therapy (or prior line of therapy) with lenalidomide. In some embodiments, the prior lenalidomide therapy (or prior line of lenalidomide therapy) comprised at least two consecutive cycles of lenalidomide. In some embodiments, the individual failed (e.g., was non-responsive to) a prior lenalidomide therapy (or a prior line of lenalidomide therapy). In some embodiments, an individual who failed a prior lenalidomide therapy (or a prior line of lenalidomide therapy) did not achieve at least a minimal response (MR) during the therapy (or line of therapy) with lenalidomide. In some embodiments, an individual who failed a prior lenalidomide therapy (or a prior line of lenalidomide therapy) demonstrated progressive disease (PD) during the therapy (or line of therapy) with lenalidomide. As noted elsewhere herein, in some embodiments, "minimal response" and "progressive disease" are assessed according to the criteria in Kumar et al. (2016) "International Myeloma Working Group consensus criteria for response and minimal residual disease assessment in multiple myeloma." *Lancet Oncol.* 17(8): e328-e346 and Durie et al. (2006) "International uniform response criteria for multiple myeloma. *Leukemia.* 20: 1467-1473 (see also TableA and Table B herein). In some embodiments, prior lenalidomide was administered during the first, second, third, fourth, fifth, sixth, and/or later therapy (or line of therapy) for multiple myeloma (i. e., prior to treatment with an anti-CD38 antibody, pomalidomide, and dexamethasone according to a method or an antibody for use provided herein). In some embodiments, the individual was refractory to lenalidomide. In some embodiments, the prior lenalidomide was administered to the individual as a single agent. In some embodiments, the prior lenalidomide was administered to the individual in conjunction with at least one additional agent.

In some embodiments, the individual has undergone at least one prior therapy (or at least one prior line of therapy) with a proteasome inhibitor (PI). In some embodiments, the proteasome inhibitor is selected from the group consisting of: bortezomib, carfilzomib, ixazomib, marizomib, and oprozomib. In some embodiments, the prior therapy (or prior line of therapy) with the proteasome inhibitor comprised at least two consecutive cycles of the proteasome inhibitor. In some embodiments, the individual failed (e.g., was non-responsive to) a prior proteasome inhibitor therapy (or a prior line of proteasome inhibitor therapy). In some embodiments, an individual who failed a prior therapy (or a line of therapy) with the proteasome inhibitor did not achieve at least a minimal response (MR) during the therapy (or line of therapy) with the proteasome inhibitor. In some embodiments, an individual who failed a prior therapy (or a prior line of therapy) with a proteasome inhibitor demonstrated progressive disease (PD) during the therapy (or prior line of therapy) with the proteasome inhibitor. In some embodiments, the prior proteasome inhibitor therapy was administered during the first, second, third, fourth, fifth, sixth, and/or later therapy (or line of therapy) for multiple myeloma (i. e., prior to treatment with an anti-CD38 antibody, pomalidomide, and dexamethasone according to methods or antibodies for use provided herein). In some embodiments, the individual was refractory to the proteasome inhibitor (e.g., one or more proteasome inhibitors). In some embodiments, the prior proteasome inhibitor therapy (or prior line of proteasome inhibitor therapy) was administered to the individual as a single agent. In some embodiments, the prior proteasome inhibitor therapy (or prior line of proteasome inhibitor therapy) was administered to the individual in conjunction with at least one additional agent.

In some embodiments, the lenalidomide and the proteasome inhibitor were administered to the individual in combination. In some embodiments, the individual previously achieved a partial response (PR) or greater to lenalidomide and/or the proteasome inhibitor (e.g., given alone or in combination), but demonstrated progressive disease (PD) within 6 months of the end of the therapy (or end of the line of therapy) with lenalidomide and/or the proteasome inhibitor.

In some embodiments, the individual is East Asian. In some embodiments, the East Asian individual is a Japanese individual, a Korean individual, or a Taiwanese individual.

In some embodiments, the individual has chronic obstructive pulmonary disorder (COPD). In some embodiments, the individual is diagnosed with COPD prior to the start of treatment with the anti-CD38 antibody, pomalidomide, and dexamethasone. In some embodiments, the individual develops and/or is diagnosed with COPD after the start of treatment with the anti-CD38 antibody, pomalidomide, and dexamethasone.

In some embodiments, the individual has asthma. In some embodiments, the individual is diagnosed with asthma prior to the start of treatment with the anti-CD38 antibody, pomalidomide, and dexamethasone. In some embodiments, the individual develops and/or is diagnosed with asthma after the start of treatment with the anti-CD38 antibody, pomalidomide, and dexamethasone In some embodiments, the individual has (e.g., experiences) bronchospasms. In some embodiments, the individual experienced bronchospasms prior to the start of treatment with the anti-CD38 antibody, pomalidomide, and dexamethasone. In some embodiments, the individual develops bronchospasms after the start of treatment with the anti-CD38 antibody, pomalidomide, and dexamethasone.

In some embodiments, the bone marrow plasma cells of an individual receiving treatment according to methods or antibodies for use provided herein have a CD38 receptor density of between about 13000 and about 340000 receptors/cancer cell. In some embodiments, the individual receiving treatment according to methods or antibodies for use provided herein is heterozygous for the F158V single nucleotide polymorphism in the FCGR3A gene. In some embodiments, the individual receiving treatment according to methods or antibodies for use provided herein is homozygous for the F158V single nucleotide polymorphism in the FCGR3A gene. In some embodiments, the individual receiving treatment according to methods or antibodies for use provided herein does not have the F158V single nucleotide polymorphism in the FCGR3A gene.

In some embodiments, the individual does not have primary refractory multiple myeloma. In some embodiments, an individual with primary refractory multiple myeloma is one who has never achieved at least a minimal response (MR) with any therapy (or line of therapy) during the disease course. In some embodiments, the individual does not have free light chain (FLC) measurable disease only. In some embodiments, the individual has not received prior treatment with an anti-CD38 antibody. In some embodiments, the individual has received prior treatment with an anti-CD38 antibody, e.g., daratumumab. In some embodiments, the individual has not received a prior therapy (or a prior line of therapy) with isatuximab. In some embodiments, the individual has not demonstrated progressive disease (PD) during a prior therapy (or prior line of therapy) with an anti-CD38 antibody. In some embodiments, the individual has not demonstrated PD within 60 days after the end of a therapy (or line of therapy) with an anti-CD38 antibody. In some embodiments, the individual has not received a prior therapy (or a prior line of therapy) with pomalidomide. In some embodiments, the individual has received a prior therapy (or a prior line of therapy) with pomalidomide. In some embodiments, the individual has not received prior allogenic hematopoietic stem cell transplantation.

In some embodiments, treatment comprises administering the anti-CD38 antibody at a dose of 10 mg/kg, the pomalidomide at a dose of 4 mg, and the dexamethasone at a dose of 40 mg (i.e., if the individual is less than 75 years of age) or at a dose of 20 mg (i.e., if the individual is 75 years of age or older). In some embodiments, the anti-CD38 antibody (such as isatuximab) is administered intravenously. In some embodiments, the pomalidomide is administered orally. In some embodiments, the dexamethasone is administered intravenously or orally In some embodiments, treatment comprises administering the anti-CD38 antibody, the pomalidomide, and the dexamethasone to the individual in 28-day cycles. In some embodiments, the anti-CD38 antibody is administered at a dose of 10 mg/kg on Days 1, 8, 15, and 22 of the first 28-day cycle (i.e., Cycle 1), the pomalidomide is administered at a dose of 4 mg on each of Days 1-21 of the first 28-day cycle (i.e., Cycle 1), and the dexamethasone is administered at a dose of 40 mg on Days 1, 8, 15, and 22 of the first 28-day cycle (i.e., Cycle 1) if the individual is under 75 years of age, or at a dose of 20 mg on Days 1, 8, 15, and 22 of the first 28-day cycle (i.e., Cycle 1) if the individual is 75 years of age or older. In some embodiments, the anti-CD38 antibody, the pomalidomide, and the dexamethasone are administered sequentially on Days 1, 8, and 15 of the first 28-day cycle (i.e., Cycle 1). In some embodiments, the pomalidomide and the dexamethasone are administered prior to the anti-CD38 antibody on Day 1 of the first 28-day cycle (i.e., Cycle 1). In some embodiments, the dexamethasone is administered prior to the anti-CD38 antibody, and the anti-CD38 antibody is administered prior to the pomalidomide on Days 8, and 15 of the first 28-day cycle (i.e., Cycle 1).

In some embodiments, treatment comprises administering the anti-CD38 antibody, the pomalidomide, and the dexamethasone in one or more 28-day cycles following the first 28-day cycle (i.e., Cycle 1). In some embodiments the anti-CD38 antibody is administered at a dose of 10 mg/kg on Days 1 and 15 of every cycle following Cycle 1 (e.g., Cycle 2, 3, 4, etc.), the pomalidomide is administered at a dose of 4 mg on each of Days 1-21 of every cycle following Cycle 1 (e.g., Cycle 2, 3, 4, etc.), and the dexamethasone is administered at a dose of 40 mg on Days 1, 8, 15, and 22 of every cycle following Cycle 1 (e.g., Cycle 2, 3, 4, etc.) if the individual is under 75 years of age, or at a dose of 20 mg on Days 1, 8, 15, and 22 of every cycle following Cycle 1 (e.g., Cycle 2, 3, 4, etc.), if the individual is 75 years of age or older. In some embodiments, the anti-CD38 antibody, the pomalidomide, and the dexamethasone are administered sequentially on Days 1 and 15 of every cycle following Cycle 1 (e.g., Cycle 2, 3, 4, etc.). In some embodiments, the pomalidomide and the dexamethasone are administered prior to the anti-CD38 antibody on Day 1 of every 28-day cycle following Cycle 1 (e.g., Cycle 2, 3, 4, etc.). In some embodiments, the dexamethasone is administered prior to the anti-CD38 antibody, and the anti-CD38 antibody is administered prior to the pomalidomide on Day 15 every 28-day cycle following Cycle 1 (e.g., Cycle 2, 3, 4, etc.).

In some embodiments, treatment comprises administering the anti-CD38 antibody, the pomalidomide, and the dexamethasone to the individual in 28-day cycles. In some embodiments, the anti-CD38 antibody is administered at a dose of 10 mg/kg once every week of the first 28-day cycle (i.e., Cycle 1), the pomalidomide is administered at a dose of 4 mg for 21 days of the first 28-day cycle (i.e., Cycle 1), and the dexamethasone is administered at a dose of 40 mg once every week of the first 28-day cycle (i.e., Cycle 1) if the individual is under 75 years of age, or at a dose of 20 mg once every week of the first 28-day cycle (i.e., Cycle 1) if the individual is 75 years of age or older. In some embodiments, the anti-CD38 antibody, the pomalidomide, and the dexamethasone are administered sequentially in the first 28-day cycle (i.e., Cycle 1). In some embodiments, the pomalidomide and the dexamethasone are administered prior to the anti-CD38 antibody in the first 28-day cycle (i.e., Cycle 1). In some embodiments, the dexamethasone is administered prior to the anti-CD38 antibody, and the anti-CD38 antibody is administered prior to the pomalidomide on Days 8, and 15 of the first 28-day cycle (i.e., Cycle 1).

In some embodiments, treatment comprises administering the anti-CD38 antibody, the pomalidomide, and the dexamethasone in one or more 28-day cycles following the first 28-day cycle (i.e., Cycle 1). In some embodiments the anti-CD38 antibody is administered at a dose of 10 mg/kg once every other week of every 28-day cycle following Cycle 1 (e.g., Cycle 2, 3, 4, etc.), the pomalidomide is administered for 21 of every 28-day cycle following Cycle 1 (e.g., Cycle 2, 3, 4, etc.), and the dexamethasone is administered at a dose of 40 mg once every week of every 28-day cycle following Cycle 1 (e.g., Cycle 2, 3, 4, etc.) if the individual is under 75 years of age, or at a dose of 20 mg once every week of every 28-day cycle following Cycle 1 (e.g., Cycle 2, 3, 4, etc.), if the individual is 75 years of age or older. In some embodiments, the anti-CD38 antibody, the pomalidomide, and the dexamethasone are administered sequentially in every cycle following Cycle 1 (e.g., Cycle 2, 3, 4, etc.). In some embodiments, the pomalidomide and the dexamethasone are administered prior to the anti-CD38 antibody in every 28-day cycle following Cycle 1 (e.g., Cycle 2, 3, 4, etc.). In some embodiments, the dexamethasone is administered prior to the anti-CD38 antibody, and the anti-CD38 antibody is administered prior to the pomalidomide in every 28-day cycle following Cycle 1 (e.g., Cycle 2, 3, 4, etc.).

In some embodiments, the PFS of the individual is measured as the period of time from the start of treatment to the first occurrence of progressive disease (PD). In some embodiments, PD is assessed according to the criteria in Kumar et al. (2016) "International Myeloma Working Group consensus criteria for response and minimal residual disease assessment in multiple myeloma." *Lancet Oncol.* 17(8): e328-e346) and Durie et al. (2006) "International uniform response criteria for multiple myeloma. *Leukemia.* 20: 1467-1473. (See also TableA and Table B). In some embodiments, PFS is measured as the time from the start of treatment to the time of death. In some embodiments, the methods and uses provided herein result in improved (e.g., extended) progression free survival (PFS) of the individual, by at least about 8.5, 9, 9.5, 10, 10.5, 11, 11.5, 12, 12.5, 13, 13.5, 14, 14.5, 15, or more than 15 months (including any range in between these values). In some embodiments, the treatment increases the progression free survival (PFS) of the individual by at least about 11.53 months. In some embodiments, the treatment increases (e.g., extends) the progression free survival (PFS) of the individual by at least about 11.14 months. In some embodiments, the treatment increases (e.g., extends) the PFS of the individual by at least about any one of 4.5, 5, 5.5, 6, 6.5, 7, 7.5, 8, 8.5, 9, 9.5, 10, 10.5, 11, 11.5, or more than 11.5 months (including any range in between these values), as compared to an individual having multiple myeloma (such as refractory multiple myeloma or relapsed and refractory multiple myeloma) who received treatment comprising pomalidomide and dexamethasone without the anti-CD38 antibody. In some embodiments, the treatment increases (e.g., extends) the PFS of the individual by at least about 5 months, as compared to an individual having multiple myeloma (such as refractory multiple myeloma or relapsed and refractory multiple myeloma) who received treatment comprising pomalidomide and dexamethasone without the anti-CD38 antibody. In some embodiments, the treatment increases (e.g., extends) the PFS of the individual by at least about 4.5 months, as compared to an individual having multiple myeloma (such as refractory multiple myeloma or relapsed and refractory multiple myeloma) who received treatment comprising pomalidomide and dexamethasone without the anti-CD38 antibody.

In some embodiments, overall survival (OS) is measured as the period of time from the start of treatment to death. In some embodiments, the treatment increases (such as extends) the OS of the individual as compared to an individual having multiple myeloma (such as refractory multiple myeloma or relapsed and refractory multiple myeloma) who received treatment comprising pomalidomide and dexamethasone without the anti-CD38 antibody.

In some embodiments, the time to first response in an individual receiving treatment with the anti-CD38 antibody, pomalidomide, and dexamethasone according to methods or antibodies for use provided herein is shorter than the time to first response in individual receiving treatment with pomalidomide and dexamethasone. In some embodiments, treatment with the anti-CD38 antibody, pomalidomide, and dexamethasone according to a method or antibody for use provided herein decreases the time to first response in individual, as compared to the time to first response of an individual receiving treatment with pomalidomide and dexamethasone. In some embodiments, "time to first response" refers to the duration of time between the date of the first dose and the date of the first sign of response, e.g., a response according to the criteria described in Kumar et al. (2016) "International Myeloma Working Group consensus criteria for response and minimal residual disease assessment in multiple myeloma." *Lancet Oncol.* 17(8): e328-e346) and Durie et al. (2006) "International uniform response criteria for multiple myeloma. *Leukemia.* 20: 1467-1473 (see also Table A and Table B).

In some embodiments, the individual is negative for minimal residual disease (MRD) or "MRD-negative" following treatment with the anti-CD38 antibody, pomalidomide, and dexamethasone. In some embodiments, MRD status is measured by next generation flow cytometry (NGF). In some embodiments, MRD-negative as measured by NGF (or "flow MRD-negative") refers to the absence of phenotypically aberrant clonal plasma cells (such as multiple myeloma cells) in bone marrow aspirates (for example using the EUROFLOW™ high-throughput flow cytometry standard operation procedure for MRD detection in multiple myeloma (see Flores-Montero et al. (2017) *Leukemia.* 31: 2094-2103) or an equivalent method) with a minimum sensitivity of, e.g., 1 in $10^4$ nucleated cells ($10^{-4}$), 1 in $10^5$ nucleated cells ($10^{-5}$), 1 in $10^6$ nucleated cells ($10^{-6}$), or 1 in $10^7$ nucleated cells ($10^{-7}$). In some embodiments, the individual is MRD-negative via NGF at a threshold of $10^{-4}$, $10^{-5}$, or $10^{-6}$ following treatment with the anti-CD38 antibody, pomalidomide, and dexamethasone.

In some embodiments, MRD status is measured by next generation sequencing (NGS). In some embodiments, MRD-negative as measured by NGS (or "sequencing MRD negative") refers to absence of clonal plasma cells (e.g., multiple myeloma cells) in bone marrow aspirates; the presence of a clone is defined as at least two identical sequencing reads obtained after DNA sequencing of bone marrow aspirates (for example, using the LYMPHO-SIGHT® high-throughput sequencing platform or equivalent method) with a minimum sensitivity of, e.g., 1 in $10^4$ nucleated cells ($10^{-4}$), 1 in $10^5$ nucleated cells($10^{-5}$), 1 in $10^6$ nucleated cells ($10^{-6}$), or higher. In some embodiments, the minimum sensitivity is 1 cell in $10^6$ (or $10^{-6}$) nucleated cells. In some embodiments, the individual is MRD-negative via NGS at a threshold of $10^{-4}$, $10^{-5}$, or $10^{-6}$ following treatment with the anti-CD38 antibody, pomalidomide, and dexamethasone.

In some embodiments, the individual is negative by both imaging and MRD (or "imaging+MRD negative"). In some embodiments, imaging+MRD negative refers to (a) being MRD-negative as detected by NGF or MRD-negative as detected by NGS and (b) disappearance of every area of increased tracer uptake found at baseline or a preceding positron emission tomography (PET)/computed tomography (Ct) or decrease to <mediastinal blood pool maximum standardized uptake value or decrease to less than that of surrounding normal tissue. In some embodiments, the individual is "sustained MRD-negative." In some embodiments, sustained MRD negativity refers to an individual who has been confirmed to be imaging+MRD-negative at two time points following the start of treatment, wherein the time points are no less than 1 year apart. In some embodiments, minimal residual disease (MRD) is assessed via NGF or NGS using a bone marrow sample collected from an individual who has received treatment with isatuximab, pomalidomide, and dexamethasone, as described herein. In some embodiments, the individual who is assessed for MRD has achieved complete response after treatment with isatuximab, pomalidomide, and dexamethasone, as described herein. In some embodiments, the individual is negative by both imaging and MRD via NGS or NGF at a threshold of $10^4$, $10^{-5}$, or $10^{-6}$ following treatment with the anti-CD38 antibody, pomalidomide, and dexamethasone.

In some embodiments, the individual is less than 65 years of age. In some embodiments, the one-year overall survival rate of an individual less than 65 years of age receiving treatment with the anti-CD38 antibody, pomalidomide, and dexamethasone is at least any one of about 60%, 61%, 62%, 63%, 64%, 65%, 66%, 67%, 67.1%, 67.2%, 67.3%, 67.4%, 67.5%, 67.6%, 67.7%, 67.8%, 67.9%, or 68%, including any range in between these values. In some embodiments, the PFS of an individual less than 65 years of age receiving treatment with the anti-CD38 antibody, pomalidomide, and dexamethasone is at least any one of about 9, 9.5, 10, 10.5, 11, 11.1, 11.2, 11.3, 11.4, 11.5, 11.53, 11.6 11.7, 11.8, 11.9, or 12 months, including any range in between these values. In some embodiments, the PFS of an individual less than 65 years of age receiving treatment with the anti-CD38 antibody, pomalidomide, and dexamethasone is at least any one of about 3, 3.5, 4, 4.5, 5, 5.5, 6, 6.5, or 7 months longer than the PFS of an individual less than 65 years of age receiving treatment with pomalidomide, and dexamethasone, but without the anti-CD38 antibody, including any range between these values. In some embodiments, PFS is calculated as described elsewhere herein.

In some embodiments, the individual is at least 65 but less than 75 years of age. In some embodiments, the one-year overall survival rate of an individual least 65 but less than 75 years of age receiving treatment with the anti-CD38 antibody, pomalidomide, and dexamethasone is at least any one of about 65%, 66%, 67%, 68%, 69%, 70%, 71%, 72%, 73%, 74%, 74.1%, 74.2%, 74.3%, 74.4%, 74.5%, 74.6%, 74.7%, 74.8%, 74.9%, or 75%, including any range in between these values. In some embodiments, the PFS of an individual at least 65 but less than 75 years of age receiving treatment with the anti-CD38 antibody, pomalidomide, and dexamethasone is at least any one of about 9.5, 10, 10.5, 11, 11.1, 11.2, 11.3, 11.4, 11.5, 11.57, 11.6, 11.7, 11.8, 11.9, or 12 months, including any range between these values. In some embodiments, the PFS of an individual at least 65 but less than 75 years of age receiving treatment with the anti-CD38 antibody, pomalidomide, and dexamethasone is at least any one of about 1, 1.5, 2, 2.5, 2.6, 2.7, 2.8, 2.9, 2.99, or 3 months longer than the PFS of an individual at least 65 but less than 75 years of age receiving treatment with pomalidomide, and dexamethasone, but without the anti-CD38 antibody, including any range between these values. In some embodiments, PFS is calculated as described elsewhere herein.

In some embodiments, the individual is 75 years of age or older. In some embodiments, the one-year overall survival rate of an individual 75 years of age or older receiving treatment with the anti-CD38 antibody, pomalidomide, and dexamethasone is at least any one of about 65%, 66%, 67%, 68%, 69%, 70%, 71%, 72%, 73%, 73.1%, 73.2%, 73.3%, 73.4%, 73.5%, 73.6%, 73.7%, 73.8%, 73.9%, or 74%, including any range in between these values. In some embodiments, the one-year overall survival rate of an individual 75 years of age or older receiving treatment with the anti-CD38 antibody, pomalidomide, and dexamethasone is higher than the one-year overall survival rate of individual 75 years of age or older receiving treatment with pomalidomide, and dexamethasone, but without the anti-CD38 antibody. In some embodiments, the one-year overall survival rate of an individual 75 years of age or older receiving treatment with the anti-CD38 antibody, pomalidomide, and dexamethasone is at least any one of about 21, 22, 23, 24, 25, 26, 26.1, 26.2, 26.3, 26.4, 26.5, 26.6, 26.7, 26.8, 26.9, or 27 percentage points higher than the one-year overall survival rate of individual 75 years of age or older receiving treatment with pomalidomide, and dexamethasone, but without the anti-CD38 antibody. In some embodiments, the PFS of an individual 75 years of age or older receiving treatment with the anti-CD38 antibody, pomalidomide, and dexamethasone is at least any one of about 9.5, 10, 10.5, 11, 11.1, 11.2, 11.3, 11.4, 11.5, 11.6, 11.7, 11.8, 11.9, or 12 months, including any range between these values. In some embodiments, the PFS of an individual 75 years of age or older receiving treatment with the anti-CD38 antibody, pomalidomide, and dexamethasone is at least any one of about 3, 3.5, 4, 4.5, 5, 5.5, 6, 6.1, 6.2, 6.3, 6.4, 6.5, 6.6, 6.7, 6.8, 6.9, or 7 months longer than the PFS of an individual 75 years of age or older receiving treatment with pomalidomide, and dexamethasone, but without the anti-CD38 antibody, including any range between these values. In some embodiments, PFS is calculated as described elsewhere herein.

In some embodiments, the individual is female (e.g. a fertile female of childbearing age). In some embodiments, where the patient is female and is able to become pregnant, the patient may use an effective method of contraception during the treatment with the anti-CD38 antibody and for five months after the last dose of the anti-CD38 antibody. In some embodiments the individual has hepatic impairment, such as mild hepatic impairment. In some embodiments, an individual has mild hepatic impairment if the individual's total bilirubin is between about 1 and about 1.5 times the upper limit of normal (ULN). In some embodiments, an individual has mild hepatic impairment if the individual's aspartate aminotransferase (AST) level is greater than the upper limit of normal (ULN). In some embodiments, the individual has received at least three (e.g., 4, 5, 6, 7, 8, etc.) prior therapies (or prior lines of therapy) for multiple myeloma. In some embodiments, the individual has a Glomerular Filtration Rate (creatinine clearance) of less than about 60, less than about 50, or less than about 30 ml/min/1.73 m$^2$ prior to the start of treatment. In some embodiments, the individual is Stage II or Stage III according to the Multiple Myeloma International Stating System (ISS). In some embodiments, Stage II according to the Multiple Myeloma ISS is defined as a serum beta-2 microglobulin level of between about 3.5 and about 5.5 mg/L or greater. In some embodiments, Stage II according to the Multiple Myeloma ISS is defined as a serum albumin level of less than about 3.5 g/dL. In some embodiments, Stage III according to the Multiple Myeloma ISS is defined as a serum beta-2 microglobulin level of greater than about 5.5 mg/L. In some embodiments, the individual is Stage III according to the Multiple Myeloma Revised International Stating System (R-ISS). In some embodiments, Stage III according to the Multiple Myeloma R-ISS is defined as (a) a serum beta-2 microglobulin level of greater than about 5.5 mg/L and either (b) high-risk cytogenetic abnormality detected by interphase fluorescent in situ hybridization (iFISH) or (c) a serum lactate dehydrogenase (LDH) level greater than the upper limit of normal. In some embodiments, the individual has a high-risk cytogenetic abnormality (CA). In some embodiments, the high-risk cytogenetic abnormality is one or more of del(17p), t(4:14), and/or t(14;16).

Articles of Manufacture or Kits

In another embodiment of the invention, an article of manufacture or a kit is provided comprising an anti-CD38 antibody (such as isatuximab). In some embodiments, the article of manufacture or kit further comprising pomalidomide, and/or dexamethasone. In some embodiments, the article of manufacture or kit further comprises package insert comprising instructions for using the anti-CD38 antibody (e.g., isatuximab) in conjunction with the pomalidomide and the dexamethasone to treat or delay progression of multiple myeloma (e.g., refractory multiple myeloma or relapsed and refractory multiple myeloma) in an individual who has received at least two prior therapies for multiple myeloma. In some embodiments, the kit comprises isatuximab, pomalidomide, and dexamethasone.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The present disclosure will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: A Phase III Randomized, Open-Label, Multicenter Study Comparing Isatuximab (SAR650984) in Combination with Pomalidomide and Low-Dose Dexamethasone Vs. Pomalidomide and Low-Dose Dexamethasone in Patients with Refractory or Relapsed and Refractory Multiple Myeloma This Example describes a phase III, multicenter, multinational, randomized, open-label, parallel group, 2-arm study that evaluated the efficacy of isatuximab in combination with pomalidomide and low-dose dexamethasone compared with pomalidomide and low-dose dexamethasone for the treatment of patients with refractory or relapsed and refractory multiple myeloma who had received at least 2 prior lines therapy (e.g., ≥2 lines prior lines of therapy) for multiple myeloma, including lenalidomide and a proteasome inhibitor (e.g., bortezomib, carfilzomib or ixazomib), given alone or in combination, and who have demonstrated disease progression on or within 60 days of completion of the last therapy (e.g., who were refractory to the last therapy).

I. Study Objectives

A. Primary Objective

The primary objective (i.e., primary endpoint) of this study was to demonstrate the benefit of isatuximab in combination with pomalidomide and low-dose dexamethasone (i.e., the "IPd arm") in the prolongation of PFS as compared to pomalidomide and low-dose dexamethasone (i.e., "Pd arm") in patients with refractory or relapsed and refractory multiple myeloma. PFS was defined as the time from the date of randomization to the date of first documentation of progressive disease (PD), as determined by independent response committee (IRC) or the date of death from any cause, whichever came first.

PD (IMWG criteria, as described in Kumar et al. (2016) "International Myeloma Working Group consensus criteria for response and minimal residual disease assessment in multiple myeloma." Lancet Oncol. 17(8): e328-e346) and Durie et al. (2006) "International uniform response criteria for multiple myeloma. Leukemia. 20: 1467-1473, was defined for patients with measurable serum and/or urine M protein as any one of the following (see also Table A and Table B):

- increase of ≥25% in Serum M-component from nadir (the absolute increase must have been ≥0.5 g/dL) in 2 consecutive assessments; serum M component increases ≥1 g/dL in 2 consecutive assessments are sufficient to define relapse if starting M component is ≥5 g/dL and/or
- increase of ≥25% in Urine M-component from nadir (the absolute increase must have been ≥200 mg/24 h) in 2 consecutive assessments and/or
- definite development of new bone lesions or soft tissue extramedullary disease or increase ≥50% from nadir in the sum of perpendicular diameters of existing soft tissue extramedullary disease lesions if >1 lesion or ≥50% increase in the longest diameter of a previous soft tissue extramedullary disease lesion >1 cm in short axis. (Pathological fracture or collapse of bone were not necessarily evidence of disease progression.)

B. Key Secondary Objectives

The key secondary objectives (i.e., key secondary endpoints or key secondary efficacy endpoints) of this study were: (1) to evaluate the overall response rate (ORR) as per International Myeloma Working Group (IMWG) criteria (as described in Kumar et al. (2016) "International Myeloma Working Group consensus criteria for response and minimal residual disease assessment in multiple myeloma." Lancet Oncol. 17(8): e328-e346 and Durie et al. (2006) "International uniform response criteria for multiple myeloma. Leukemia. 20: 1467-1473) in each arm; and (2) to compare overall survival (OS) between the IPd and Pd arms.

ORR was defined as the proportion of patients with stringent complete response (sCR), complete response (CR), very good partial response (VGPR), and partial response (PR), as assessed by independent response committee using the IMWG response criteria. See Table A and Table B below. A plasmacytoma that had been radiated was not suitable for response assessment; however, it must have been monitored to assess for progressive disease. For patients achieving very good partial response by other criteria, a soft tissue plasmacytoma must have decreased by more than 90% in the sum of the maximal perpendicular diameter (SPD) compared with baseline.

TABLE A

Standard International Myeloma Working Group (IMWG) Response Criteria

| Response | IMWG Criteria |
| --- | --- |
| Complete Response (CR) | negative immunofixation on the serum and urine, and disappearance of any soft tissue plasmacytomas, and <5% plasma cells in bone marrow aspirates. A normal FLC ratio of 0.26-1.65 is required. Two consecutive assessments are needed. No known evidence of progressive disease or new bone marrow lesions if radiographic studies were performed |
| Stringent Complete Response (sCR) | CR as defined above, plus: a normal free light chain (FLC) ratio of 0.26-1.65, and absence of clonal cells in bone marrow by immunohistochemistry (κ/λ ratio ≤4:1 or ≥1:2 for κ and λ patients, respectively, after counting ≥100 plasma cells). Two consecutive assessments of laboratory parameters are needed. No known evidence of progressive disease or new bone marrow lesions if radiographic studies were performed. |
| Very Good Partial Response (VGPR) | serum and urine M-protein detectable by immunofixation but not on electrophoresis, or ≥90% reduction in serum M-protein plus urine M-protein level <100 mg/24 h. Two consecutive assessments of laboratory parameters are needed. No known evidence of progressive disease or new bone marrow lesions if radiographic studies were performed. |
| Partial Response (PR) | ≥50% reduction of serum M-protein and reduction in 24 hours urinary M-protein by ≥90% or to <200 mg/24 h, and If present at baseline, a ≥50% reduction in the size (SPD‡) of soft tissue plasmacytomas is also required. Two consecutive assessments of laboratory parameters are needed. No known evidence of progressive disease or new bone marrow lesions if radiographic studies were performed. |

TABLE A-continued

Standard International Myeloma Working
Group (IMWG) Response Criteria

| Response | IMWG Criteria |
|---|---|
| Minimal Response (MR) | ≥25% but ≤49% reduction of serum M-protein and reduction in 24 hours urinary M-protein by 50-80%, which still exceed 200 mg/24 h, and If present at baseline, a ≥50% reduction in the size (SPD‡) of soft tissue plasmacytomas is also required. No known evidence of progressive disease or new bone marrow lesions if radiographic studies were performed. |
| Stable Disease (SD) | Not meeting criteria for CR, VGPR, PR, MR, or progressive disease. Two consecutive assessments are needed. No known evidence of progressive disease or new bone marrow lesions if radiographic studies were performed |
| Progressive Disease (PD) | Any one or more of the following criteria: Increase of ≥25% from lowest confirmed value in any one of the following criteria: Serum M-protein (the absolute increase must have been ≥0.5 g/dL). Serum M-protein increase ≥1 g/dL if the lowest M component was ≥5 g/dL. Urine M-component (the absolute increase must have been ≥200 mg/24 h). Appearance of new lesion(s), ≥50% increase from nadir in SPD‡ of >1 lesion, or ≥50% increase in the longest diameter of a previous lesion >1 cm in short axis; ≥50% increase in circulating plasma cells (minimum of 200 cells per μL) if this is the only measure of disease Two consecutive assessments are needed. No known evidence of progressive disease or new bone marrow lesions if radiographic studies were performed |

‡SPD, sum of the products of the maximal perpendicular diameters of measured lesions Patients continued in the last confirmed response category until there was confirmation of progression or improvement to a higher response status; patients could not move to a lower response category. Percent decreases for response calculations were from baseline values (Cycle 1, Day 1). Percent increases for progression calculations were from lowest response values or baseline values, whichever was the smaller number. The lowest value did not need to be confirmed. The lowest confirmed value before suspected progression was used as baseline for calculation of progression; if a serum and/or urine spike was considered too low to quantitate, this value could be assigned as zero as a baseline for documentation of subsequent progressive disease. Patients were considered to have progressive disease if they met the criteria for progression by a variable that was not considered measurable at baseline; however, for patients who had a measurable serum or urine M-spike at baseline, progression could not be defined by increases in serum FLC alone.

For patients who had serum and urine M-Protein below level of eligibility on efficacy laboratory performed on Cycle 1 Day 1 (e.g., patients with only FLC measurable disease according to IMWG or patients without any biological measurable disease) could only have only one of two possible overall responses: non-PD or PD. In such cases, PD could be diagnosed on the following parameters:

for patients with only FLC measurable: M protein and plasmacytoma according to IMWG criteria described in the table above, for patients with non-measurable disease: M protein and plasmacytoma, or an increase of bone marrow plasma cell percentage involvement ≥10%.

Overall survival (OS) was defined as the time from the date of randomization to death from any cause.

C. Other Secondary Objectives

Other secondary objectives ("secondary endpoints") of this study were: (1) to evaluate the time to progression (TTP) in each arm; (2) to evaluate the PFS in high risk cytogenetic population defined as patients carrying del(17p), t(4;14), t(14;16) in each arm; (3) to evaluate the duration of response (DOR) in each arm; (4) to evaluate safety in both treatment arms; (5) to determine the pharmacokinetic profile of isatuximab in combination with pomalidomide; (6) to evaluate the immunogenicity of isatuximab; (7) To assess disease-specific and generic health-related quality of life (HRQL), disease and treatment-related symptoms, health state utility and health status.

Time to progression (TTP) was defined as the time from the date of randomization to the date of first documentation of progressive disease (as determined by independent response committee). The same definition of progression as for the PFS endpoint (see above) was used.

PFS in the high-risk cytogenetic population was defined as the time from the date of randomization to the date of first documentation of PD (as determined by independent response committee) or the date of death from any cause, whichever came first, in the subgroup of patients carrying high risk cytogenetic changes including del(17p), t(4;14) or t(14;16), as assessed by fluorescence in-situ hybridization (FISH).

Duration of response (DOR) was defined as the time from the date of the first independent response committee (IRC)-determined response to the date of first IRC-determined PD or death, whichever happened first. DOR was determined only for patients who achieved a response of ≥PR.

Safety in terms of treatment-emergent adverse events (TEAEs)/serious adverse events (SAE), laboratory parameters, vital signs (blood pressure, heart rate, and temperature), weight, ECOG performance status, and physical examination were assessed throughout the study. TEAEs were defined as adverse events that develop, worsen (according to the Investigator opinion), or become serious during the TEAE period (i.e., the time from first dose of study treatments up to 30 days after last dose of study treatments). Adverse events and laboratory parameters were graded using NCI-CTCAE v4.03, available at ctep(dot)cancer(dot)gov/reporting/ctc(dot)html.)

Blood samples were collected from all patients treated with in order to assess the pharmacokinetic profile of isatuximab using population pharmacokinetic approach.

The presence of antidrug antibodies (ADA, i.e., anti-isatuximab antibodies) in patients in the IPd arm were assessed throughout the study.

The European Organisation for Research and Treatment of Cancer Quality of Life Questionnaire with 30 questions (EORTC QLQ-C30), the EORTC Myeloma Module with 20 items (MY20), and the European Quality of Life Group measure with 5 dimensions and 5 levels per dimension (EQ-5D-5L) assessments were designated for self-completion by all patients (IPD arm and Pd arm). All patient reported outcomes (PRO) were completed by the patients at the center prior to discussing their health/disease status, and prior to administration of study treatments, or other study-related procedures during treatment, at end of treatment visit (EOT; 30 [+5] days after last study treatment administration) and 60 days (±5 days) after last study treatment administration.

D. Exploratory Objectives

The exploratory objectives of this study were: (1) to explore the relationship between immune genetic determinants and efficacy endpoints; (2) to explore pharmacokinetic (PK) and pharmacodynamic (PD) relationships; (3) to explore the minimal residual disease (MRD) rate in both treatment arms.

For patients who consented, a blood sample was collected at Cycle 1 Day 1. This sample was used to determine whether there exists a relationship between genetic markers and (a) treatment with isatuximab, (b) how the body processes isatuximab, and/or (c) possible side effects of isatuximab. The samples were transferred to a separate site. DNA was extracted from each sample, and stored until further analysis.

Blood samples were collected on Cycle 1 Day 1 or exploratory biomarker analyses (which were a mandatory part of the study and were not performed under separate phamacogenetic consent). Leukocyte DNA was extracted from each blood sample and analyzed for immune genetic determinants (such as FcγR polymorphisms, human leukocyte antigen (HLA), and killer cell inhibitory receptor (KIR) genotypes) and correlated with parameters of clinical response, including, e.g., ORR, DOR, PFS, and OS.

Additional serum samples were collected to evaluate the potential isatuximab interference with M protein assessment in immunoelectrophoresis and immunofixation assays. These samples were collected at all time points at which M protein is analyzed from patients in the IPd arm.

Pharmacokinetic and pharmacodynamic estimates were investigated as prognostic factors for clinical outcome including safety and efficacy endpoints, where possible.

Minimal residual disease (MRD) was assessed via next-generation sequencing (NGS) using the CLONOSEQ® NGS platform in bone marrow samples obtained only from patients who achieved CR. MRD status was categorized as outlined in Table B below. Bone marrow aspirates were collected at baseline/screening and the time of CR confirmation. If the patient presented with CR but was determined to be MRD positive, another bone marrow sample was collected 3 months (3 cycles) later in order to identify late negativity. In certain cases, a third sample was collected after another 3 months if the patient remained MRD positive and was still being treated. No more than 3 on-treatment bone marrow samples were obtained for each patient.

TABLE B

International Myeloma Working Group (IMWG) Minimal Residual Disease Criteria*

| | |
|---|---|
| Sustained MRD-negative | MRD negativity in the marrow (as determined by next-generation flow cytometry and/or next generation sequencing) and by imaging as defined in the last row of this table, confirmed minimum of 1 year apart. Subsequent evaluations could be used to further specify the duration of negativity (e.g., MRD-negative at 5 years). |
| Flow MRD-negative | Absence of phenotypically aberrant clonal plasma cells by next generation flow cytometry on bone marrow aspirates using the EuroFlow standard operation procedure for MRD detection in multiple myeloma (or validated equivalent method) with a minimum sensitivity of 1 in $10^5$ nucleated cells or higher. |
| Sequencing MRD-negative | Absence of clonal plasma cells by next generation sequencing on bone marrow aspirates in which presence of a clone is defined as less than two identical sequencing reads obtained after DNA sequencing of bone marrow aspirates using the LYMPHOSIGHT® high-throughput sequencing platform (or validated equivalent method) with a minimum sensitivity of 1 in $10^5$ nucleated cells or higher. |
| Imaging + MRD-negative | MRD negative as defined by next generation flow cytometry or next generation sequencing PLUS Disappearance of every area of increased tracer uptake found at baseline or a preceding PET/CT or decrease to < mediastinal blood pool maximum standardized uptake value or decrease to less than that of surrounding normal tissue. |

*Assessed in patients achieving a CR according to the criteria in Table A

Each of the efficacy assessments described above were chosen for use in this study and are considered well established and relevant in a hemato-oncology setting.

II. Study Design

After confirmation of eligibility criteria (which are described in further detail below), patients were randomly assigned using an interactive response technology (IRT) system in a 1:1 ratio to one of the two arms shown in Table C below.

TABLE C

Study Treatment Arms

| TREATMENT ARM | Cycle 1 (28-day cycle) | Cycles ≥2 (28-day cycles) |
|---|---|---|
| IPd (experimental) 154 patients | Isatuximab: 10 mg/kg on Days 1, 8, 15, and 22<br>Pomalidomide: 4 mg/day on each of Days 1-21<br>Dexamethasone: 40 mg on Days 1, 8, 15, and 22 (for patients <75 years of age) or 20 mg on Days 1, 8, 15, and 22 (for patients ≥75 years of age) | Isatuximab: 10 mg/kg on Days 1 and 15<br>Pomalidomide: 4 mg/day on each of Days 1-21<br>Dexamethasone: 40 mg on days 1, 8, 15, and 22 (for patients <75 years of age) or 20 mg on Days 1, 8, 15, and 22 (for patients ≥75 years of age) |
| Pd (control) 153 patients | Pomalidomide: 4 mg/day on each of Days 1-21<br>Dexamethasone: 40 mg on days 1, 8, 15, and 22 (for patients <75 years of age) or 20 mg on Days 1, 8, 15, and 22 (for patients ≥75 years of age) | Pomalidomide: 4 mg/day on each of Days 1-21<br>Dexamethasone: 40 mg on days 1, 8, 15, and 22 for patients <75 years of age) or 20 mg on Days 1, 8, 15, and 22 (for patients >75 years of age) |

Figure 1:
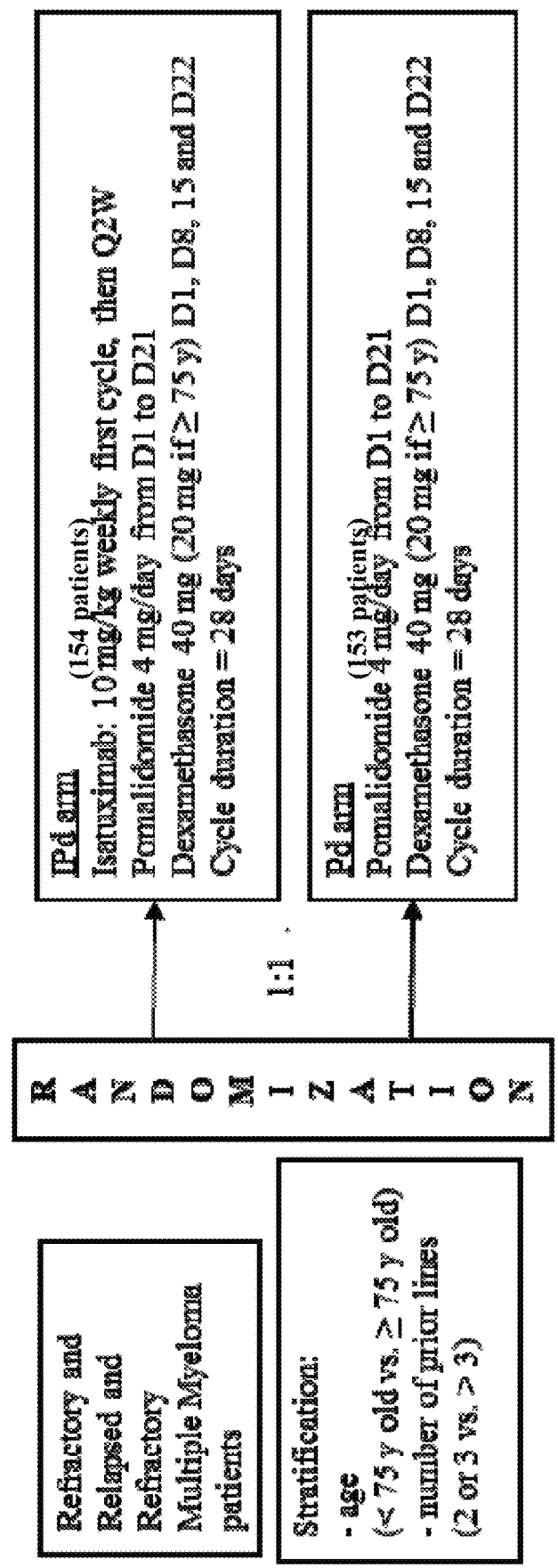
FIG. 1 provides a schematic of the study design of the clinical trial described in Example 1. The IPd (experimental) arm included 154 patients. The Pd (control) arm included 153 patients.

Randomization was stratified by age (<75 years vs. ≥75 years) and number of previous lines of therapy (2 or 3 vs. more than 3). A complete transplant procedure (induction, mobilization, conditioning, transplant, consolidation and maintenance) was considered as one line. Each additional regimen was considered as one line, whatever the reason of discontinuation (progression, adverse event or patient request). Patients continued treatment until disease progression, unacceptable adverse events (e.g., unacceptable toxicity), or patient wish, whichever came first. The study design is summarized in FIG. 1.

A. Duration of Study Participation for Each Patient

Each patient was considered in the study from informed consent signature until death, consent withdrawal or cut-off date, whichever came first. The duration of the study for a patient included a period for screening of up to 3 weeks. The duration of each treatment cycle was 28 days. Patients continued study treatment until disease progression, unacceptable AEs, patient wish, or any other reason. During follow-up, patients who discontinued study treatment due to progressive disease (PD) were followed every 3 months (12 weeks) for survival until death or cut-off date, whichever came first. Patients who discontinued the study treatment prior to documentation of progressive disease (PD) were followed-up every 4 weeks until disease progression (even for patients initiated further anti-myeloma therapy without PD), and then every 3 months (12 weeks) for survival, until death or cut-off date, whichever came first.

If a patient was still on treatment at the time of the cut-off date for OS and was benefitting from the study treatment, the patient could continue the study treatment until disease progression, unacceptable AEs, patient wish, or any other reason. For cycles completed after the cut-off date, all new related AEs (serious or not), all ongoing SAE (related or not) and all ongoing related non-serious AEs, and reason of end of treatment (EOT) continued to be collected.

B. Determination of End of Clinical Trial (all Patients)

PFS analysis (primary endpoint analysis) was event driven and the cut-off date for PFS analysis was when 162 PFS events (progression or death, whichever came first) occurred. The OS analysis was event driven and the final cut-off date was when 220 deaths occurred.

III. Selection of Patients

A. Inclusion Criteria

Eligible patients were considered for inclusion if they met all of the following criteria:

Age: ≥18 years or country's legal age of majority if the legal age is >18 years old.

Patients must have had a documented diagnosis of multiple myeloma with evidence of measurable disease.

Serum M protein ≥0.5 g/dL measured using serum protein immunoelectrophoresis and/or Urine M protein ≥200 mg/24 hours measured using urine protein immunoelectrophoresis.

Patients must have received at least 2 prior lines of anti-myeloma therapy, which must have included at least 2 consecutives cycles of lenalidomide and a proteasome inhibitor (bortezomib, carfilzomib or ixazomib), given alone or in combination. (Note: An induction treatment followed by ASCT and consolidation/maintenance was considered as one line of treatment.).

Patients must have failed treatment with lenalidomide and a proteasome inhibitor (bortezomib, carfilzomib or ixazomib) alone or in combination, defined by any of the following (failure to lenalidomide and a proteasome inhibitor can have occurred at any line of therapy):

Progression occurred while on or within 60 days from end of the treatment with lenalidomide and/or a proteasome inhibitor.

In cases of previous response ≥PR to lenalidomide and/or a proteasome inhibitor, patient must have progressed within 6 months after discontinuation of the treatment.

Patients who have developed intolerable toxicity after a minimum of 2 consecutive cycles of a regimen containing lenalidomide and a proteasome inhibitor (bortezomib, carfilzomib or ixazomib) alone or in combination. Intolerance is defined as below:

For proteasome inhibitor-containing regimens: any toxicity leading to discontinuation of a proteasome inhibitor, like ≥Grade 2 peripheral neuropathy or ≥Grade 2 neuropathic pain. Peripheral neuropathy must have been ≤Grade 1 before study entry (according to National Cancer Institute Common Terminology for Adverse Event (NCI-CTCAE) v4.03, available at ctep(dot)cancer(dot)gov/reporting/ctc(dot)html).

For lenalidomide-containing regimens, any toxicity leading to the discontinuation of lenalidomide, like Grade 3 rash. Rash must not have been Grade 4, and other non-hematologic toxicities should not have been Grade 4. All non-hematologic toxicities must have been ≤G1 before study entry.

Patients must have progressed on or within 60 days after end of the previous therapy before study entry, i.e., refractory to the last line of treatment. This patient population includes the following two categories:

Refractory disease: patients who were refractory to all previous lines of treatment but should have achieved at least a minimal; response (MR) in one previous line.

Relapsed and refractory disease: patients who were relapsed from at least one previous line of treatment and refractory to the last line of treatment. Patients could have been refractory to other previous line/lines of treatment.

Note: Patients must have achieved a MR or better to at least one of the previous lines of treatment (i.e., primary refractory disease is not eligible).

B. Exclusion Criteria

Patients who met all the inclusion criteria above were screened for the following exclusion criteria:

Primary refractory multiple myeloma defined as: patients who have never achieved at least a MR with any treatment during the disease course.

Free Light Chain measurable disease only.

Patients with prior anti-CD38 monoclonal antibody treatment (with progression on or within 60 days after end of anti-CD38 monoclonal antibody treatment, e.g., refractory to prior therapy with anti-CD38 monoclonal antibody treatment).

Prior therapy with pomalidomide.

Any anti-myeloma drug treatment within 14 days before randomization, including dexamethasone.

Prior allogenic HSC transplant with active graft versus host disease (GvHD) (GvHD any grade and/or being under immunosuppressive treatment within the last 2 months).

Any major procedure within 14 days before the initiation of the study treatment: plasmapheresis, major surgery (kyphoplasty was not considered a major procedure), radiotherapy.

Patients who have received any other investigational drugs or prohibited therapy for this study within 28 days or 5 half-lives from randomization, whichever was longer.

Eastern Cooperative Oncology Group (ECOG) performance status >2 (as described at ecog-acrin(dot)org/resources/ecog-performance-status and/or Oken et al. (1982) "Toxicity and response criteria of the Eastern Cooperative Oncology Group." *Am J. Clin Oncol.* 5: 649-655).

Platelets <75 000 cells/μL if <50% of bone marrow (BM) nucleated cells were plasma cells, and <30 000 cells/μL if ≥50% of BM nucleated cells were plasma cells. Platelet transfusion was not allowed within three days before the screening visit ANC (absolute neutrophil count)<1000μ/L (1×10$^9$/L). The use of G-CSF was not allowed to reach this level.

Creatinine clearance <30 mL/min (Modification of Diet in Renal Disease (MDRD) Equation: GFR (mL/min/1.73 m$^2$)=175×(Scr)$^{-1.154}$×(Age)$^{-0.203}$×(0.742 if Female)× (1.212 if African-American)).

Total bilirubin >2×ULN.

Corrected serum calcium >14 mg/dL (>3.5 mmol/L)

AST and/or ALT>3×ULN

Ongoing toxicity (excluding alopecia and those listed in eligibility criteria) from any prior anti-myeloma therapy >Grade 1, as outlined in NCI-CTCAE v4.03, available at ctep(dot)cancer(dot)gov/reporting/ctc(dot)html.)

Hypersensitivity to IMiDs® (thalidomide or lenalidomide), defined as any hypersensitivity reaction leading to stop IMiDs within the 2 first cycles or reaction, which does meet intolerance definition (provided above in the inclusion criteria).

Hypersensitivity to dexamethasone, sucrose histidine (as base and hydrochloride salt) and polysorbate 80 or any of the components of study therapy that are not amenable to premedication with steroids, or H2 blockers that would prohibit further treatment with these agents.

Significant cardiac dysfunction; myocardial infarction within 12 months; unstable, poorly controlled angina pectoris.

Diagnosed or treated for another malignancy within 3 years prior to randomization with the exception of complete resection of basal cell carcinoma or squamous cell carcinoma of the skin, an in situ malignancy, or low risk prostate cancer after curative therapy.

Known to be HIV$^+$ or to have hepatitis A, B or C active infection.

Malabsorption syndrome or any condition that can significantly impact the absorption of pomalidomide.

Active primary amyloid-light (AL) amyloidosis (evidence of end organ damage or receiving treatment for amyloidosis).

Concomitant plasma cell leukemia

Unable or unwilling to undergo to thromboprophylaxis.

Daily requirement for corticosteroids (equivalent to 10 mg/day of prednisone) for more than 7 days (except for inhalation corticosteroids).

IV. Study Treatments

A. Investigational Medicinal Products (IMPs)

i. Isatuximab (IV)

Isatuximab was formulated as a concentrated solution for infusion in vials containing 20 mg/mL (500 mg/25 mL) isatuximab in 20 mM histidine, 10% (w/v) sucrose, 0.02% (w/v) polysorbate 80, pH 6.0 buffer. Isatuximab was supplied for parenteral administration as a sterile, nonpyrogenic, injectable, colorless, 20 mg/mL concentrate for solution for infusion that may contain white to off-white particulates and was packaged in 30 mL glass vials fitted with elastomeric closure. Each vial contained a nominal content of 500 mg of isatuximab. The fill volume was established to ensure removal of 25 mL. For administration to patients, the appropriate volume of isatuximab is diluted in an infusion bag of 0.9% sodium chloride solution. The final infusion volume corresponding to the dose of isatuximab was administered for a period of time that depended on dose administered and was based on protein amount given per hour.

Isatuximab was administered at a dose of 10 mg/kg to patients in the IPd arm via intravenous infusion on Days 1, 8, 15, and 22 for the first 28-day cycle, and then on Days 1 and 15 for each subsequent 28-day cycle. (All cycles were 28 days in duration.) Dose modifications (described in further detail below) were applied in cases of toxicity.

ii. Pomalidomide (Oral Administration)

Pomalidomide was provided as 1 mg, 2 mg, 3 mg, and 4 mg capsules. Pomalidomide was administered orally (per os or "PO") to patients in both the IPd and Pd arms at a dose of 4 mg on Days 1 to 21 for each 28-day cycle. (All cycles were 28 days in duration.) Dose modifications (described in further detail below) were applied in cases of toxicity.

ii. Dexamethasone (Oral or IV Administration)

Dexamethasone was formulated for oral administration as 4 mg and 8 mg tablets, and for intravenous injection as a 4 mg/mL solution. Dexamethasone was administered at a dose of 40 mg for patients <75 years of age, or at a dose of 20 mg for patients ≥75 years of age, on Days 1, 8, 15 and 22 for each 28-day cycle. (All cycles were 28 days in duration.) Dose modifications (described in further detail below) were applied in cases of toxicity.

In the IPd arm, dexamethasone was administered with non-investigational medicinal products (NIMPs, described below) as premedication for the prevention of infusion-related reactions commonly observed with administration of monoclonal antibodies.

B. Non-Investigational Medicinal Products (NIMPs)—Premedication for the Prevention of Infusion Reactions (IRs)

All patients allocated to IPd arm received premedication prior to isatuximab infusion in order to reduce the risk and severity of IARs commonly observed with administration of monoclonal antibodies. The recommended premedication agents were: diphenhydramine 25-50 mg IV (or equivalent: e.g., cetirizine, promethazine, dexchlorpheniramine, according to local approval and availability. Intravenous route was preferred for at least the first 4 infusions), dexamethasone per os/IV (dose provided below), ranitidine 50 mg IV (or equivalent: other approved H2 antagonists (e.g., cimetidine), oral proton pump inhibitors (e.g., omeprazole, esomeprazole) and acetaminophen 650-1000 mg per os 15 to 30 minutes (but no longer than 60 minutes) prior to isatuximab infusion. Once the premedication regimen was completed, the isatuximab infusion started immediately.

On the day of isatuximab infusion, a total of 40 mg of dexamethasone (i.e., the regular dose of dexamethasone when used in combination with pomalidomide), or 20 mg in patients ≥75 years, was administered as part of the premedication and part of the backbone treatment before isatuximab and pomalidomide.

When dexamethasone was administered per os, the premedications were administered in the following order:

Dexamethasone 40 mg per os (or 20 mg PO for patients ≥75 years of age); then

Acetaminophen 650 mg to 1000 mg per os; then
Ranitidine 50 mg IV (or equivalent); then
Diphenhydramine 25 mg to 50 mg IV (or equivalent).

When dexamethasone was administered intravenously, the premedications were administered in the following order:

Acetaminophen 650 mg to 1000 mg per os; then
Ranitidine 50 mg IV (or equivalent); then
Diphenhydramine 25 mg to 50 mg IV (or equivalent); then
Dexamethasone 40 mg IV (or 20 mg IV for patients ≥75 years of age).

Whatever the route of administration (IV or PO), the dexamethasone was administered only once (i.e., the single administration was used for both premedication and study treatment).

No post-infusion corticosteroid or bronchodilator prophylaxis was required.

All patients received mandatory thromboprophylaxis with aspirin or low molecular weight heparin.

C. Dosage and Schedule i. IPd Arm (Experimental Arm)

Patients allocated to IPd arm received premedications prior to isatuximab infusion to reduce the risk and severity of infusion reactions (IRs) commonly observed with monoclonal antibodies (see above).

Drug administration for patients in the IPd arm was performed as follows:

Dexamethasone was administered about 15-30 minutes (but no longer than 60 minutes) prior to isatuximab at a dose of 40 mg (or 20 mg if the patient was ≥75 years old), per os (the preferred route) or intravenously (if per os route could not be used) on Days 1, 8, 15 and 22.

Isatuximab was administered at a dose of 10 mg/kg on Days 1, 8, 15, and 22 at Cycle 1, and then at a dose of 10 mg/kg on Days 1 and 15 for subsequent cycles.

Pomalidomide was administered at a dose of 4 mg on each of Days 1 to 21 of each 28-day cycle. On Day 1 of each cycle, pomalidomide was taken 1h to 30 min prior to isatuximab. On Day 8, Day 15 and Day 22 of Cycle 1 and on Day 15 of subsequent cycles, pomalidomide was taken after isatuximab infusion, and at a time which was most convenient for the patient (preferably at the same time for each dose).

ii. Pd Arm (Control Arm)

Drug administration for patients treated with pomalidomide+dexamethasone was performed as follows:

Dexamethasone was given at a dose of 40 mg (or 20 mg if the patient was ≥75 years old), per os or intravenously on Days 1, 8, 15 and 22.

Pomalidomide was given at a dose of 4 mg on each of Days 1 to 21 for each 28-day cycle.

There was no limitation in the number of cycles administered to patients in the absence of major toxicity, disease progression, or any other reason (e.g., withdrawal of consent for treatment, poor compliance, intercurrent illness that prevents further administration of study treatment, etc.). In case of progressive disease (PD), diagnosis made on laboratory criteria needed to be confirmed by two consecutive measures before to treatment discontinuation. Treatment continued until confirmation of the PD.

Each patient's weight was measured prior to each cycle to allow calculation of the isatuximab dose.

Dose adjustment (dose delay, dose omission, and dose reduction (for pomalidomide and/or dexamethasone only) was permitted for subsequent treatment cycles based on individual patient tolerance. Dose reduction steps for pomalidomide and dexamethasone are shown in Tables D1 and D2 below, respectively. One or several doses of pomalidomide could be omitted. One or several doses of dexamethasone could be omitted, or the dose of dexamethasone could be decreased to every other week (i.e., twice per 28-day cycle).

TABLE D1

Dose Levels for Pomalidomide Dose Reduction

| Starting Dose* | Dose Level −1* | Dose Level −2* | Dose Level −3* |
|---|---|---|---|
| 4 mg | 3 mg | 2 mg | 1 mg |

*all doses are per os

TABLE D2

Dose Levels for Dexamethasone Dose Reduction

| Patient Age | Starting Dose* | Dose Level −1* | Dose Level −2* | Dose Level −3* | Dose Level −4* |
|---|---|---|---|---|---|
| <75 | 40 mg | 20 mg | 12 mg | 8 mg | 4 mg |
| ≥75 | 20 mg | 12 mg | 8 mg | 4 mg | — |

*all doses are per os or IV

No dose reductions were allowed for isatuximab infusion.

V. Disease Assessment

Decisions made by the investigator regarding whether or not to permit subjects to continue treatment were based on efficacy data (obtained from local and/or central laboratories), radiological assessments, and bone marrow assessments performed throughout the study or if indicated according to IMWG criteria. The reference values to assess treatment response were the values measured in samples taken from each patient on Day 1 of Cycle 1, prior to treatment.

Serum M-protein levels were assessed via immunoelectrophoresis and, if M protein was undetectable via immunoelectrophoresis, via immunofixation.

Urine M-protein levels were assessed via immunoelectrophoresis and, if M protein was undetectable via immunoelectrophoresis, via immunofixation.

Free light chain (FLC) levels were centrally analyzed only in case of complete response (CR) (i.e., M-protein undetectable via serum protein electrophoresis/urine protein electrophoresis and negative immunofixation).

Immunoglobulins: IgG, IgA, IgM, IgD and IgE (IgD or E only if the heavy chain component of the disease is known to be E or D).

Bone marrow plasma cell infiltration was assessed to confirm CR, or if suspicion of disease progression in the absence of biochemical progression and as clinically indicated.

Bone marrow aspirate (or biopsy, if clinically indicated) for minimal residual disease (MRD) assessment in case of CR. If the patient was MRD positive, another bone marrow sample was collected 3 months (3 cycles) later in order to identify late MRD negativity. A third sample may have been collected after another 3 months (3 cycles), if the patient remained MRD positive and was still being treated. (No more than 3 on-treatment bone marrow samples were obtained from any patient.)

A skeletal survey or low-dose whole-body CT scan was performed at baseline, then once a year and anytime during the study if clinically indicated. The same modality (i.e., skeletal survey or low-dose whole-body CT) was used throughout the study for each patient.

For extramedullary disease (plasmacytoma, including bone plasmacytoma):

If extramedullary disease was present at baseline, CT scan or MRI was performed at baseline and repeated every 12 weeks (+1 week). (Additional CT scans or MRIs were performed, if clinically indicated.)

If extramedullary disease was suspected at baseline, CT scan or MRI was performed at baseline to confirm extramedullary disease. In case of confirmation, CT or MRI was and repeated every 12 weeks (+1 week). (Additional CT scans or MRIs were performed, if clinically indicated.)

The same modality (CT or MRI) was throughout the study for each individual patient.

VI. Results

A. Patient Characteristics 307 patients were randomized and included in the Intend to Treat (ITT) population (153 in Pd arm and 154 in IPd arm). Overall, patients' demographics and characteristics at baseline were representative of the RRMM population and were in general similar in the 2 treatment arms. See Table E below.

TABLE E

Demographic Characteristic of Randomized Population

|  | Pd (Control Arm) (N = 153) | IPd (Experimental Arm) (N = 154) | All (N = 307) |
|---|---|---|---|
| Age (years) | | | |
| Number | 153 | 154 | 307 |
| Mean (SD) | 65.2 (9.5) | 66.6 (9.1) | 65.9 (9.3) |
| Median | 66.0 | 68.0 | 67.0 |
| Min; Max | 41; 86 | 36; 83 | 36; 86 |
| Age group (years) [n (%)] | | | |
| Number | 153 | 154 | 307 |
| <65 | 70 (45.8) | 54 (35.1) | 124 (40.4) |
| [65-75[ | 54 (35.3) | 68 (44.2) | 122 (39.7) |
| ≥75 | 29 (19.0) | 32 (20.8) | 61 (19.9) |
| Gender [n (%)] | | | |
| Number | 153 | 154 | 307 |
| Female | 83 (54.2) | 65 (42.2) | 148 (48.2) |
| Male | 70 (45.8) | 89 (57.8) | 159 (51.8) |
| Race [n (%)] | | | |
| Number | 153 | 154 | 307 |
| White | 126 (82.4) | 118 (76.6) | 244 (79.5) |
| Black or African American | 3 (2.0) | 1 (0.6) | 4 (1.3) |
| Asian | 15 (9.8) | 21 (13.6) | 36 (11.7) |
| Native Hawaiian or other Pacific Island | 1 (0.7) | 2 (1.3) | 3 (1.0) |
| Missing/Not reported | 8 (5.2) | 12 (7.8) | 20 (6.5) |
| Ethnicity [n (%)] | | | |
| Number | 153 | 154 | 307 |
| Hispanic or Latino | 3 (2.0) | 4 (2.6) | 7 (2.3) |
| Not Hispanic or Latino | 134 (87.6) | 130 (84.4) | 264 (86.0) |
| Unknown | 2 (1.3) | 2 (1.3) | 4 (1.3) |
| Not Reported | 14 (9.2) | 18 (11.7) | 32 (10.4) |
| Prior history of asthma/COPD [n (%)] | 16 (10.5) | 16 (10.4) | 32 (20.9) |
| eGFR ≥60 ml/min/1.73 m$^2$ [n (%)] | 96/145 (66.2) | 87/142 (61.3) | 183/287 (63.7) |
| eGFR <60 ml/min/1.73 m$^2$ [n (%)] | 49/145 (33.8) | 55/142 (38.7) | 104/287 (36.2) |
| eGFR <50 ml/min/1.73 m$^2$ [n (%)] | 24/145 (16.6) | 33/142 (23.2) | 57/287 (19.9) |
| eGFR <30 ml/min/1.73 m$^2$ [n (%)] | 1/145 (0.7) | 1/142 (0.7) | 2/287 (0.7) |
| eGFR ≥45 to <60 ml/min/1.73 m$^2$ [n (%)] | 32/145 (22.1) | 35/142 (24.6) | 67/287 (23.3) |
| eGFR ≥30 to <45 ml/min/1.73 m$^2$ [n (%)] | 16/145 (11.0) | 19/142 (13.4) | 35/287 12.2) |
| ECOG performance status [n (%)] | | | |
| Number | 153 | 154 | 307 |
| 0 | 69 (45.1) | 55 (35.7) | 124 (40.4) |
| 1 | 68 (44.4) | 83 (53.9) | 151 (49.2) |
| 2 | 16 (10.5) | 16 (10.4) | 32 (10.4) |
| Geographical region$^a$ [n (%)] | | | |
| Number | 153 | 154 | 307 |
| Western Europe | 76 (49.7) | 55 (35.7) | 131 (42.7) |
| Eastern Europe | 20 (13.1) | 28 (18.2) | 48 (15.6) |
| North America | 5 (3.3) | 7 (4.5) | 12 (3.9) |
| Asia | 15 (9.8) | 21 (13.6) | 36 (11.7) |
| Other Countries | 37 (24.2) | 43 (27.9) | 80 (26.1) |

TABLE E-continued

Demographic Characteristic of Randomized Population

|  | Pd (Control Arm) (N = 153) | IPd (Experimental Arm) (N = 154) | All (N = 307) |
|---|---|---|---|
| Regulatory region[b] [n (%)] | | | |
| Number | 153 | 154 | 307 |
| Western Countries | 97 (63.4) | 77 (50.0) | 174 (56.7) |
| Other Countries | 56 (36.6) | 77 (50.0) | 133 (43.3) |

[a]Other countries = Australia, New Zealand, Turkey and Russia.
[b]Other countries = Czech Republic, Hungary, Poland, Slovakia, Japan, Korea, Republic of Taiwan (Province of China), Turkey and Russia Multiple myeloma international staging system (ISS) stage and multiple myeloma subtype at initial diagnosis were well balanced between treatment arms (see Table F). Overall, 28% of patients had ISS stage III at initial diagnosis (28.8% in Pd arm and 27.3% in IPd arm).

TABLE F

Disease Characteristics of Randomized Population at Initial Diagnosis

|  | Pd (Control Arm) (N = 153) | IPd (Experimental Arm) (N = 154) | All (N = 307) |
|---|---|---|---|
| Initial diagnosis [n (%)] | | | |
| Number | 153 | 154 | 307 |
| Multiple Myeloma | 153 (100) | 154 (100) | 307 (100) |
| Time from initial diagnosis of MM to randomization (years) | | | |
| Number | 153 | 154 | 307 |
| Mean (SD) | 5.29 (3.69) | 5.23 (3.24) | 5.26 (3.46) |
| Median | 4.09 | 4.46 | 4.23 |
| Min; Max | 0.5; 20.5 | 0.6; 18.4 | 0.5; 20.5 |
| MM subtype at initial diagnosis [n (%)] | | | |
| Number | 153 | 154 | 307 |
| Ig G | 100 (65.4) | 102 (66.2) | 202 (65.8) |
| Ig A | 41 (26.8) | 34 (22.1) | 75 (24.4) |
| Ig M | 0 | 2 (1.3) | 2 (0.7) |
| Ig D | 0 | 0 | 0 |
| Ig E | 0 | 0 | 0 |
| Kappa light chain only | 7 (4.6) | 8 (5.2) | 15 (4.9) |
| Lambda Light chain only | 4 (2.6) | 7 (4.5) | 11 (3.6) |
| Unknown/undetected | 1 (0.7) | 1 (0.6) | 2 (0.7) |
| ISS stage at initial diagnosis [n (%)] | | | |
| Number | 153 | 154 | 307 |
| Stage I | 41 (26.8) | 36 (23.4) | 77 (25.1) |
| Stage II | 48 (31.4) | 49 (31.8) | 97 (31.6) |
| Stage III | 44 (28.8) | 42 (27.3) | 86 (28.0) |
| Unknown | 20 (13.1) | 27 (17.5) | 47 (15.3) |

Ig: Immunoglobulin,
MM: Multiple Myeloma,
ISS: International staging system

At study entry, the ISS criteria were classified as Stage I and II in 73.0% of the patients and stage III in 25.1% of patients (see Table G). As per the inclusion criteria, all patients were relapsed and refractory at study entry. Disease characteristics were as expected in this heavily treated RRMM population and in general similar between the treatment arms.

TABLE G

Disease Characteristics of Randomized Population at Study Entry

|  | Pd (Control Arm) (N = 153) | IPd (Experimental Arm) (N = 154) | All (N = 307) |
|---|---|---|---|
| MM subtype at study entry [n(%)] | | | |
| Number | 153 | 154 | 307 |
| Ig G | 101 (66.0) | 104 (67.5) | 205 (66.8) |
| Ig A | 41 (26.8) | 33 (21.4) | 74 (24.1) |
| Ig M | 0 | 2 (1.3) | 2 (0.7) |
| Ig D | 0 | 0 | 0 |
| Ig E | 0 | 0 | 0 |
| Kappa light chain only | 7 (4.6) | 8 (5.2) | 15 (4.9) |
| Lambda light chain only | 4 (2.6) | 7 (4.5) | 11 (3.6) |
| Beta 2-microglobulin (mg/L) | | | |
| Number | 150 | 151 | 301 |
| Mean (SD) | 5.71 (6.72) | 4.68 (3.84) | 5.19 (5.49) |
| Median | 3.75 | 3.40 | 3.60 |
| Min; Max | 0.7; 54.7 | 0.4; 27.0 | 0.4; 54.7 |
| Beta 2-microglobulin (mg/L) [n (%)] | | | |
| Number | 150 | 151 | 301 |
| <3.5 | 65 (43.3) | 77 (51.0) | 142 (47.2) |
| ≥3.5 and <5.5 | 42 (28.0) | 40 (26.5) | 82 (27.2) |
| ≥5.5 | 43 (28.7) | 34 (22.5) | 77 (25.6) |
| Serum LDH [n (%)] | | | |
| Number | 153 | 154 | 307 |
| ≤ULN | 102 (66.7) | 106 (68.8) | 208 (67.8) |
| >ULN | 51 (33.3) | 48 (31.2) | 99 (32.2) |

TABLE G-continued

Disease Characteristics of Randomized Population at Study Entry

|  | Pd (Control Arm) (N = 153) | IPd (Experimental Arm) (N = 154) | All (N = 307) |
|---|---|---|---|
| ISS stage at study entry [n (%)] | | | |
| Number | 153 | 154 | 307 |
| Stage I | 51 (33.3) | 64 (41.6) | 115 (37.5) |
| Stage II | 56 (36.6) | 53 (34.4) | 109 (35.5) |
| Stage III | 43 (28.1) | 34 (22.1) | 77 (25.1) |
| Unknown | 3 (2.0) | 3 (1.9) | 6 (2.0) |
| R-ISS stage at study entry [n (%)] | | | |
| Number | 153 | 154 | 307 |
| Stage I | 31 (20.3) | 39 (25.3) | 70 (22.8) |
| Stage II | 98 (64.1) | 99 (64.3) | 197 (64.2) |
| Stage III | 24 (15.7) | 16 (10.4) | 40 (13.0) |
| Unknown | 0 | 0 | 0 |
| Refractory status | | | |
| Number | 153 | 154 | 307 |
| Relapsed and refractory* | 153 (100) | 154 (100) | 307 (100) |
| Primary refractory | 0 | 0 | 0 |
| Relapsed | 0 | 0 | 0 |

*excluding primary refractory
MM: Multiple Myeloma,
Ig: Immunoglobulin,
LDH: Lactate Dehydrogenase,
ULN: Upper Limit of Normal,
ISS: International staging system,
R-ISS: Revised International staging system Overall, the 2 treatment arms were similar with regards to prior anti-myeloma therapies (see Tables H1 and H2 below). As per protocol, all patients had received at least 2 prior lines of treatment including prior lenalidomide and proteasome inhibitor (PI). Overall, the median number of prior lines was 3 (range 2 to 11 lines), with 107 (34.9%) patients having received 4 or more prior lines of treatment. One patient was previously treated with daratumumab. Ninety two percent of patients were refractory to lenalidomide, 75.9% of patients were refractory to PI and 72.6% of patients were refractory to lenalidomide and PI. Nearly all patients (98.0%) were refractory to the last regimen before study entry.

TABLE H1

Overall Summary of Prior Anti-Myeloma Treatments in the Randomized Population.

|  | Pd (Control Arm) (N = 153) | IPd (Experimental Arm) (N = 154) | All (N = 307) |
|---|---|---|---|
| Number of prior regimens | | | |
| Number | 153 | 154 | 307 |
| Mean (SD) | 4.61 (1.85) | 4.71 (2.20) | 4.66 (2.03) |
| Median | 4.00 | 4.00 | 4.00 |
| Min; Max | 2.0; 11.0 | 2.0; 13.0 | 2.0; 13.0 |
| Number of prior regimens [n (%)] | | | |
| Number | 153 | 154 | 307 |
| 2 | 16 (10.5) | 22 (14.3) | 38 (12.4) |
| 3 | 27 (17.6) | 29 (18.8) | 56 (18.2) |
| 4 | 37 (24.2) | 32 (20.8) | 69 (22.5) |
| 5 | 36 (23.5) | 21 (13.6) | 57 (18.6) |
| 6 | 20 (13.1) | 27 (17.5) | 47 (15.3) |
| 7 | 6 (3.9) | 9 (5.8) | 15 (4.9) |
| ≥8 | 11 (7.2) | 14 (9.1) | 25 (8.1) |

TABLE H1-continued

Overall Summary of Prior Anti-Myeloma Treatments in the Randomized Population.

| | Pd (Control Arm) (N = 153) | IPd (Experimental Arm) (N = 154) | All (N = 307) |
|---|---|---|---|
| Number of prior lines | | | |
| Number | 153 | 154 | 307 |
| Mean (SD) | 3.33 (1.39) | 3.52 (1.73) | 3.42 (1.57) |
| Median | 3.00 | 3.00 | 3.00 |
| Min; Max | 2.0; 10.0 | 2.0; 11.0 | 2.0; 11.0 |
| Number of prior lines [n (%)] | | | |
| Number | 153 | 154 | 307 |
| 2 | 45 (29.4) | 45 (29.2) | 90 (29.3) |
| 3 | 58 (37.9) | 52 (33.8) | 110 (35.8) |
| 4 | 28 (18.3) | 32 (20.8) | 60 (19.5) |
| 5 | 8 (5.2) | 7 (4.5) | 15 (4.9) |
| 6 | 10 (6.5) | 6 (3.9) | 16 (5.2) |
| 7 | 2 (1.3) | 7 (4.5) | 9 (2.9) |
| ≥8 | 2 (1.3) | 5 (3.2) | 7 (2.3) |
| Prior ASCT [n (%)] | 90 (58.8) | 83 (53.9) | 173 (56.4) |
| Main anti-myeloma therapies by class and agent [n (%)] | | | |
| Number | 153 | 154 | 307 |
| Alkylating agents | 148 (96.7) | 139 (90.3) | 287 (93.5) |
| Bendamustine | 9 (5.9) | 8 (5.2) | 17 (5.5) |
| Bendamustine hydrochloride | 0 | 1 (0.6) | 1 (0.3) |
| Busulfan | 1 (0.7) | 1 (0.6) | 2 (0.7) |
| Carmustine | 4 (2.6) | 2 (1.3) | 6 (2.0) |
| Cyclophosphamide | 90 (58.8) | 86 (55.8) | 176 (57.3) |
| Cyclophosphamide monohydrate | 0 | 1 (0.6) | 1 (0.3) |
| Lomustine | 0 | 1 (0.6) | 1 (0.3) |
| Melphalan | 122 (79.7) | 120 (77.9) | 242 (78.8) |
| Melphalan flufenamide | 1 (0.7) | 0 | 1 (0.3) |
| Melphalan hydrochloride | 1 (0.7) | 0 | 1 (0.3) |
| Thiotepa | 1 (0.7) | 0 | 1 (0.3) |
| Treosulfan | 0 | 1 (0.6) | 1 (0.3) |
| Proteasome inhibitors | 153 (100) | 154 (100) | 307 (100) |
| Bortezomib | 150 (98.0) | 150 (97.4) | 300 (97.7) |
| Carfilzomib | 44 (28.8) | 34 (22.1) | 78 (25.4) |
| Ixazomib | 13 (8.5) | 18 (11.7) | 31 (10.1) |
| Ixazomib citrate | 0 | 1 (0.6) | 1 (0.3) |
| Immunomodulators | 153 (100) | 154 (100) | 307 (100) |
| Lenalidomide | 153 (100) | 154 (100) | 307 (100) |
| Pomalidomide | 0 | 1 (0.6) | 1 (0.3) |
| Thalidomide | 71 (46.4) | 70 (45.5) | 141 (45.9) |
| HDAC inhibitors | 7 (4.6) | 4 (2.6) | 11 (3.6) |
| Panobinostat | 6 (3.9) | 4 (2.6) | 10 (3.3) |
| Panobinostat lactate | 1 (0.7) | 0 | 1 (0.3) |
| Anthracyclins | 35 (22.9) | 40 (26.0) | 75 (24.4) |
| Daunorubicin | 0 | 1 (0.6) | 1 (0.3) |
| Doxorubicin | 27 (17.6) | 35 (22.7) | 62 (20.2) |
| Doxorubicin hydrochloride | 3 (2.0) | 1 (0.6) | 4 (1.3) |
| Idarubicin | 4 (2.6) | 1 (0.6) | 5 (1.6) |
| Liposomal doxorubicin hydrochloride | 1 (0.7) | 0 | 1 (0.3) |
| Mitoxantrone | 0 | 1 (0.6) | 1 (0.3) |
| Pegylated liposomal doxorubicin | 1 (0.7) | 1 (0.6) | 2 (0.7) |
| Pegylated liposomal doxorubicin hydrochloride | 1 (0.7) | 0 | 1 (0.3) |
| Corticosteroids | 153 (100) | 154 (100) | 307 (100) |
| Betamethasone | 0 | 1 (0.6) | 1 (0.3) |
| Betamethasone sodium phosphate | 0 | 1 (0.6) | 1 (0.3) |
| Dexamethasone | 149 (97.4) | 153 (99.4) | 302 (98.4) |
| Dexamethasone acetate | 1 (0.7) | 1 (0.6) | 2 (0.7) |
| Dexamethasone sodium phosphate | 1 (0.7) | 1 (0.6) | 2 (0.7) |
| Methylprednisolone | 3 (2.0) | 3 (1.9) | 6 (2.0) |
| Prednisolone | 14 (9.2) | 20 (13.0) | 34 (11.1) |
| Prednisone | 35 (22.9) | 24 (15.6) | 59 (19.2) |
| Vinca alkaloids | 21 (13.7) | 20 (13.0) | 41 (13.4) |
| Vincristine | 20 (13.1) | 17 (11.0) | 37 (12.1) |
| Vincristine sulfate | 1 (0.7) | 3 (1.9) | 4 (1.3) |
| Monoclonal antibodies | 2 (1.3) | 2 (1.3) | 4 (1.3) |
| Daratumumab | 0 | 1 (0.6) | 1 (0.3) |
| Elotuzumab | 2 (1.3) | 1 (0.6) | 3 (1.0) |

TABLE H1-continued

Overall Summary of Prior Anti-Myeloma Treatments in the Randomized Population.

|  | Pd (Control Arm) (N = 153) | IPd (Experimental Arm) (N = 154) | All (N = 307) |
|---|---|---|---|
| Other | 35 (22.9) | 37 (24.0) | 72 (23.5) |
| Intolerance to lenalidomide [n (%)] | 12 (7.8) | 10 (6.5) | 22 (7.2) |
| Intolerance to proteasome inhibitors [n (%)] | 21 (13.7) | 19 (12.3) | 40 (13.0) |
| Intolerance to lenalidomide and proteasome inhibitors [n (%)] | 4 (2.6) | 4 (2.6) | 8 (2.6) |

TABLE H2

Refractory Status of Randomized Population to Prior Anti-Myeloma Therapies.

|  | Pd (Control Arm) (N = 153) | IPd (Experimental Arm) (N = 154) | All (N = 307) |
|---|---|---|---|
| Refractory to IMiD [n (%)] | 144 (94.1) | 147 (95.5) | 291 (94.8) |
| Refractory to lenalidomide | 140 (91.5) | 144 (93.5) | 284 (92.5) |
| Refractory to PI [n (%)] | 115 (75.2) | 118 (76.6) | 233 (75.9) |
| Refractory to bortezomib | 89 (58.2) | 95 (61.7) | 184 (59.9) |
| Refractory to carfilzomib | 40 (26.1) | 28 (18.2) | 68 (22.1) |
| Refractory to ixazomib | 13 (8.5) | 17 (11.0) | 30 (9.8) |
| Refractory to IMiD and PI [n (%)]last | 110 (71.9) | 113 (73.4) | 223 (72.6) |
| Refractory to lenalidomide and bortezomib | 82 (53.6) | 89 (57.8) | 171 (55.7) |
| Refractory to lenalidomide and carfilzomib | 39 (25.5) | 26 (16.9) | 65 (21.2) |
| Refractory to lenalidomide and ixazomib | 11 (7.2) | 17 (11.0) | 28 (9.1) |
| Refractory to lenalidomide, bortezomib, carfilzomib and ixazomib | 0 | 0 | 0 |
| Refractory to last regimen [n (%)] | 151 (98.7) | 150 (97.4) | 301 (98.0) |
| Lenalidomide | 138 (90.2) | 142 (92.2) | 280 (91.2) |
| Bortezomib | 83 (54.2) | 88 (57.1) | 171 (55.7) |
| Carfilzomib | 40 (26.1) | 28 (18.2) | 68 (22.1) |
| Lenalidomide and bortezomib | 76 (49.7) | 81 (52.6) | 157 (51.1) |
| Lenalidomide and carfilzomib | 39 (25.5) | 26 (16.9) | 65 (21.2) |

PI: proteasome inhibitors,
IMiD: Immunomodulators

More than one third of study population (i.e., 36.2%) entered study with renal function impairment (defined as GFR<60 ml/min/1.73 m2). There was a trend towards more patients with impaired renal function entering the IPd arm (38.7%) than the Pd arm (33.8%).

It is well documented that multiple myeloma patients bearing at least one high-risk chromosomal abnormality (CA), such as del(17p), translocation t(4;14) and/or translocation t(14;16), have a poorer prognosis compared to patients without high-risk CAs. Accordingly, high-risk chromosomal abnormalities were assessed at baseline in some patients. Twenty one percent of the patients were not evaluable for CAs, which is within the ranges of what is generally reported for assessments in MM studies. The percentage of patients with high-risk CAs was lower in the IPd arm compared with the Pd arm (15.6% versus 23.5%). Eight (2.6%) patients (5 in Pd arm and 3 in IPd arm) had 2 high-risk cytogenetic abnormalities (see Table I). Such patient population has very poor prognosis.

TABLE I

Cytogenetics of Randomized Population at Study Entry

|  | Pd (Control Arm) (N = 153) | IPd (Experimental Arm) (N = 154) | All (N = 307) |
|---|---|---|---|
| Cytogenetic risk at baseline |  |  |  |
| High risk CA[a] | 36 (23.5) | 24 (15.6) | 60 (19.5) |
| Standard risk CA | 78 (51.0) | 103 (66.9) | 181 (59.0) |
| Unknown or missing | 39 (25.5) | 27 (17.5) | 66 (21.5) |
| del (17 p)[b] |  |  |  |
| Present | 23 (15.0) | 14 (9.1) | 37 (12.1) |
| Absent | 95 (62.1) | 118 (76.6) | 213 (69.4) |
| Unknown or missing | 35 (22.9) | 22 (14.3) | 57 (18.6) |
| t (4; 14)[b] |  |  |  |
| Present | 14 (9.2) | 12 (7.8) | 26 (8.5) |
| Absent | 101 (66.0) | 119 (77.3) | 220 (71.7) |
| Unknown or missing | 38 (24.8) | 23 (14.9) | 61 (19.9) |
| t (14; 16)[b] |  |  |  |
| Present | 4 (2.6) | 1 (0.6) | 5 (1.6) |
| Absent | 119 (77.8) | 135 (87.7) | 254 (82.7) |
| Unknown or missing | 30 (19.6) | 18 (11.7) | 48 (15.6) |

TABLE I-continued

Cytogenetics of Randomized Population at Study Entry

| | Pd (Control Arm) (N = 153) | IPd (Experimental Arm) (N = 154) | All (N = 307) |
|---|---|---|---|
| High risk cytogenetic abnormalities | | | |
| del (17 p) and t (4; 14) | 4 (2.6) | 3 (1.9) | 7 (2.3) |
| del (17 p) and t (14; 16) | 1 (0.7) | 0 | 1 (0.3) |

CA: Chromosomal abnormalities
[a]High risk CA is defined as the presence of del(17 p) and/or translocation t (4; 14) and/or translocation t (14; 16)
[b]Abnormality was considered positive if present in at least 30% of analyzed plasma cells, except for del (17 p) where the threshold is at least 50%

B. Dosage and Duration of Exposure to Study Treatments

Duration of exposure was almost twice as long in the IPd arm compared with the Pd arm. The median duration of exposure was 41 weeks (range 1.3 to 76.7) in the IPd arm and 24 weeks (range 1 to 73.7) in the Pd arm. Fifty-five patients (36.2%) in IPd arm and 38 patients (25.5%) in Pd arm received ≥12 cycles. In the IPd arm, the median number of isatuximab cycles was 10 (range 1 to 19), with a median duration of isatuximab exposure of 40.9 weeks (range 1.0 to 75.1 weeks) and 35.5% of the patients received ≥12 cycles of isatuximab. See Table J. The median relative dose intensity (RDI) of isatuximab was 92.3% (range=19.7%-111.1%). The median RDI of pomalidomide and dexamethasone was 85.1% (pomalidomide) and 87.8% (dexamethasone) in the IPd arm, and 93.3% (pomalidomide) and 96.3% (dexamethasone) in the Pd arm.

Isatuximab dose omissions and dose delays were reported in 52% and 10.5% of patients, respectively. Infusion interruptions of isatuximab occurred in 34.9% of patients and 2.1% of isatuximab infusions as part of the management of infusion reaction. Dose interruptions occurred generally only once with the exception of 6 patients. Nearly all of the infusion interruptions occurred at the first infusion. The median RDI of pomalidomide was slightly lower in IPd arm versus Pd arm (85.1% (range=22.9%-103.7%) in the IPd arm and 93.3% (range=37.2%-118.5%) in the Pd arm). The median RDI of dexamethasone was slightly lower in IPd arm versus Pd arm (87.8% (range=15.9%-130%) in the IPd arm and 96.3% (range=30.3%-300%) in the Pd arm). The RDI of pomalidomide and dexamethasone was driven by dose reductions and omissions for the management of neutropenia and infections.

TABLE J

Duration of Exposure to Study Treatments

| | Pd (Control Arm) (N = 149) | IPd (Experimental Arm) (N = 152) |
|---|---|---|
| Total number of cycles started | 1078 | 1391 |
| Cumulative exposure to treatment (patient years) | 83.75 | 110.15 |
| Number of cycles started by patient | | |
| Number | 149 | 152 |
| Mean (SD) | 7.23 (4.91) | 9.15 (4.88) |
| Median | 6.00 | 10.00 |
| Min; Max | 1.0; 18.0 | 1.0; 19.0 |
| Number of cycles started by patient [n (%)] | | |
| At least 1 cycle | 149 (100) | 152 (100) |
| At least 2 cycles | 131 (87.9) | 144 (94.7) |
| At least 3 cycles | 115 (77.2) | 136 (89.5) |
| At least 4 cycles | 105 (70.5) | 124 (81.6) |
| At least 5 cycles | 89 (59.7) | 113 (74.3) |
| At least 6 cycles | 79 (53.0) | 109 (71.7) |
| At least 7 cycles | 71 (47.7) | 100 (65.8) |
| At least 8 cycles | 63 (42.3) | 95 (62.5) |
| At least 9 cycles | 60 (40.3) | 91 (59.9) |
| At least 10 cycles | 57 (38.3) | 81 (53.3) |
| At least 11 cycles | 49 (32.9) | 69 (45.4) |
| At least 12 cycles | 38 (25.5) | 55 (36.2) |
| At least 13 cycles | 29 (19.5) | 39 (25.7) |
| At least 14 cycles | 16 (10.7) | 27 (17.8) |
| At least 15 cycles | 13 (8.7) | 22 (14.5) |
| At least 16 cycles | 10 (6.7) | 17 (11.2) |
| At least 17 cycles | 3 (2.0) | 10 (6.6) |
| At least 18 cycles | 1 (0.7) | 6 (3.9) |
| At least 19 cycles | 0 | 1 (0.7) |
| Duration of exposure (weeks) | | |
| Number | 149 | 152 |
| Mean (SD) | 29.33 (20.57) | 37.81 (20.29) |
| Median | 24.00 | 41.00 |
| Min; Max | 1.0; 73.7 | 1.3; 76.7 |

C. Efficacy i. Progression Free Survival (PFS)

Figure 2:
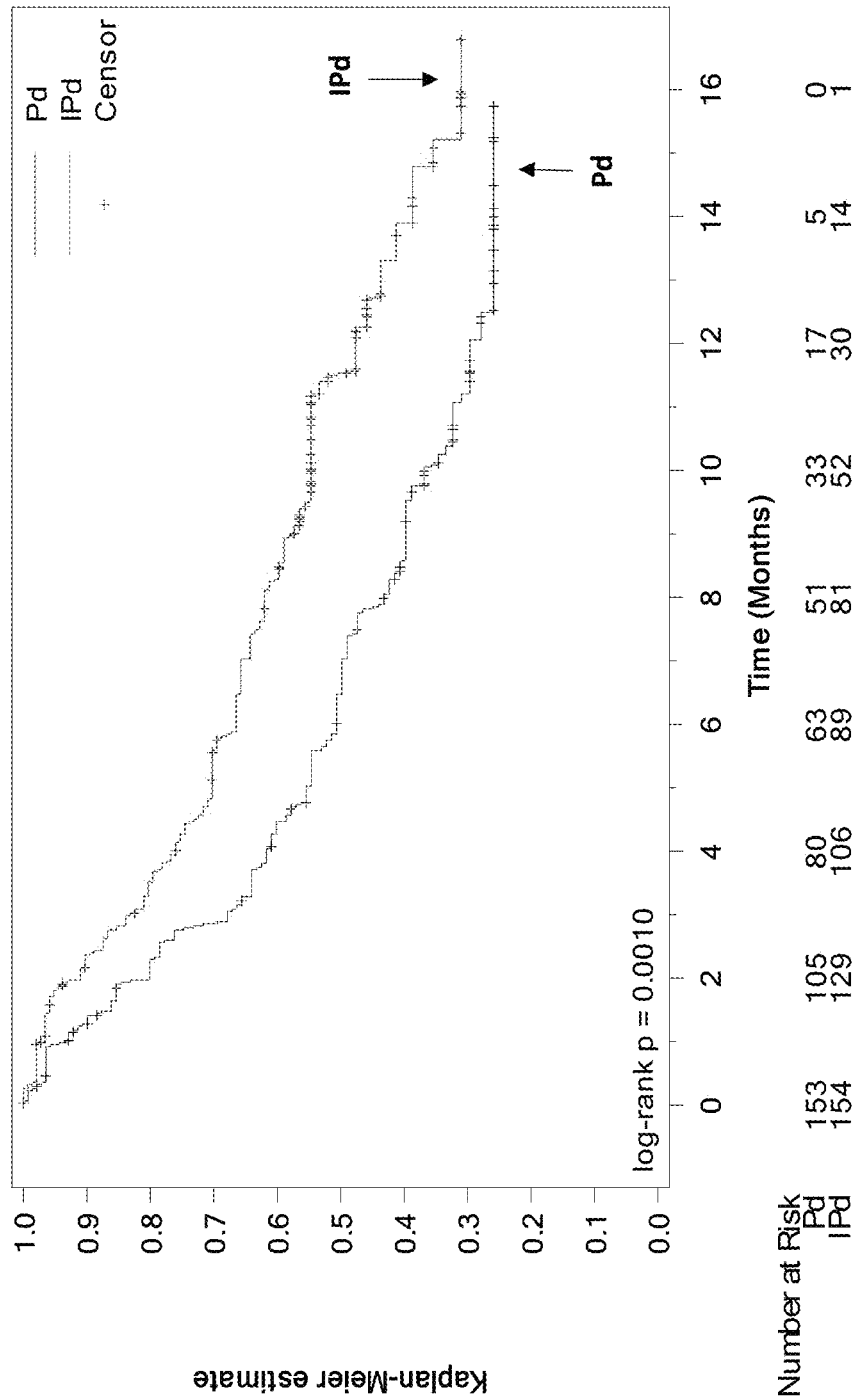
FIG. 2 provides a Kaplan-Meier Plot of progression-free survival (PFS) of patients in the IPd arm (isatuximab+pomalidomide+dexamethasone) vs. the Pd arm (pomalidomide+dexamethasone), as assessed by the Independent Response Committee (IRC).

Patients who received treatment with isatuximab+pomalidomide+dexamethasone (IPd) demonstrated significantly increased progression-free survival (PFS), compared to patients who received treatment with pomalidomide+dexamethasone (Pd), as assessed by the Independent Response Committee (IRC). See FIG. 2. The stratified log rank test resulting from the comparison of PFS between the 2 arms was statistically significant with a p-value of 0.001. Eighty-nine (58.2%) and 73 (47.4%) PFS events were reported in the Pd and IPd groups, respectively. Median PFS was longer in the IPd arm (11.53 months, 95% CI: 8.936 to 13.897) than in the Pd arm (6.47 months, 95% CI: 4.468 to 8.279), respectively. The stratified hazard ratio was 0.596 (95% CI: 0.436 to 0.814, p=0.0010) characterizing a reduction of 40% in risk for disease progression or death with IPd compared to Pd. IRC assessment of progression and response were based on central laboratory assessments of M protein and central radiology review of imaging, and applying International Myeloma Working Group (IMWG) criteria (see Table A and Table B).

Figure 3:
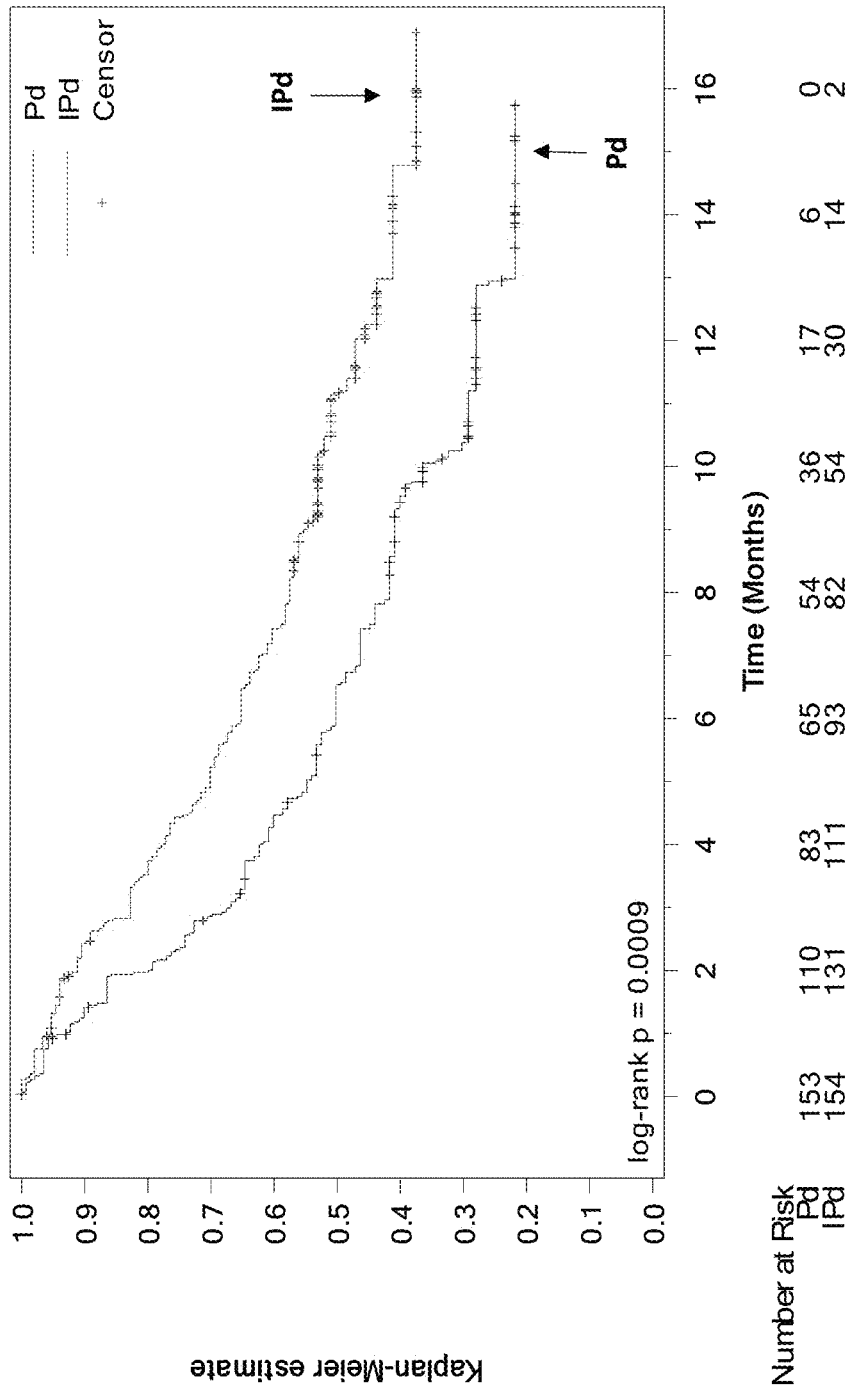
FIG. 3 provides a Kaplan-Meier Plot of progression-free survival (PFS) of patients in the IPd arm (isatuximab+ pomalidomide+dexamethasone) vs. the Pd arm (pomalidomide+dexamethasone), as assessed by the Investigator.

Sensitivity analyses were performed in order to assess the robustness of the primary endpoint analysis with different efficacy assessment method (investigator) or different censoring rules. The results of all sensitivity analyses of PFS are very consistent with the primary PFS analysis results, with statistically significance in favor of IPd arm. In particular, PFS based on the Investigator assessment (see FIG. 3) was consistent with the PFS based on IRC assessment. Investigator assessment of progression was based on local laboratory M-protein analysis and local radiology evaluation of plasmacytomas/bone lesions if any. The median PFS, as assessed by the Investigator, was 11.14 months (95% CI: 7.491 to 14.784) in the IPd arm compared to 6.54 months (95% CI: 4.468 to 7.885) in the Pd arm. The stratified hazard ratio was 0.602 (95% CI: 0.444 to 0.816; p=0.0009).

ii. Subgroup Analyses on PFS

The consistency of treatment effect on PFS was evaluated with respect to predefined demographics, baseline characteristics and prognostic factors. Pre-specified subgroup analyses showed no significant interaction at the 10% level between treatment arms and stratification factors, between treatment arms and demographic characteristics, or between treatment arms and patients' baseline characteristics, indicating an overall consistent treatment effect across those subgroups. As shown in Table K, subgroup analyses on PFS showed positive treatment effect in all subgroups consistent with the overall treatment effect (including subgroups with poor prognosis, e.g., Age >75; HR=0.479; >3 prior lines of therapy: HR=0.59; Renal function impaired: HR=0.51; ISS stage III: HR=0.635; R-ISS stage III: HR=0.605; High risk cytogenetics HR=0.655).

was 11.6 months in the IPd arm vs. 5.7 months in the Pd arm). Patients with high-risk cytogenetics treated with IPd also demonstrated PFS benefit, as compared to patients with high-risk cytogenetics in the Pd arm. (High-risk cytogenetics was defined as del(17p), t(4;14), or t(14;16) by FISH; Cytogenetics by central lab—cut-off 50% for del17, 30% for t(4,14) and t(14,16).) In patients with high-risk cytogenetics, median PFS was 7.5 (95% CI: 2.628 to NC) in the IPd arm and 3.745 (95% CI: 2.793 to 7.885) in the Pd arm. See also FIG. 5, which provides a Forest Plot showing subgroup analyses of PFS in patients with various baseline characteristics (e.g., age, eGFR, prior lines of therapy, previous ASCT, etc.) in the IPd arm vs. the PD arm. PFS benefits improvements in the IPd arm were also observed in patients ≥75 years of age, with ISS stage III at study entry, with baseline creatinine clearance (eGFR)<60 ml/min/1.73 m², with >3 prior lines of therapy, in patients refractory to prior

TABLE K

Progression Free Survival - Summary of Subgroup Analyses

| | Pd (Control Arm) (N = 153) | | | IPd (Experimental Arm) (N = 154) | | | |
|---|---|---|---|---|---|---|---|
| | N | N (%) of Events | Median (Months) (95% CI) | N | N (%) of Events | Median (Months 5% CI) | Hazard Ratio (95% CI) vs Pd |
| All patients | 153 | 89 (58.2) | 6.472 (4.468 to 8.279) | 154 | 73 (47.4) | 11.532 (8.936 to 13.897) | 0.596 (0.436 to 0.814) |
| Age | | | | | | | |
| Age <65 | 70 | 41 (58.6) | 5.027 (3.285 to 8.279) | 54 | 26 (48.1) | 11.532 (4.567 to 14.784) | 0.656 (0.401 to 1.074) |
| Age [65-75] | 54 | 29 (53.7) | 8.575 (4.567 to 12.057) | 68 | 32 (47.1) | 11.565 (8.279 to NC) | 0.638 (0.385 to 1.059) |
| Age ≥75 | 29 | 19 (65.5) | 4.468 (2.595 to 7.754) | 32 | 15 (46.9) | 11.400 (4.435 to NC) | 0.479 (0.242 to 0.946) |
| Number of prior lines of therapy (IRT) | | | | | | | |
| 2 or 3 | 101 | 57 (56.4) | 7.819 (5.027 to 10.086) | 102 | 44 (43.1) | 12.255 (8.969 to NC) | 0.590 (0.397 to 0.878) |
| >3 | 52 | 32 (61.5) | 4.271 (2.563 to 8.575) | 52 | 29 (55.8) | 9.396 (4.830 to 14.784) | 0.590 (0.356 to 0.977) |
| Baseline creatinine clearance (MDRD) | | | | | | | |
| ≥60 ml/min | 94 | 55 (58.5) | 7.885 (5.651 to 10.086) | 86 | 36 (41.9) | 12.715 (8.936 to NC) | 0.576 (0.378 to 0.877) |
| <60 ml/min | 47 | 27 (57.4) | 3.811 (2.858 to 7.819) | 54 | 29 (53.7) | 11.400 (7.491 to 13.897) | 0.510 (0.298 to 0.872) |
| ISS staging at study entry | | | | | | | |
| I | 51 | 28 (54.9) | 9.758 (7.754 to 12.485) | 64 | 25 (39.1) | 13.306 (11.203 to NC) | 0.657 (0.383 to 1.128) |
| II | 56 | 32 (57.1) | 5.027 (2.858 to 10.053) | 53 | 23 (43.4) | 11.532 (5.782 to NC) | 0.541 (0.315 to 0.929) |
| III | 43 | 27 (62.8) | 3.285 (1.971 to 5.585) | 34 | 24 (70.6) | 6.472 (2.760 to 9.495) | 0.635 (0.363 to 1.110) |
| R-ISS staging at study entry | | | | | | | |
| I | 31 | 17 (54.8) | 10.382 (7.754 to NC) | 39 | 13 (33.3) | 14.784 (11.203 to NC) | 0.584 (0.283 to 1.205) |
| II | 98 | 57 (58.2) | 6.472 (4.041 to 9.528) | 99 | 47 (47.5) | 11.499 (7.491 to 15.211) | 0.587 (0.398 to 0.868) |
| III | 24 | 15 (62.5) | 1.971 (1.248 to 3.285) | 16 | 13 (81.3) | 2.793 (1.840 to 9.495) | 0.605 (0.280 to 1.307) |
| Cytogenetic risk | | | | | | | |
| High risk | 36 | 22 (61.1) | 3.745 (2.793 to 7.885) | 24 | 14 (58.3) | 7.491 (2.628 to NC) | 0.655 (0.334 to 1.283) |
| Standard risk | 78 | 48 (61.5) | 7.425 (4.468 to 9.758) | 103 | 50 (48.5) | 11.565 (8.542 to 13.897) | 0.624 (0.418 to 0.930) |

CI: Confidence interval,
ISS: International staging system,
R-ISS: Revised International staging system The PFS benefit with isatuximab was seen in all subgroups, including patients with poor prognosis. PFS benefit was shown in patients refractory to lenalidomide (median PFS was 11.4 months in the IPd arm vs. 5.6 months in the Pd control arm), patients refractory to a proteasome inhibitor (median PFS was 11.4 in the IPd arm vs. 5.6 months in the Pd arm), patients refractory to both lenalidomide and a proteasome inhibitor (median PFS was 11.2 in the IPd arm vs. 4.8 months in the Pd arm), and patients refractory to lenalidomide at the last line prior to study entry (median PFS therapy with lenalidomide or a proteasome inhibitor, and in patients refractory to lenalidomide at the last line before study entry.

iii. Overall Response Rate (ORR)

In the analysis based on investigator assessment, the ORR (i.e., partial response (PR) or better) was significantly higher in the IPd arm than in the Pd arm (60.4% versus 35.3%, respectively). The stratified Cochran-Mantel-Haenszel (CMH) p-value was <0.0001, demonstrating a significant difference in ORR between the two arms in favor of IPd at the 0.025 level. The depth of response was improved in the IPd arm. VGPR or better was achieved in 31.8% and 8.5% in the IPd and Pd arms, respectively (P<0.0001), and more patients in the IPd group than in the Pd arm had a complete response or better (4.5% versus 2.0%). See Table L1, which provides the results of a further analysis of ORR in the IPd and Pd arms.

TABLE L1

Overall response rate as per IRC assessment - ITT population

| | Pd (N = 153) | IPd (N = 154) |
|---|---|---|
| Best Overall Response [n (%)] | | |
| Stringent complete response | 1 (0.7) | 0 |
| Complete response | 2 (1.3) | 7 (4.5) |
| Very good partial response | 10 (6.5) | 42 (27.3) |
| Biochemical CR but with missing bone marrow[a] | 2 (1.3) | 9 (5.8) |
| Near-CR | 5 (3.3) | 24 (15.6) |
| Partial response | 41 (26.8) | 44 (28.6) |
| Minimal response | 17 (11.1) | 10 (6.5) |
| Stable disease | 45 (29.4) | 33 (21.4) |
| Non Progressive Disease | 3 (2.0) | 4 (2.6) |
| Progressive disease | 14 (9.2) | 6 (3.9) |
| Unconfirmed progressive disease | 4 (2.6) | 1 (0.6) |
| Not evaluable/Not assessed | 16 (10.5) | 7 (4.5) |
| Overall Response | | |
| Responders (sCR, CR, VGPR or PR) | 54 (35.3) | 93 (60.4) |
| 95% CI | 0.2775 to 0.4342 | 0.5220 to 0.6817 |
| Stratified Cochran-Mantel-Haenszel test p-value vs Pd | | <0.0001 |
| VGPR or better | 13 (8.5) | 49 (31.8) |
| 95% CIo | 0.0460 to 0.1409 | 0.2455 to 0.3980 |
| Stratified Cochran-Mantel-Haenszel test p-valued vs Pd | | <0.0001 |

[a]Estimated using Clopper-Pearson method;
CI: Confidence interval,
IRC: Independent Response Committee Response rates based on investigator assessment (overall response rate: 63.0% in IPd arm versus 32.0% in Pd arm, and at least VGPR rate of 33.8% in IPd arm versus 7.2% in Pd arm) were consistent with IRC assessments.

As shown in Table L2, subgroup analyses on ORR showed a trend toward positive treatment effect in the IPd arm in all subgroups tested, consistent with the overall treatment effect (including subgroups with poor prognosis, e.g., Age >75; >3 prior lines of therapy; renal function impaired; ISS stage III; R-ISS stage III; and High risk cytogenetics). The number of patients with impaired renal function (i.e., creatinine clearance <60 ml/min/1.73 m$^2$) achieving VGPR or better was higher in the IPd arm than the Pd arm (32.7% in the IPd arm vs. 4.1 in the Pd arm).

TABLE L2

Response Rates in Various Subgroups.

| | Pom/dex (N = 153) | | Isa + Pom/dex (N = 154) | |
|---|---|---|---|---|
| | N | ORR [n, %] | N | ORR [n, %] |
| Age (eCRF) | | | | |
| Age. <65 | 70 | 24 (34.3) | 54 | 32 (59.3) |
| Age [65-75[ | 54 | 21 (38.9) | 68 | 44 (64.7) |
| Age ≥75 | 29 | 9 (31.0) | 32 | 17 (53.1) |
| Number of prior lines of therapy | | | | |
| 2 or 3 | 101 | 39 (38.6) | 102 | 58 (56.9) |
| >3 | 52 | 15 (28.8) | 52 | 35 (67.3) |
| Renal function | | | | |
| ≥60 mL/Min/1.73 m$^2$ | 94 | 41 (43.6) | 86 | 59 (68.6) |
| <60 mL/min/1.73 m$^2$ | 49 | 12 (24.5) | 55 | 31 (56.4) |
| ISS staging at study entry | | | | |
| I | 51 | 23 (45.1) | 64 | 42 (65.6) |
| II | 56 | 20 (35.7) | 53 | 34 (64 2) |
| III | 43 | 10 (23.3) | 34 | 15 (44.1) |
| R-ISS staging at study entry | | | | |
| I | 31 | 16 (51.6) | 39 | 28 (71 8) |
| II | 98 | 36 (36.7) | 99 | 60 (60.6) |
| III | 24 | 2 (8.3) | 16 | 5 (31.3) |
| Cytogenetic risks | | | | |
| High risk | 36 | 6 (16.7) | 24 | 12 (50.0) |
| Standard risk | 78 | 33 (42.3) | 103 | 67 (65.0 | iv. Treatment Impact on Renal Dysfunction

Patients with renal impairment are often excluded from or underrepresented in clinical trials. Further, few data exist exploring renal impairment among patients receiving monoclonal antibody therapy. Renal impairment is an independent predictor of poor prognosis in patients with RRMM, and there is a critical need for anti-myeloma therapies that also improve renal function.

In the present study the number of patients with impaired renal function at baseline (i.e., baseline creatinine clearance (MDRD)) was evenly balanced between the two arms (49 in the Pd arm vs. 55 in the IPd arm). See Table L3, which provides the baseline demographics and clinical characteristics of patients who had renal impairment at the start of the study.

TABLE L3

| | eGFR <60 mL/min/1.73 m² | | eGFR ≥60 mL/min/1.73 m² | |
|---|---|---|---|---|
| Baseline demographics and clinical characteristics of patients with renal impairment | Isa-Pd (n = 55) | Pd (n = 49) | Isa-Pd (n = 87) | Pd (n = 96) |
| Median age, years (range) | 71 (39-83) | 67 (41-86) | 66 (36-82) | 64 (41-81) |
| Age categories, n (%) | | | | |
| <65 years | 15 (27.3) | 18 (36.7) | 34 (39.1) | 49 (51.0) |
| 65-75 years | 21 (38.2) | 16 (32.7) | 42 (48.3) | 35 (36.5) |
| ≥75 years | 19 (34.5) | 15 (30.6) | 11 (12.6) | 12 (12.5) |
| Median time since diagnosis, years (range) | 4.4 (1.3-11.1) | 4.5 (1.2-15.8) | 4.9 (0.6-18.4) | 4.0 (0.5-20.5) |
| Type of myeloma at diagnosis, n (%) | | | | |
| IgA | 16 (29.1) | 9 (18.4) | 16 (18.4) | 30 (31.3) |
| IgG | 30 (54.5) | 34 (69.4) | 63 (72.4) | 60 (62.5) |
| Light chain (κ + λ) | 7 (12.7) | 6 (12.2) | 7 (8.0) | 5 (5.2) |
| ISS stage[a] at diagnosis, n (%) | | | | |
| I | 7 (12.7) | 9 (18.4) | 27 (31.0) | 29 (30.2) |
| II | 14 (25.5) | 15 (30.6) | 30 (34.5) | 30 (31.3) |
| III | 23 (41.8) | 19 (38.8) | 16 (18.4) | 24 (25.0) |
| ISS stage[a] at study entry, n (%) | | | | |
| I | 14 (25.5) | 7 (14.3) | 45 (51.7) | 42 (43.8) |
| II | 16 (29.1) | 16 (32.7) | 32 (36.8) | 36 (37.5) |
| III | 25 (45.5) | 25 (51.0) | 7 (8.0) | 16 (16.7) |
| Cytogenetic risk at study entry[b], n (%) | | | | |
| High | 9 (16.4) | 11 (22.4) | 11 (12.6) | 22 (22.9) |
| Standard | 36 (65.5) | 29 (59.2) | 63 (72.4) | 47 (49.0) |
| Missing | 10 (18.2) | 9 (18.4) | 13 (14.9) | 27 (28.1) |
| Median prior lines of therapy (range) | 3 (2-11) | 3 (2-10) | 3 (2-11) | 3 (2-9) |
| Prior therapy, n (%) | | | | |
| Alkylating agent | 49 (89.1) | 47 (95.9) | 80 (92.0) | 93 (96.9) |
| Proteasome inhibitor | 55 (100) | 49 (100) | 87 (100) | 96 (100) |
| Lenalidomide | 55 (100) | 49 (100) | 87 (100) | 96 (100) |
| Refractory status, n (%) | | | | |
| IMiD refractory | 52 (94.5) | 44 (89.8) | 83 (95.4) | 92 (95.8) |
| Lenalidomide refractory | 51 (92.7) | 42 (85.7) | 81 (93.1) | 90 (93.8) |
| PI refractory | 41 (74.5) | 42 (85.7) | 70 (80.5) | 69 (71.9) |
| Lenalidomide and PI refractory | 39 (70.9) | 37 (75.5) | 65 (74.7) | 66 (68.8) |
| Lenalidomide last line | 35 (63.6) | 22 (44.9) | 48 (55.2) | 59 (61.5) |

[a]ISS staging was derived based on the combination of serum β$_2$-microglobulin and albumin

[b]High risk was defined as del (17 p), t (4; 14), or t (14; 16) by fluorescence in situ hybridization. Cytogenetics was performed by a central laboratory with a cut-off of 50% for del (17 p), and 30% for t (4; 14) and t (14; 16)

eGFR estimated glomerular filtration rate,

Ig immunoglobulin,

Isa isatuximab,

ISS International Staging System,

IMiD immunomodulatory drug,

Pd pomalidomide and dexamethasone,

PI proteasome inhibitor

The number of patients who demonstrated improved renal function following the start of treatment was significantly higher in the IPd arm than in the Pd arm. 23 patients (16.4%) in the IPd arm achieved a complete renal response as compared to 8 patients (5.7%) in the Pd arm. An additional patient (0.7) in the IPd arm achieved a minor renal response, i.e., an eGFR increase >50%, either from <15 mL/min to 15-<30 mL/min or from 15-<30 mL/min to 30-<60 mL/min). Fewer patients in the IPd arm experienced worsening to severe or end-stage renal function than in the Pd arm (23% in the IPd arm vs. 35% in the Pd arm).

TABLE M1

Treatment Impact on Renal Function

|  | Isa-Pd (n = 154) | Pd (n = 153) |
|---|---|---|
| Patients with creatinine clearance <50 ml/min/1.73 m² at baseline | 32* | 21* |
| Complete renal response | 23/32 (71.9%) | 8/21 (38.1%) |
| Sustained complete renal response | 10/32 (31.3%) | 4/21 (19.0%) |

*Number of patients with both baseline and at least one post-baseline assessment.
CrCl = creatinine clearance;
d = dexamethasone;
Isa = isatuximab;
P = pomalidomide
Complete renal response: defined as an improvement from <50 ml min/1.73 m2 at baseline to at least one assessment ≥60 ml/min during treatment
Sustained complete renal response: defined as an improvement from <50 ml/min/1.73 m2 at baseline to at least one assessment ≥60 ml/min during treatment for at least 60 days As shown in Table M1, of the 32 patients in the IPd arm with creatinine clearance <50 ml/min/1.73 m² at baseline, 23 (71.9%) showed a complete renal response, and 10 (31.3%) showed a sustained complete renal response. By contrast, of the 21 patients in the Pd arm with creatinine clearance <50 ml/min/1.73 m² at baseline, 8 (38.1%) showed complete renal response, and 4 (19%) showed sustained complete renal response. A complete renal response (CRenal) was characterized as an improvement in creatinine clearance from <50 mL/min/1.73 m² at baseline to ≥60 mL/min/1.73 m² at ≥1 post-baseline assessment. A durable (sustained) CRenal was characterized as a Crenal response was a response that was sustained for ≥60 days (see Dimopoulos, et al., *Blood*, 2013; 122: 3176). Median time to first complete renal response (CRenal) was 4.1 weeks in the IPd arm and 7.3 weeks in the Pd arm. CRenal and lasted for a median 57.0 days in the IPd arm and 59.5 days in the Pd arm.

For patients with impaired renal function at baseline, the median PFS for patients in the IPD arm was 9.5 months, whereas the median PFS for patients in the Pd arm was 3.7 months (HR of 0.50; 95% CI 0.30-0.85). For patients with eGFR<45 mL/min/1.73 m², the median PFS for patients in the IPD arm was 7.5 months, whereas the median PFS for patients in the Pd arm was 2.8 months with Pd (HR of 0.50; 95% CI 0.22-1.13). In patients without impaired renal function at base line, the median PFS for patients in the IPD arm (n=87) was 12.7 months, whereas the median PFS for patients in the Pd arm (n=96) was 7.9 months (HR of 0.58; 95% CI 0.38-0.88).

The overall response rate (ORR) was higher in patients treated with IPd than in patients treated with Pd, regardless of renal function at baseline. For patients without renal impairment at baseline, the ORR was 67.8% (4.6% CR, 29.9% VGPR, and 33.3% PR) in the IPd arm (n=87) and 42.7% (1% sCR, 1% CR, 9.4% VGPR, and 31.3% PR) in the Pd arm n=96). For patients with renal impairment at baseline (eGFR<60 ml/min/1.73 m²), the ORR was 56.4% (5.5% CR, 27.3% VGPR, 23.6% PR) in the IPd arm (n=55) and 24.5% (2% CR, 2% VGPR, 20.4% PR) in the Pd arm (n=49) (odds ratio [OR]3.98; 95% CI 1.60-10.17). For patients with eGFR≥45-<60 ml/min/1.73 m² at baseline, the ORR was 68.6% (5.7% CR, 31.4% VGPR, 31.4% PR) in the IPd arm (n=35) and 25% (3.1% CR, 3.1% VGPR, 18.8% PR) in the Pd arm (n=32). For patients with eGFR<45 mL/min/1.73 m² at baseline, the ORR was 35.0% (5% CR, 20% VGPR, 10% PR) in the IPd arm (n=20) and 23.5% (23.5% PR) in the Pd arm (n=17) (OR 1.75; 95% CI 0.34-10.11). Among the patients with eGFR<45 mL/min/1.73 m² at baseline one patient in each arm had eGFR<30 ml/min/1.73 m²; the patient in the IPd arm had SD (stable disease), whereas the patient in the Pd arm had PD (progressive disease).

Three patients with renal impairment in the IPd arm obtained minimal residual disease negativity (MRD negativity) (sensitivity level 1 in $10^5$).

Median OS for patients with renal impairment at baseline was not reached in the IPd arm, whereas median OS was 11.6 months in the Pd arm (HR 0.53; 95% CI 0.30-0.96). For patients with eGFR<45 mL/min/1.73 m², median OS was 10.7 in the IPd arm versus 6.6 months in the Pd arm (HR 0.62; 95% CI 0.26-1.45). In patients without renal impairment at baseline, median OS was not reached in either arm (HR 0.62; 95% CI 0.33-1.19).

The number of patients who developed end-stage renal disease (ESRD; eGFR<15 mL/min/1.73 m²) on treatment was lower in the IPd arm (2.9%) than in the Pd arm (7.9%). Among patients with moderate RI at baseline, renal function worsened to severe RI or ESRD in 22.6% (12/53) of patients in the Isa-Pd arm and 34.8% (16/46) of patients in the Pd arm [OR 0.55; 95% CI, 0.20-1.45]).

Treatment with IPd improved PFS and disease response rates in patients with renal impairment at baseline, including in patients with eGFR<45 mL/min/1.73 m², as compared to treatment with Pd. These results are consistent with the benefit observed in the overall study population. Compared to treatment with Pd, treatment with IPd was also associated with an increased number of patients with reversal of renal impairment and with durable renal responses. Pharmacokinetic parameters were comparable between patients with renal impairment and those without, suggesting no need for dose adjustment in patients with renal impairment. Based on these data, the addition of isatuximab to pomalidomide+dexamethasone is expected to benefit patients with RRMM and renal impairment.

v. Treatment Impact on Patients with High-Risk Cytogenetic Abnormalities

The overall response rate (ORR) benefit observed in the IPd arm vs. the Pd arm was maintained among patients with at least one high-risk cytogenetic abnormality at baseline (i.e., one or more of del(17p), t(4;14), and t(14;16)). Among patients with standard risk cytogenetics at baseline, the ORR was 65% (3.9% CR, 28.2% VGPR, 33% PR) in the IPd arm (n=103), whereas the ORR was 42.3% (1.3% CR, 7.7% VGPR, and 33.3% PR) in the Pd arm (n=78). Among patients with at least one high-risk cytogenetic abnormality at baseline, the ORR was 50.0% (29.2% VGPR, 20.8% PR) in the IPd arm (n=24), whereas the ORR was 16.7% (2.8% VGPR, 13.9% PR) in the Pd arm (n=36). Among patients with del (17p) and 4(4; 14) cytogenetic abnormalities at baseline, 1 patient in the IPd arm (n=3) achieved VGPR, and 1 patient in the Pd arm (n=4) achieved PR. Data regarding the odds ratio for response rate are provided in Table M2 below:

TABLE M2

| | Isa-Pd vs Pd odds ratio (95% CI) | |
| --- | --- | --- |
| | High risk | Standard risk |
| ORR | 5.00 | 2.54 |
| | (1.33-19.79) | (1.33-4.86) |
| ≥VGPR | 14.41 | 4.78 |
| | (1.57-667.48) | (1.90-13.57) |

The ORR benefit of treatment with IPd vs. Pd in patients with at least one high-risk cytogenetic abnormality at baseline is maintained regardless of the high-risk cytogenetic cut-off definition used. The ORR benefit of treatment with IPd vs. Pd in was observed in patients who were classified as del(17p) according to any one of the following cutoff definitions: at least 5% of plasma cells, at least 20% of plasma cells, at least 40% of plasma cells, at least 50% of plasma cells, or at least 60% of plasma cells. The ORR benefit of treatment with IPd vs. Pd in was observed in patients who were classified as t(4;14) according to any one of the following cutoff definitions at least 3%, of plasma cells, at least 20%, of plasma cells, at least 30%, of plasma cells, at least 40%, of plasma cells, or at least 60%, of plasma cells of plasma cells.

The PFS benefit observed in the IPd arm vs. the Pd arm was maintained among patients with at least one high-risk cytogenetic abnormality at baseline (i.e., one or more of del(17p), t(4;14), and t(14;16)). In the IPd arm, the median PFS for patients with standard-risk cytogenetics at baseline was 11.6 months, whereas in the Pd arm, the median PFS for patients with standard-risk cytogenetics at baseline was 7.4 months. In the IPd arm, the median PFS for patients with high-risk cytogenetics at baseline was 7.5 months, whereas in the Pd arm, the median PFS for patients with high-risk cytogenetics at baseline was 3.7 months. For patients with del(17p) at baseline, the median PFS was 9.1 months in the IPd arm vs. 7.4 months in the Pd arm. For patients with t(4;14) at baseline, the median PFS was 7.5 months in the IPd arm vs. 2.8 months in the Pd arm. The PFS benefit of treatment with IPd vs. Pd in was observed in patients who were classified as del(17p) according to any one of the following cutoff definitions: at least 5% of plasma cells, at least 20% of plasma cells, at least 40% of plasma cells, at least 50% of plasma cells, or at least 60% of plasma cells. The PFS benefit of treatment with IPd vs. Pd in was observed in patients who were classified as t(4;14) according to any one of the following cutoff definitions at least 3%, of plasma cells, at least 20%, of plasma cells, at least 30%, of plasma cells, at least 40%, of plasma cells, or at least 60%, of plasma cells of plasma cells.

vi. Safety in Cytogenetic Subgroups

The number of TEAE experienced by high and standard risk patients treated with either IPd or Pd is shown in Table M3.

TABLE M3

| | High risk | | Standard risk | |
| --- | --- | --- | --- | --- |
| | Isa-Pd (n = 23) | Pd (n = 34) | Isa-Pd (n = 103) | Pd (n = 76) |
| Median duration of treatment exposure, weeks (range) | 32.0 (1.3-60.1) | 18.0 (1.0-56.0) | 42.0 (4.0-76.7) | 31.3 (2.0-69.0) |
| Any TEAE | 23 (100) | 32 (94.1) | 102 (99.0) | 75 (98.7) |
| Grade ≥3 TEAE | 22 (95.7) | 23 (67.6) | 88 (85.4) | 58 (76.3) |
| Serious TEAE | 17 (73.9) | 17 (50.0) | 60 (58.3) | 47 (61.8) |
| TEAE leading to definitive discontinuation | 2 (8.7) | 8 (23.5) | 7 (6.8) | 6 (7.9) |
| Grade 5 (fatal) TEAE | 6 (26.1) | 4 (11.8) | 4 (3.9) | 4 (5.3) |
| Treatment-related | — | 1 (2.9) | — | 1 (1.3) |

Despite more Grade ≥3 TEAEs in high risk patients, the addition of Isa to Pd did not increase events leading to discontinuation of treatment. Treatment-related mortality did not increase in either subgroup.

The number of Grade ≥3 events in >5% of patients for the indicated laboratory abnormalities and TEAEs experienced by high and standard risk patients treated with either IPd or Pd is shown in Table M4.

TABLE M4

| | Grade ≥3 events in >5% of patients with Isa-Pd in either subgroup, n (%) | | | |
| --- | --- | --- | --- | --- |
| | High risk | | Standard risk | |
| | Isa-Pd (n = 23) | Pd (n = 34) | Isa-Pd (n = 103) | Pd (n = 76) |
| Laboratory abnormalities | | | | |
| Neutropenia | 19 (82.6) | 25 (75.8)* | 88 (85.4) | 53 (69.7) |
| Thrombocytopenia | 11 (47.8) | 9 (27.3)* | 27 (26.2) | 19 (25.0) |

TABLE M4-continued

|  | Grade ≥3 events in >5% of patients with Isa-Pd in either subgroup, n (%) | | | |
|---|---|---|---|---|
|  | High risk | | Standard risk | |
|  | Isa-Pd (n = 23) | Pd (n = 34) | Isa-Pd (n = 103) | Pd (n = 76) |
| TEAEs | | | | |
| Febrile neutropenia | 3 (13.0) | 0 | 12 (11.7) | 2 (2.6) |
| Pneumonia | 5 (21.7) | 6 (17.6) | 16 (15.5) | 14 (18.4) |
| Influenzal pneumonia | 2 (8.7) | 0 | 0 | 2 (2.6) |
| Urinary tract infection | 2 (8.7) | 1 (2.9) | 4 (3.9) | 1 (1.3) |
| Lower respiratory tract infection | 2 (8.7) | 0 | 3 (2.9) | 4 (5.3) |
| Asthenia | 2 (8.7) | 1 (2.9) | 2 (1.9) | 3 (3.9) |
| Fatigue | 2 (8.7) | 0 | 3 (2.9) | 0 |
| Infusion reaction | 2 (8.7) | 0 | 1 (1.0) | 0 |
| Pulmonary embolism | 2 (8.7) | 0 | 1 (1.0) | 3 (3.9) |
| Vomiting | 2 (8.7) | 0 | 0 | 0 |

*n-33; d, dexamethasone, Isa, isatuximab, P, pomalidomide; TEAE, treatment-emergent adverse event.

Isatuximab+pomalidomide+dexamethasone had a manageable safety profile in patients with at least one high-risk cytogenetic abnormality at baseline. The ORR benefit with Isa-Pd vs Pd was maintained among patients with high-risk cytogenetics and benefit was independent of the cytogenetic cut-off definition used. A similar PFS benefit with Isa-Pd vs Pd was observed for high (del[17p], t[4;14] and/or t[14;16]) and standard-risk patients. Isa-Pd provides a consistent benefit vs Pd in the difficult-to-treat subgroup of patients with high-risk cytogenetics and may be a new treatment option for RRMM.

vii. Overall Survival (OS)

As defined in the protocol, efficacy boundaries for OS were to be derived based on the O'Brien and Fleming a spending function according to the actual number of deaths observed at the time of the interim analysis of OS. At the time of the interim analysis of OS, a trend toward longer OS was observed with the addition of isatuximab to Pd treatment, with a clear separation of survival curves from beginning. Median OS was not yet reached in either treatment arm. At time of analysis, the probability of surviving 12 months was 0.633 (95% CI: 0.545 to 0.709) in the Pd arm and 0.720 (95% CI: 0.636 to 0.787) in the IPd arm. Addition of isatuximab to Pd leads to a statistically significant (one-sided p=0.001) and clinically meaningful improvement in the primary endpoint of PFS (as per IRC). See FIG. 4.

viii. Time to Subsequent Therapy

At the time of this analysis, 54% of patients on Pd arm and 39% of patients on IPd arm had started subsequent therapy. The median time to subsequent therapy was 9.1 months on Pd arm and was not reached on IPd arm (HR: 0.538; 95% CI: 0.382 to 0.758).

ix. Other Endpoints

Responses to treatment occurred faster and were more durable in the IPd arm as compared to the Pd arm.

Duration of Response (DOR):

Median duration of response was longer in IPd than in Pd arm (13.27 months [10.612 to NC (i.e., not calculated)] versus 11.07 months [8.542 to NC], respectively). See Table N below.

Time to First Response:

In the patients who achieved a response, the median time to first response was shorter in IPd arm (1.1 months/35 days) than Pd arm (1.9 months/58 days). In ITT analysis, the median time to first response was slightly shorter in the IPd arm than in Pd arm (1.94 months [1.314 to 2.004] versus 3.02 months [2.825 to 5.060], respectively). See Table N.

TABLE N

| | Response Summary | |
|---|---|---|
| Median time | Pom/dex (n = 54) | Isa + Pom/dex (n = 93) |
| Time to first response | 58 days | 35 days |
| Time to best response | 85 days | 76 days |
| Duration of response | 11.07 mos | 13.27 mos |

HR for duration of response is 0.828 (95% CI: 0.464-1.474).

Response rate improvements were observed in all subgroups. In patients who had received 2 or 3 prior lines of therapy for multiple myeloma, response rate was 56.9% in the IPd arm vs. 38.6% in the Pd arm. In patients who had received >3 prior lines of therapy for multiple myeloma, the response rate was 67.3% in the IPd arm vs. 28.8% in the Pd arm.

Interference Assay Evaluation:

Under the category of VGPR, the IRC identified patients in whom criteria for CR were met except for residual immunofixation positivity (historic near-CR category, M-protein undetectable and immunofixation positive). Twenty-four patients in IPd arm (15.6%) and 5 patients (3.3%) in Pd arm had near-CR as their best response. Serum samples from 22 of these patients in IPd arm were tested by mass spectrometry after separation of isatuximab signal from the myeloma M-protein signal. In 11 out of 22 patients (50%), there was no residual myeloma M-protein detectable any more at the sensitivity level of the immunofixation test as performed in the central laboratory for this study (25 mg/dL, Hydragel, Sebia) meaning that the immunofixation was due to the presence of isatuximab. The depth of response, particularly complete response, may be underestimated due to the potential interference of isatuximab with the assessment of M protein by immunofixation.

Minimal Residual Disease (MRD):

Minimal residual disease (MRD) was assessed by the Adaptive clonoSEQ® Assay (version 2.0; Adaptive Biotechnologies, Seattle, Wash., USA) using bone marrow aspirate samples collected at screening (ID calibration sample), at the time of confirmation of complete response or stringent complete response, and three months later in case of MRD positivity. One additional sample could be collected if the patient remained MRD positive. No more than 3 post treatment samples were obtained.

The clonoSEQ Assay is a next-generation sequencing (NGS) based assay that identifies rearranged IgH (VDJ), IgH (DJ), IgK, and IgL receptor gene sequences, as well as translocated BCL1/IgH (J) and BCL2/IgH (J) sequences. The assay also includes primers that amplify specific genomic regions present as diploid copies in normal genomic DNA (gDNA) to allow determination of total nucleated cell content.

Testing began with genomic DNA (gDNA) extracted from bone marrow aspirate. Extracted gDNA quality was assessed and rearranged immune receptors amplified using a multiplex PCR. Reaction-specific index barcode sequences for sample identification were added to the amplified receptor sequences by PCR. Sequencing libraries were prepared from barcoded amplified DNA, which were then sequenced by synthesis using NGS. Raw sequence data were uploaded from the sequencing instrument to the Adaptive analysis pipeline. These sequence data were analyzed in a multi-step process: first, a sample's sequence data were identified using the sample index sequences. Next, data were processed using a proprietary algorithm with in-line controls to remove amplification bias.

When the clonoSEQ Clonality (ID) assessment was conducted, the immune repertoire of the sample was checked for the presence of DNA sequences specific to "dominant" clone(s) consistent with the presence of a lymphoid malignancy. Clonal sequences were assessed for their suitability as ID sequences (to be used for subsequent tracking) by first aggregating highly similar sequences and requiring that the frequency of the sequence was at least 3% as a percentage of all sequences in the locus. The clone had to have a frequency of at least 0.2% of all nucleated cells in the sample with sufficient abundance and differentiation from a polyclonal background. Each sequence being considered for MRD tracking was compared against a B cell repertoire database and assigned a uniqueness value that, together with its abundance relative to other sequences, is used to assign the sequence to a sensitivity bin which was used in the estimation of the reported limit of detection and limit of quantitation on the patient report.

During clonoSEQ Tracking (MRD) assessment, the complete immunoglobulin receptor repertoire was again assessed, and the previously identified dominant clonotype sequence(s) were detected and quantified to determine the sample MRD level.

MRD-negativity rate was defined as the proportion of patients with negative MRD by bone marrow aspirate at any time point after first dose. For analysis purposes, patients in the intent to-treat population without MRD assessment were considered as positive for MRD.

Bone marrow samples for MRD assessment were collected by the investigator for patients with investigator-assessed complete response or if clinically indicated. The analysis was performed on 16 patients including all the patients with confirmed CR or sCR according to IRC review (7 patients in isatuximab arm and 3 patients in control arm). It should be noted that a response different from CR may have been attributed by the IRC as the investigators based their assessments on local M-protein laboratory results while the IRC assessments were based on central M-protein results.

MRD negativity in the ITT population was observed in the IPd arm in 10 (6.5%) patients at a sensitivity of $10^{-4}$ (i.e., 1 multiple myeloma cell in $10^4$ nucleated cells); in 8 (5.2%) patients at a sensitivity of $10^{-5}$ (i.e., 1 multiple myeloma cell in $10^5$ nucleated cells); and in 2 (1.3%) patients at a sensitivity of $10^{-6}$ (i.e., 1 multiple myeloma cell in $10^6$ nucleated cells). No MRD negativity was observed among patients in the Pd (control) arm.

Quality of Life:

Overall quality of life (as measured by Global Health Status Score of QLQ-C30) sustained over time and was similar on both treatment groups. The addition of isatuximab to Pom+Dex did not negatively impact the quality of life of patients. Further analyses indicated that the addition of addition of isatuximab to Pom+Dex preserved health-related quality of life among patients.

Efficacy Analysis According to Prior Lines of Treatment and Refractory Status:

The PFS benefit of IPd compared with Pd was maintained across all subgroups analyzed, regardless of number of prior lines of therapy or refractory status (see Table O below). This included patients with 4 prior lines of therapy (8.54 vs 3.29 months; HR 0.498; 95% CI 0.258-0.962), patients refractory to Len and PI (11.20 vs 4.76 months; HR 0.579; 95% CI 0.401-0.835), and those refractory to Len at last line (11.6 vs 5.7 months; HR 0.50; 95% CI 0.34-0.76). In later analyses, the number of patients in the IPd arm who were refractory to lenalidomide at the last line of therapy was determined to be 93, and the number of patients in the Pd arm who were refractory to lenalidomide at the last line of therapy was determined to be 88.

TABLE O

Progression Free Survival in the IPd and Pd Arms by Refractory Status and Number of Prior Lines of Therapy

| Prior treatment | Median PFS, months | | | | Hazard ratio |
| --- | --- | --- | --- | --- | --- |
| | n | Isa-Pd | n | Pd | (95% CI) |
| Number of prior lines | | | | | |
| 2-3 | 102 | 12.26 | 101 | 7.82 | 0.590 (0.397-0.878) |
| >3 | 52 | 9.40 | 52 | 4.27 | 0.590 (0.356-0.977) |
| 4 | 32 | 8.54 | 28 | 3.29 | 0.498 (0.258-0.962) |
| Refractory status | | | | | |
| Len-refractory | 144 | 11.40 | 140 | 5.59 | 0.593 (0.431-0.816) |
| Refractory to Len at last line | 93 | 11.6 | 88 | 5.7 | 0.50 (0.34-0.76) |
| PI-refractory | 118 | 11.40 | 115 | 5.59 | 0.578 (0.405-0.824) |
| Refractory to Len and PI | 111 | 11.20 | 107 | 4.76 | 0.579 (0.401-0.835) |

Further, more patients responded to treatment with IPd versus Pd, irrespective of number of prior lines of therapy. The overall response rate (ORR) was higher in the IPd arm than in the Pd arm in patients who had received 2-3, >3, and 4 prior therapies. In patients who had received 2-3 prior lines of therapy, the ORR was 56.9% (with 32.4% achieving VGPR or better) in the IPd arm (n=102), as compared to 38.6% (with 10.9% achieving VGPR or better) in the Pd arm (n=101). In patients who had received >3 prior lines of therapy, the ORR was 67.3% (with 30.8% achieving VGPR or better) in the IPd arm (n=52), as compared to 28.8% (with 3.8% achieving VGPR or better) in the Pd arm (n=52). In patients who had received 4 prior lines of therapy, the ORR was 56.3% (with 31.3% achieving VGPR or better) in the IPd arm (n=32), as compared to 28.6% (with 7.1% achieving VGPR or better) in the Pd arm (n=28).

The ORR was higher in the IPd arm vs. the Pd arm in patients who were refractory to lenalidomide (Len), refractory to a proteasome inhibitor (PI), refractory to both Len and PI, and refractory to Len at the last line of treatment. Among Len-refractory patients, the ORR was 59.0% (with 30.6% achieving VGPR or better) in the IPd arm (n=144), whereas the ORR was 31.4% (with 7.1% achieving VGPR or better) in the Pd arm (n=140). Among PI-refractory patients, the ORR was 60.2% (with 30.5% achieving VGPR or better) in the IPd arm (n=118), whereas the ORR was 32.2% (with 7.8% achieving VGPR or better) in the Pd arm (n=115). Among patients who were refractory to both Len and a PI, the ORR was 58.6% (with 29.7% achieving VGPR or better) in the IPd arm (n=111), whereas the ORR was 29.9 (with 8.4% achieving VGPR or better) in the Pd arm (n=107). Among patients who were refractory to Len at the last line of treatment, the ORR was 55.9% (with 32.3% achieving VGPR or better) in the IPD arm (n=93), whereas the ORR was 29.5% (with 4.5% achieving VGPR or better) in the IPd arm (n=88).

The PFS benefit of IPd vs. Pd was consistent with that of the overall population, regardless of number of prior lines of therapy or refractory status. The addition of isatuximab to pomalidomide+dexamethasone improved treatment response rates in all subpopulations analyzed by prior treatment. Notably, the benefit of IPd versus Pd was maintained in patients refractory to Len at last line of treatment.

D. Safety

Safety was assessed through incidence of treatment emergent adverse events (TEAEs), serious adverse events (SAEs), TEAEs leading to treatment discontinuation, other significant AEs (e.g., infusion reactions, second primary malignancies, respiratory AEs, neutropenia and neutropenic complications, infections, thrombocytopenia and hemorrhages, tumor lysis syndrome, hemolytic disorders and blood cell transfusions, autoimmune disorders), standard hematology and blood chemistry. The safety population included patients from the ITT population who actually received at least one dose or part of a dose of the study treatments. All analyses using this population were based on the treatment actually received. The overall safety profile of IPd was well characterized and manageable, and does not interfere with the duration of treatment and the persistent clinical benefit. The addition of isatuximab to Pd was mostly associated with low grade infusion reactions and an increase in neutropenia and infections. No positive ADA (i.e., anti-drug antibodies, specifically anti-isatuximab antibodies, were identified.

Addition of isatuximab to pomalidomide and dexamethasone demonstrated a statistically significant and clinically meaningful benefit in PFS in heavily treated patients with relapsed and refractory multiple myeloma The Kaplan-Meier curves (FIGS. 2 and 3) showed an early and sustained separation that translated into a 41% decrease in risk of death or progression for patients in the isatuximab arm. The PFS benefit was seen in all subgroups, including patients with high risk cytogenetics (HR 0.66), patients older than 75 years, those with renal function impairment, and those who received 2-3 prior line, those who received >3 prior lines, were refractory to lenalidomide and a proteasome inhibitor, and were refractory to lenalidomide in the last line. PFS with isatuximab, pomalidomide, and dexamethasone is the longest observed to date in this patient population. High risk cytogenetics was determined by central laboratory FISH analyses using internationally accepted thresholds for positivity. In addition the overall response benefit was seen in all subgroups. The results of the subgroup analysis also provide the first evidence of improvement in renal function with a CD38-targeted therapy in patients with RRMM.

IPd (i.e., isatuximab with pomalidomide and dexamethasone) significantly improved response rate, and depth of response compared with Pd (i.e., pomalidomide and dexamethasone). IPd treatment also led to reversal of renal impairment. Minimal residual disease negative status at $10^{-5}$ level was obtained in 5.2% of patients in the isatuximab arm and 0% in the control arm (ITT).

Example 2: A Subgroup Analysis of East Asian Patients in the Phase III Randomized, Open-Label, Multicenter Study Comparing Isatuximab (SAR650984) in Combination with Pomalidomide and Low-Dose Dexamethasone Vs. Pomalidomide and Low-Dose Dexamethasone in Patients with Refractory or Relapsed and Refractory Multiple Myeloma This Example describes a subgroup analysis of East Asian patients in the phase III, multicenter, multinational, randomized, open-label, parallel group, 2-arm study described in Example 1. This subgroup analysis evaluated the safety and efficacy of isatuximab in combination with pomalidomide and low-dose dexamethasone compared with pomalidomide and low-dose dexamethasone for the treatment of East Asian patients with refractory or relapsed and refractory multiple myeloma (RRMM) who had received at least 2 prior lines therapy (e.g., ≥2 lines prior lines of therapy) for multiple myeloma, including lenalidomide and a proteasome inhibitor (e.g., bortezomib, carfilzomib or ixazomib), given alone or in combination, and who were refractory to their last therapy.

As described in detail in Example 1, East Asian patients were randomized into either the Isa-Pd (IPd) experimental arm or the Pd control arm. Patients in the IPd arm received isatuximab at a dose of 10 mg/kg on Days 1, 8, 15, and 22 for Cycle 1, and then at a dose of 10 mg/kg on Days 1 and 15 for subsequent 28-day cycles. Patients in the IPd and Pd arms received pomalidomide at a dose of 4 mg on each of Days 1 to 21 for each 28-day cycle, and dexamethasone at a dose of 40 mg (or 20 mg if the patient was ≥75 years old), per os or intravenously on Days 1, 8, 15 and 22.

Results

A. Patient Characteristics

Thirty-six East Asian patients (13 patients Japanese, 9 Korean, and 14 Taiwanese patients) were included in this subgroup analysis. Twenty-one patients in the East Asian subgroup had been assigned to the IPd experimental treatment arm, and fifteen patients had been assigned to the Pd control treatment arm. Of the 13 Japanese patients in this subgroup, nine patients had been assigned to the IPd experimental treatment arm, and four patients had been assigned to the Pd control treatment arm.

Patients' characteristics in the East Asian subgroup were similar to the entire population of the Phase III study described in Example 1. The median age was 65 (range: 41-85). The median number of prior lines of therapy was 3 (range: 2-7). 91.7% of the patients in this subgroup were refractory to prior lenalidomide treatment, and 69.4% of the patients in this subgroup were refractory to prior PI treatment. 13.9% of East Asian patients had high-risk cytogenetics.

B. Efficacy i. Progression Free Survival (PFS)

After median follow-up of 11.6 months, the median PFS was not reached for the IPd arm. For the Pd arm, the median PFS was 7.9 months (HR 0.517 [95% CI 0.19-1.39]).

ii. Overall Response Rate (ORR)

The ORR (≥PR) was 71.4% in the IPd arm and 60% in the Pd arm.

The VGPR rate or better was 61.9% in the IPd arm, and 13.3% in the Pd arm.

The median time to first response was 32 days in the IPd arm, and 59 days in the Pd arm.

C. Safety

Grade ≥3 AEs were observed in 90.5% and 93.3% of patients in the IPd and Pd arms, respectively. Grade ≥3 AEs led to 9.5% of patients in the IPd arm to discontinue their treatment.

Infusion reactions were reported in 57.1% of patients receiving IPd. No infusion reactions were grade 3-4.

Conclusions

The subgroup analysis of 36 East Asian patients from the Phase III study described in Example 1 demonstrates that the efficacy and safety of Isa-Pd in the East Asian population, including Japanese patients, were comparable with the entire population of the study in Example 1. Isa-Pd is a novel treatment option for East Asian patients with RRMM.

Example 3: Depth of Response and Response Kinetics in the Study of Ilsatuximab+Pomalidomide+Dexamethasone in Relapsed/Refractory Multiple Myeloma Patients In multiple myeloma (MM), deep responses have been associated with improvements in progression-free survival (PFS) and overall survival (OS). Response kinetic data, including renal response times, which are highly important for patients with renal impairment (RI), are infrequently reported. The association between depth of response, including minimum residual disease (MRD) negativity, plus response kinetics and long-term outcomes, were analyzed using data from the randomized, open-label, active-controlled, phase 3 study described in Example 1.

Methods

As described in Example 1, all patients received standard doses of pomalidomide+dexamethasone ("Pd") and those randomized to the Isa-Pd group received Pd in addition to 10 mg/kg isatuximab IV on days 1, 8, 15, and 22 (cycle 1), and days 1 and 15 in subsequent 28-day cycles until progression. Depth and kinetics of response were analyzed for each treatment group. Minimal residual disease ("MRD") was assessed at $10^{-5}$ (tested by next-generation sequencing in patients with complete response [CR]/stringent CR [sCR]). Time to biochemical response, time to renal response (CRenal; improvement in estimated glomerular filtration rate (eGFR), using the MDRD GFR formula (see www(dot)kidney(dot)org/content/mdrd-study-equation), from <50 mL/min/1.73 m² at baseline to ≥60 mL/min/1.73 m² at ≥1 post-baseline assessment), and time to sustained CRenal (a CRenal lasting ≥60 days) were recorded. No neutralization assay was used for patients with IgG kappa clonality.

Results

Overall, 307 patients were randomized to Isa-Pd (n=154) or Pd (n=153) of whom 33/142 (23.2%) and 24/145 (16.6%) patients had eGFR<50 mL/min/1.73 m² measured at baseline. Patients had received a median of 3 prior lines of therapy (range 2-11) and 73.4% and 71.9% of patients in the Isa-Pd and Pd groups, respectively were double refractory (i.e., refractory to an IMiD® and a proteasome inhibitor). Median PFS was 11.53 months with Isa-Pd and 6.47 months with Pd (hazard ratio [HR] 0.596 [95% confidence interval (CI) 0.436-0.814]). Biochemical responses on Isa-Pd were more frequent and deeper than on Pd. Overall response rates (ORR) were 60.4% vs 35.3% (odds ratio [OR] 2.80; 95% confidence interval [CI] 1.72-4.56; p<0.0001); ≥ very good partial response rates (VGPR) were 31.8% vs 8.5% (OR 5.03; 95% CI 2.51-10.59; p<0.0001). As no isatuximab interference assay was performed, near complete response rates (immunofixation remained positive) were reported: 15.6% in the Isa-Pd group vs. 3.3% in the Pd group (OR 5.47; 95% CI 1.96-18.78; p=0.0002). MRD negativity rates (at a sensitivity of $10^{-5}$) in the ITT population were 5.2% in the Isa-Pd group vs 0% in the Pd group. Depth of response correlated with improved long-term outcomes in both arms. After a median follow-up of 11.6 months in the Isa-Pd arm, 100% of MRD negative (MRDneg) patients were progression-free and alive. In the Isa-Pd arm, median PFS was longer with increased depth of response. Among MRDneg patients in the Isa-Pd arm (n=8), median PFS was not reached (NR). Among ≥VGPR patients in the Isa-PD arm who were MRD+(n=42), the median PFS was 15.21 months. Among patients in the Isa-Pd arm who achieved PR (n=44), the median PFS was 11.53 months. Among patients in the Isa-Pd arm who achieved less than PR (n=57), the median PFS was 3.29 months (see FIG. 6A). In the Pd arm, median PFS was not calculable in patients achieving a response of ≥PR, whereas median PFS was 2.86 months (range: 2.6-3.81 months) in patients with <PR.

In the Isa-Pd arm, 1-year OS rate was highest in MRD- patients and correlated with depth of response. Among MRDneg patients in the Isa-Pd arm, the one-year OS rate was 100%. Among ≥VGPR patients in the Isa-Pd arm who were MRD+, the one-year OS rate was 92.9%. Among patients in the Isa-Pd arm who achieved PR, the one-year OS rate was 82.4%. Among patients in the Isa-Pd arm who achieved less than PR, the one-year OS rate was 46.4% (see FIG. 6B). The one-year OS rate also correlated with depth of response in the Pd arm. Among ≥VGPR patients in the Pd arm who were MRD+, the one-year OS rate was 88.9%. Among patients in the Pd arm who achieved PR, the one-year OS rate was 90.6%. Among patients in the Pd arm who achieved less than PR, the one-year OS rate was 54.3%

Biochemical responses occurred faster with Isa-Pd than with Pd. Among patients who achieved a response of ≥PR (93 in the Isa-Pd arm and 54 in the Pd arm), the median time to first response was shorter for Isa-Pd (1.1 months) than for Pd (1.9 months). Among patients who achieved a response of ≥VGPR (49 and 13 in the Isa-Pd and Pd arms, respectively), the time to first VGPR or better response was similar, i.e., 2.9 months for Isa-Pd and 3.0 months for Pd. Among patients who achieved a response of ≥CR (7 patients in the Isa-Pd arm and 3 in the Pd arm) the median time to first CR response or better was shorter for Isa-Pd (5.7 months) than for Pd (7.9 months). The time to best response was 2.5 months in the Isa-Pd group, as compared to 2.8 months in the Pd group.

Renal responses occurred faster in patients on Isa-Pd than on Pd. A complete renal response (CRenal) was observed in 23/32 (71.9%) patients in the Isa-Pd arm (median time to first complete renal response was 4.1 weeks) and in 8/21 (38.1%) of patients in the Pd arm (median time to first response 7.3 weeks). A sustained CRenal (i.e., CRenal ≥60 days, also known as "durable CRenal") was observed in 10/32 (31.3%) patients in the Isa-Pd arm (median time to first response 2.4 weeks) and in 4/21 (19.0%) patients in the Pd arm (median time to first response 4.8 weeks). Additionally, renal responses occurred faster in patients in the Isa-Pd arm than in the Pd arm. See FIG. 7. As noted above, the median time to CRenal was 4.1 weeks in the Isa-Pd arm vs. 7.3 weeks in the Pd arm. The median time to sustained CRenal (i.e., CRenal ≥60 days) was 2.4 weeks in the Isa-Pd arm, vs. 4.8 weeks in the Pd arm. The median time to first renal response (including minor response and partial response) was 3.1 weeks in the IPd arm vs. 7.3 weeks in the IPd arm.

Conclusions

In the heavily pretreated population studied in Example 1, Isa-Pd induced more frequent and faster biochemical responses (i.e., tumor responses) and renal responses than Pd. Depth of response, including MRD negativity, was improved with Isa-Pd and was associated with better long-term survival outcomes (i.e., PFS and OS). The results of the subgroup analysis also provide the first evidence of improvement in renal function with a CD38-targeted therapy in patients with RRMM.

Example 4: Efficacy of Isatuximab with Pomalidomide and Dexamethasone in Elderly Patients with Relapsed/Refractory Multiple Myeloma Multiple myeloma (MM) is most frequently diagnosed among people aged 65-74 and approximately one third of patients are aged ≥75 years. Advanced age has a negative effect on the prognosis of patients with MM. Example 1 compared treatment with the anti-CD38 monoclonal antibody isatuximab (Isa) in combination with pomalidomide and dexamethasone (Pd) with Pd. Patients had relapsed/refractory MM (RRMM) after ≥2 prior lines of therapy, including lenalidomide and a proteasome inhibitor. This subgroup analysis of examined efficacy and safety in elderly patients (≥75 years) compared with younger patients.

Methods

Patients were randomized (1:1) to receive Isa-Pd or Pd. Isa (10 mg/kg IV) was given on days 1, 8, 15, and 22 (cycle 1), and days 1 and 15 in subsequent 28-day cycles. All patients received pomalidomide 4 mg on days 1 to 21 of each cycle and dexamethasone 40 mg (20 mg for patients ≥75 years old) on days 1, 8, 15, and 22 of each cycle. The primary endpoint was progression free survival (PFS), assessed by an independent response committee. Subgroup analyses were conducted for patients aged <65, 65-74 and ≥75 years of age.

Results

Overall, 307 patients were randomized to Isa-Pd (n=154) or Pd (n=153) and included in the intent to treat population. The median age of patients was 68.0 years in the Isa-Pd arm and 66.0 years in the Pd arm. In the Isa-Pd and Pd arms, there were 54 (35%) and 70 (46%) patients <65 years of age, 68 (44%) and 54 (35%) patients 65-74 years of age, and 32 (21%) and 29 (19%) patients ≥75 years of age, respectively.

In the overall population, median PFS was significantly improved with Isa-Pd versus Pd (11.53 vs 6.47 months; hazard ratio [HR] 0.596 [95% confidence interval (CI) 0.436-0.814], p=0.001)). Consistent with this, patients ≥75 years of age had a median PFS of 11.40 with Isa-Pd vs 4.47 months with Pd (HR 0.479 [95% CI, 0.242-0.946]). Similarly, in the Isa-Pd and Pd groups, patients 65-74 years of age had a PFS of 11.57 and 8.58 months (HR 0.638 [0.385-1.059]), and for patients <65 years of age, PFS was 11.53 months vs 5.03 months, respectively (HR 0.656 [95% CI, 0.401-1.074]). See Table P.

TABLE P

Median PFS in Patients Aged <65 Years vs. 65-74 Years vs. ≥75 Years in Both Treatment Arms.

|  | <65 Years Old | 65-74 Years Old | ≥75 Years Old |
| --- | --- | --- | --- |
| Isa-Pd Arm | 11.53 months | 11.57 months | 11.40 months |
| Pd Arm | 5.03 months | 8.58 months | 4.47 months |

Overall response rate (ORR) for all patients was 60.4% with Isa-Pd and 35.3% with Pd with an odds ratio (OR) of 2.80 (95% CI, 1.72-4.56). ORR by age group in patients receiving Isa-Pd vs Pd was: 53.1% and 31.0% in the ≥75 years group (OR 2.52 [95% CI, 0.79-8.26]); 64.7% and 38.9% in the 65-74 years group (OR 2.88 [95% CI, 1.29-6.46]); and 59.3% and 34.3% in the <65 years group (OR 2.79 [95% CI, 1.26-6.20]).

At least a very good partial response (VGPR) was achieved by 31.8% of patients with Isa-Pd and 8.5% with Pd with an OR of 5.03 (95% CI, 2.51-10.59). Rates of ≥VGPR by age in patients receiving Isa-Pd vs Pd was: 31.3% and 0% in the ≥75 years group (OR not calculated); 32.4% vs 13.0% in the 65-74 group (OR 3.21 [95% CI, 1.17-9.70]); and 31.5% and 8.6% in the <65 years group (OR 4.90 [95% CI, 1.64-16.35]).

Overall, 8 patients in the Isa-Pd arm had minimal residual disease negativity at $10^{-5}$. 2/8 were ≥75 years old, and 2/8 were aged 65-74 years. The remaining 4 patients were less than 65 years of age. No patients in the Pd arm achieved MRD negativity.

At the time of interim analysis, overall survival (OS) data are not yet mature. However, in the elderly population, 8/32 (25%) patients in the Isa-Pd arm had died with median OS not reached, and in the Pd arm, 15/29 (51.7%) had died with a median OS of 10.25 months (HR 0.404 (95% CI 0.171-0.956).

In a subsequent analysis of OS in patients aged 65-74, median OS was not reached in the Isa-Pd arm, and median OS in the Pd arm was 14.5 months (HR 0.75;95% CI 0.38-1.45). For patients aged <65 years, median OS was not reached for either treatment arm (HR for Isa-Pd vs. Pd was 0.85 (95% CI 0.46-1.59).

One-year OS rates for patients aged ≥75, patients aged 65-74, and patients aged <65 years were similar in the Isa-Pd group. See Table Q below.

TABLE Q

One-year Overall Survival Rates in Patients Aged <65 Years vs. 65-74 Years vs. ≥75 Years in Both Treatment Arms.

|  | <65 Years Old | 65-74 Years Old | ≥75 Years Old |
| --- | --- | --- | --- |
| Isa-Pd Arm | 67.7% | 74.7% | 73.5% |
| Pd Arm | 63% | 72.9% | 47.2% |

In the Isa-Pd arm, the incidence of all grade treatment-emergent adverse events (TEAEs) was similar across age groups: <65 years, 98.1%; 65-74 years, 100%; and ≥75 years, 100%. The incidence of TEAEs was comparable in both arms.

There were more Grade ≥3 TEAEs with Isa-Pd in patients aged ≥75 years (93.8%) compared with patients <65 years of age (85.2%), with a similar trend observed in the Pd arm (75.0% and 64.7%, respectively). There were also more treatment discontinuations because of TEAEs in patients ≥75 years of age versus <65 years in the Isa-Pd arm (15.6% and 7.4%) and in the Pd arm (14.3% and 10.3%). There was a higher incidence of serious TEAEs (SAEs) in patients aged ≥75 years compared with patients <65 years in both arms (Isa-Pd, 68.8% and 57.4%; Pd, 57.1% and 47.1%, respectively). The incidence of TEAEs with fatal outcome was lower in patients aged ≥75 years in the Isa-Pd arm (6.3%) compared with patients <65 years (11.1%), while the opposite trend was observed with Pd (14.3% vs 5.9%).

Conclusions

The addition of Isa to Pd improved rates of PFS, ORR, ≥VGPR, and OS, in elderly patients, consistent with the benefit observed in the overall study population. In the Isa-Pd arm, PFS and one-year OS rates were similar in patients aged <65 years, 65-74 years, and ≥75 years. There was a consistent trend towards higher rates of SAE and discontinuation due to TEAE in patients aged ≥75 years in both the Isa-Pd and Pd arms compared to younger patients, but with no increase in fatal AEs in the Isa-Pd arm.

Example 5: Relationship Between Baseline Biomarkers in RRMM and Efficacy of Isatuximab in Combination with Pomalidomide and Dexamethasone Baseline biomarker analyses were performed on samples from 2 clinical studies (i.e., a phase I study to evaluate the safety and maximum tolerated dose of isatuximab in combination with pomalidomide and dexamethasone in patients with relapsed/refractory multiple myeloma, and the phase III study described in Example 1). CD38 receptor density (RD), FCGR3A (Fc immunoglobulin receptor) genotype, and bone marrow or peripheral blood immunophenotyping were evaluated for being informative for a response to the Isa-Pd regimen.

Methods

Both studies enrolled similar populations of patients with RRMM who had received ≥2 prior lines of therapy including lenalidomide and a proteasome inhibitor. Baseline blood samples were taken prior to first treatment administration in both studies; in addition, a bone marrow sample was taken during screening in the phase I study. In the phase I study, bone marrow plasma cells were analyzed for CD38 RD. Immune cell populations (CD19$^+$ B-cell, CD3$^+$ T-cell, CD4$^+$ T-cell, regulatory T-cells (Tregs) and natural killer (NK) cells [CD56$^+$ bright CD16$^+$ low subset and CD56$^+$ dim CD16$^+$ bright subset]) were characterized using blood samples and bone marrow aspirates. Blood samples from both studies were analyzed for FCGR3A genotyping (V158 and F158 high- and low-affinity alleles). Biomarker results were correlated with response, defined as at least partial response according to International Myeloma Working Group criteria.

Results

The phase I study enrolled and treated 45 patients with Isa-Pd. As discussed in Example 1, the phase III study randomized 154 patients to Isa-Pd and 153 patients to Pd. Baseline patient demographics were similar for both studies and the median number of prior lines of therapy was 3 (range: 1-10) for the phase I study, and 3 (2-11) for the phase III study. The overall response rates (ORR) with Isa-Pd were 62.2% (28/45) in the phase I study and 60.4% (93/154) in the phase III study. In the phase I study, the median CD38 RD, for 31 treated patients with evaluable results, was 108172 receptors/cancer cell (range: 12950-337335). In patients responding to Isa-Pd (n=21), the median CD38 RD value was 120931 (48770-337335) receptors/cancer cell; in patients not responding to Isa-Pd (n=10), the median CD38 RD value was 85370 (range 12950-309003) receptors/cancer cell. Across five Phase I/II clinical studies with Isa, 4/198 patients (2.0%) had a CD38 RD level below 48770, the lowest value in a responder patient.

FCGR3A genotyping results were available for both studies. Across both studies, the distribution of the F158V single nucleotide polymorphism of FCGR3A gene was 42% for F/F, 42% for F/V and 16% for V/V as found in the general population. In both studies, responses were observed for all 3 genotypes (Table R). In the phase I study, the observed ORRs with the Isa-Pd regimen for the 3 genotypes ranged from 50.0% to 80.0%, whereas in the larger phase III study, the ORR with the Isa-Pd regimen was more similar across genotypes (range 56.9% to 65.5%). Progression-free survival (PFS) ranged from 8.97 months to 14.78 months and Isa-Pd showed a PFS benefit vs Pd for all 3 genotypes (see Table R).

TABLE R

Response data by FCGR3A genotypes

| | Study 2 | | Study 1 |
|---|---|---|---|
| | Isa-Pd | Pd | Isa-Pd |
| ORR, n/N (%) | 93/154 (60.4) | 54/153 (35.3) | 28/45 (62.2) |
| F158F | 36/55 (65.5) | 19/50 (38.0) | 11/22 (50.0) |
| F158V | 33/58 (56.9) | 25/66 (37.9) | 12/17 (70.6) |
| V158V | 16/25 (64.0) | 8/23 (34.8) | 4/5 (80.0) |
| Median PFS, months | 11.53 | 6.47 | 17.6 |
| | HR, 0.596 (95% CI 0.436-0.814) | | |
| F158F | 11.53 | 7.03 | NA |
| | HR, 0.561 (95% CI 0.329-0.957) | | |
| F158V | 8.97 | 7.43 | NA |
| | HR, 0.728 (95% CI 0.450-1.178) | | |
| V158V | 14.78 | 4.47 | NA |
| | HR, 0.447 (95% CI 0.190-1.048) | | |

In the phase I study, 42 patients had at least one baseline peripheral blood immune biomarker value and of these, 17 patients were non-responders and 25 patients were responders. In addition, 41 patients had at least one baseline bone marrow immune biomarker measurement (16 were non-responders and 25 were responders). No significant difference was observed between responders and non-responders for the tested immune biomarkers in bone marrow during screening. P-values were 0.2817 (CD19+ B-cell), 0.6446 (CD3$^+$ T-cell), 0.7780 (CD4$^+$ T-cell), 0.1620 (Tregs), 0.9591 (NK cell), 0.8275 (CD56$^+$ bright/CD16$^+$ low NK cell), and 0.7389 (CD56$^+$ dim/CD16$^+$ bright NK cell). Similarly, there was no significant difference between responders and non-responders for the immune biomarkers in blood.

Conclusions

Biomarker analyses on samples from patients treated with Isa-Pd showed that the treatment benefit of Isa-Pd was seen in all groups, regardless of baseline bone marrow plasma cell CD38 RD, FCGR3A genotype, or immunophenotypes in bone marrow plasma cells or peripheral blood.

Example 6: Development of Pharmaceutical Formulations Comprising Isatuximab for Intravenous Administration Development of Formulation 1 (Containing 5 mg/ml Isatuximab)

Formulation 1 was developed with isatuximab at a concentration of 5 mg/mL to achieve the desired pH, osmolality, and stability requirements. Several different formulations were developed and tested under various stress conditions designed to mimic those conditions encountered during manufacture, shipping, storage, and handling. The stress conditions under which each formulation was tested included:

mechanical stress by shaking (350 rpm during 15 hours),
thermal stress at 40° C. or 45° C.,
freeze-thaw cycling (3 to 5 cycles from −20° C. or −30° C. to room temperature),
light exposure (suntest), and
dilution with infusion solutions.

Formulations comprising one of the following buffers at one of the follong pH values were also tested:

citrate 10 mM, pH=5.0, 5.5, 6.0, 6.5, or 7.0;
histidine 10 mM, pH=5.5, 6.0, or 6.5;
phosphate 10 mM, pH=6.5, 7.0, or 7.4
succinate 10 mM, pH 5.0, 5.5, or 6.0; and
acetate 10 mM, pH=5.0 or 5.5.

The buffer-pH systems were chosen based on their buffering capacity in the pH range of interest. The buffer-pH systems were evaluated with regard to their impact on aggregation of isatuximab, in terms of formation of visible and sub-visible particles and formation of high-molecular weight species (HMWS, e.g., soluble aggregates) after shaking and thermal stress.

Formulations containing histidine or acetate buffers were found to provide higher stability compared to formulations containing citrate, phosphate, or succinate buffers. Furthermore, citrate and succinate buffers were found to reduce the solubility of isatuximab, as the solution became opalescent with each of these two buffers. Dynamic Light Scattering (DLS) showed increasing Z-average values, and Static Light Scattering (SLS) showed, with virial coefficient A22, molecule attraction in formulations comprising sodium citrate or sodium succinate and molecule repulsion in formulations comprising histidine. Furthermore, histidine buffer produced less HMWS (as measured via size exclusion high-performance liquid chromatography (SE-HPLC)) of isatuximab during UltraFiltration/Diafiltration compared to citrate and succinate buffers.

Formulations comprising histidine and acetate buffers were further tested for their impact on stability against charge heterogeneity under thermal stress and showed similar stability. Based on study results, the following buffer-pH systems for isatuximab stabilization were selected for further development steps: histidine 10 mM, pH=5.5 to pH 6.5; Acetate 10 mM, pH=5.0 and pH 5.5.

NaCl (0.8% w/v), sucrose (5% w/v), and mannitol (3% w/v) were tested for their ability to improve the stability of isatuximab in combination with the selected pH buffering system (as measured by aggregation of isatuximab). Aggregation was assessed after shaking, thermal stress and/or freeze/thaw cycles by measuring the amount of visible and sub-visible particles, soluble aggregates (HMWS), and fragments (low molecular weight species (LMWS)).

A substantial destabilization of isatuximab under thermal, freeze-thaw, and shaking stress (as shown by increased levels of sub-visible particles) was found with formulations comprising NaCl.

Formulations comprising sucrose or mannitol were found to have a stabilizing effect on isatuximab.

Formulations containing acetate buffer showed higher Post-Translational Modifications (PTM) under thermal stress compared to formulations with histidine. Higher deamidation was found in formulations containing acetate buffer.

No major differences in the behavior of isatuximab (e.g., according to the criteria discussed above using the assays discussed above) were observed in formulations containing histidine at pH values between 6.0 and 6.5 and sucrose or mannitol. Therefore histidine pH 6.5 buffer was selected for further development testing. The concentration of mannitol was increased to 5% (w/v) and the concentration of sucrose was increased to 10% (w/v) to target iso-osmolality in Formulation 1. Sucrose 10% (w/v) corresponds to 292 mOsm/kg osmolality, and mannitol 5% (w/v) corresponds to 330 mOsm/kg osmolality.

Next, a variety of surfactants at different concentrations were evaluated. Polysorbate 80 (PS80) was tested at concentrations of 0.001% to 0.01% with histidine 10 mM pH 6.5, 5% mannitol. The test formulations were subjected to shaking stress (15h at 350 rpm) or to dilution to 2 mg/mL in NaCl 0.9% or dextrose 5% solutions. Sub-visible particles under light obscuration (LO) were estimated. Equivalent results were obtained with formulations comprising PS80 at all concentrations tested, even at the lowest level of 0.001% PS80, showing the efficient stabilization of isatuximab by PS80 under the applied stresses. A concentration of 0.005% of PS80 was selected to allow for potential adsorption of PS80 during manufacturing steps (i.e. compounding of the formulated drug substance, filtration and filling operations).

Two formulations, histidine 10 mM, PS80 0.005% (w/v) pH 6.5 containing either 5% (w/v) mannitol or 10% (w/v) sucrose were selected from the formulation development studies and tested six month stability as shown in Table S.

TABLE S

| CONDITIONS | TESTS | | | |
|---|---|---|---|---|
| T° | Purity by SEC-HPLC | HMW | Monomer | LMW |
| 40°, 1 M | Charge heterogeneity by WCX: | Acidic | Main | Basic |
| 25°, 6 M | Sub-visible particulate (LO by HIAC) | ≥10 μm | | ≥25 μm |
| 5°, 6 M Photostability per ICH$^a$ | | | | |

$^a$Suntest exposure: Overall illumination of not less than 1.2 million lux hours and an integrated near ultraviolet energy of not less than 200 watt · hours/m². A dark control sample is stored under the same conditions to eliminate any effect due to local temperature changes.

Based on variability of different analytical procedures, no significant differences were observed between either formulation, except under Suntest exposure, where mannitol-containing prototypes had more acidic forms. Furthermore, mannitol can crystalize at freezing temperatures. Therefore, sucrose was selected as stabilizer.

As a result, pharmaceutical formulation 1 was developed containing the following:

5 mg/mL isatuximab
10 mM Histidine
10% (w/v) Sucrose
0.005% (w/v) Polysorbate 80
pH 6.5.

Isatuximab formulated in Formulation 1 was shown to have a 24 month shelf life at +5° C.±3° C. The 5 mg/ml concentration of isatuximab was compatible with very low doses of isatuximab to satisfy Minimal Anticipated Biological Effect Level (MABEL) dosing schedules; however, to allow administration of higher doses, a formulation containing a higher concentration of isatuximab was also needed. Development of Formulation 2 (Containing 20 mg/ml Isatuximab)

pH and molarity of the histidine buffer were tested for potential stability improvement and higher buffering capacity. Histidine was tested at the following concentrations and pH values: 10 mM, pH=6.0; 10 mM, pH=6.5; 20 mM, pH=6.0; and 20 mM, pH 6.5. The stability of isatuximab in each test formulation was evaluated by measuring aggregation (HMWS and LMWS by SE-HPLC), sub-visible particles count (using Flow Cell Microscopy (FCM)), charge heterogeneity (using weak cation exchange chromatography (WCX)), hydrodynamic radius values (Z average), and polydispersity index (PdI) by DLS) under stress thermal conditions, namely, 1 month at 40° C. Surprisingly, better stabilization of isatuximab was observed in the pH 6.0 formulations (10 mM or 20 mM histidine) compared to the pH 6.5 formulations. Therefore, 20 mM histidine at pH 6.0 was selected for Formulation 2 due to increased stability of isatuximab and higher buffering capacity.

Impact of PS80 Surfactant Content

The impact of PS80 content was assessed in formulations containing between 0.015% (w/v) and 0.025% (w/v) PS80. Shaking and dilution in infusion solution were applied as stress conditions.

No difference in number of subvisible particles was observed by Flow Cell Microscopy for PS80 content ranging between 0.015% (w/v) and 0.025% (w/v) after subjecting the test formulations to shaking.

Formulations having a PS80 content of between 0.015% (w/v) and 0.025% (w/v) were tested for stability after dilution in NaCl 0.9% solution. The formulations were diluted to 2 mg/mL isatuximab in NaCl 0.9% infusion bags. Samples were measured for sub-visible particles. No differences between formulations were observed. Therefore, formulatoins having PS80 concentrations between 0.015% (w/v) and 0.025% (w/v) were found to have similar stability profiles for isatuximab at 20 mg/ml.

Under long term storage, it is possible that PS80 may degrade over time. To mimic the effects of long term storage, formulations having PS80 at a concentration of 0.0057% (w/v) were evaluated by applying stirring, shaking and freeze/thaw stress conditions. Such conditions correspond to storage of samples initially containing 0.020% or 200 ppm of PS80 at 5° C. for 50 months.

No change in aggregation characteristics was observed after exposure to agitation stresses (stirring and shaking), or after freeze/thaw stress. This demonstrates that isatuximab stability is not impacted when formulated at 20 mg/ml isatuximab with 20 mM histidine, 10% (w/v) sucrose at pH 6.0, by a decrease in PS80 content as low as 57 ppm, even after exposure to agitation or freeze-thaw stress.

As a result, pharmaceutical Formulation 2 was developed containing the following:
20 mg/mL isatuximab
20 mM Histidine
10% (w/v) Sucrose
0.02% (w/v) Polysorbate 80
pH 6.0.

Although the present disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

---

The invention claimed is:

1. A method of improving renal impairment in an individual in need thereof,
wherein the individual has multiple myeloma, and
wherein the individual has one or more of: chronic obstructive pulmonary disorder (COPD), asthma, and bronchospasms,
comprising administering to the individual an anti-CD38 antibody, pomalidomide, and dexamethasone,
wherein the anti-CD38 antibody is isatuximab and is administered at a dose of 10 mg/kg, the pomalidomide is administered at a dose of 4 mg, and the dexamethasone is administered at a dose of 40 mg wherein the individual is under 75 years of age, or at a dose of 20 mg wherein the individual is 75 years of age or older, thereby improving renal impairment,
wherein the individual has received at least two prior therapies for multiple myeloma,
wherein at least one of the at least two prior therapies for multiple myeloma was lenalidomide and at least one of the at least two prior therapies was a proteasome inhibitor, and
wherein the individual is more likely to achieve a complete renal response following the treatment, as compared to a treatment comprising the pomalidomide and the dexamethasone without the anti-CD38 antibody.

2. The method according to claim 1, wherein the individual did not respond to at least one of the at least two prior therapies, or wherein the individual relapsed after at least one of the at least two prior therapies, or wherein the individual experienced disease progression during or after the treatment with at least one of the at least two prior therapies.

3. The method according to claim 1, wherein the treatment extends progression free survival (PFS) and/or the overall survival (OS) of the individual.

4. The method according to claim 3, wherein the treatment extends the PFS of the individual by at least about 9 months.

5. The method according to claim 3, wherein the treatment extends the PFS of the individual by at least about 4.5 months relative to an individual having multiple myeloma who received a treatment comprising pomalidomide and dexamethasone without the anti-CD38 antibody.

6. The method according to claim 3, wherein the individual achieves a response to the treatment faster than an individual having multiple myeloma who received a treatment comprising pomalidomide and dexamethasone without the anti-CD38 antibody.

7. The method according to claim 1, wherein the anti-CD38 antibody, the pomalidomide, and the dexamethasone are administered in a first 28-day cycle, wherein the anti-CD38 antibody is administered on Days 1, 8, 15, and 22 of the first 28-day cycle, the pomalidomide is administered on each of Days 1-21 of the first 28-day cycle, and the dexamethasone is administered on Days 1, 8, 15, and 22 of the first 28-day cycle.

8. The method according to claim 7, wherein the anti-CD38 antibody, the pomalidomide, and the dexamethasone are further administered in one or more 28-day cycles following the first 28-day cycle, wherein the anti-CD38 antibody is administered on Days 1 and 15 of the one or more 28-day cycles following the first 28-day cycle, the pomalidomide is administered on each of Days 1-21 of the one or more 28-day cycles following the first 28-day cycle, and the dexamethasone is administered on Days 1, 8, 15, and 22 of the one or more 28-day cycles following the first 28-day cycle.

9. The method according to claim 1, wherein the individual was refractory to the most recent prior therapy for multiple myeloma.

10. The method according to claim 9, wherein the most recent prior therapy was lenalidomide or a proteasome inhibitor.

11. The method according to claim 1, wherein the individual has one or more cytogenetic abnormalities selected from the group consisting of: del(17p), t(4;14), and t(14;16).

12. The method according to claim 1, wherein the individual is (a) at least 65 but less than 75 years of age, or (b) 75 years of age or older.

13. The method according to claim 1, wherein the individual has received at least three prior therapies for multiple myeloma.

14. The method according to claim 1, wherein the individual is East Asian.

15. The method according to claim 1, wherein the individual is Stage III according to the International Staging System (ISS) or according to the Revised International Staging System (R-ISS).

16. The method according to claim 1, wherein the individual is minimal residual disease (MRD) negative at a threshold of $10^{-4}$ or less after treatment, at a threshold of $10^{-5}$ or less after treatment, or at a threshold of $10^{-4}$ or less after treatment.

17. The method of claim 1, wherein the complete renal response is an improvement of baseline estimated glomerular filtration rate (eGFR) or creatinine clearance from <50 mL/min/1.73m$^2$ prior to the start of treatment to >60 mL/min/1.73m$^2$ that least one assessment during treatment.

18. The method of claim 1, wherein the complete renal response is a sustained complete renal response.

19. The method of claim 18, wherein the sustained complete renal response is an improvement of baseline estimated glomerular filtration rate (eGFR) or creatinine clearance from <50 mL/min/1.73m$^2$ prior to the start of treatment to >60 mL/min/1.73m$^2$ that is sustained for at least about 60 days.

* * * * *

UNITED STATES PATENT AND TRADEMARK OFFICE
CERTIFICATE OF CORRECTION

PATENT NO. : 11,939,390 B2
APPLICATION NO. : 16/775025
DATED : March 26, 2024
INVENTOR(S) : Heloise Audat et al.

It is certified that error appears in the above-identified patent and that said Letters Patent is hereby corrected as shown below:

In the Claims

In Claim 16, Column 90, Line 14: please replace "$10^{-5}$ or less after treatment, or at a threshold of $10^{-4}$ or less" with --$10^{-5}$ or less after treatment, or at a threshold of $10^{-6}$ or less--, and In Claim 17, Column 90, Line 20: please replace "mL/min/1.73m$^2$ that least one assessment during treatment." with --mL/min/1.73m$^2$ at at least one assessment during treatment--.

Signed and Sealed this
Twentieth Day of August, 2024

*Katherine Kelly Vidal*

Katherine Kelly Vidal
*Director of the United States Patent and Trademark Office*